(12) United States Patent
Wright et al.

(10) Patent No.: US 10,618,266 B2
(45) Date of Patent: Apr. 14, 2020

(54) HYDROPHILIC GEL MATERIALS AND METHODS OF MAKING

(71) Applicant: 3M INNOVATIVE PROPERTIES COMPANY, Saint Paul, MN (US)

(72) Inventors: Robin E. Wright, Inver Grove Heights, MN (US); Stephen E. Krampe, Maplewood, MN (US); Richard L. Walter, Saint Paul, MN (US); Caroline M. Ylitalo, Stillwater, MN (US); William A. Eibner, Saint Paul, MN (US); Jeffrey H. Tokie, Scandia, MN (US); Matthew T. Scholz, Woodbury, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 540 days.

(21) Appl. No.: 14/514,429

(22) Filed: Oct. 15, 2014

(65) Prior Publication Data
US 2015/0027625 A1 Jan. 29, 2015

Related U.S. Application Data

(62) Division of application No. 12/747,558, filed as application No. PCT/US2008/086508 on Dec. 12, 2008, now abandoned.
(Continued)

(51) Int. Cl.
*B32B 37/24* (2006.01)
*B32B 38/00* (2006.01)
(Continued)

(52) U.S. Cl.
CPC .............. *B32B 37/24* (2013.01); *A61L 15/60* (2013.01); *B05D 1/02* (2013.01); *B05D 3/06* (2013.01);
(Continued)

(58) Field of Classification Search
CPC ........................................................ B05D 3/06
(Continued)

(56) References Cited

U.S. PATENT DOCUMENTS 1,529,256 A 3/1925 Kelley
RE24,906 E 12/1960 Ulrich
(Continued)

FOREIGN PATENT DOCUMENTS

CA 1270192 6/1990
EP 0317858 11/1988
(Continued)

OTHER PUBLICATIONS

Barrett, *PMSE Preprints*, "Microcontact Printing of Poly(organophosphazenes): Potential Applications for Selective Cell Adhesion", 2004;91:633-634.
(Continued)

*Primary Examiner* — Ian A Rummel
(74) *Attorney, Agent, or Firm* — 3M Innovative Properties Company; Trisha D. Adamson

(57) ABSTRACT

The present disclosure describes articles, such as medical articles, containing a substrate having disposed thereon a hydrophilic gel material (e.g., a shaped hydrophilic gel material or a coating of a hydrophilic gel material) and methods for making such articles. Methods are provided for making hydrophilic gel materials from a precursor composition that contains a polar solvent and a polymerizable material that is miscible with the polar solvent.

10 Claims, 4 Drawing Sheets

Related U.S. Application Data

(60) Provisional application No. 61/013,300, filed on Dec. 12, 2007, provisional application No. 61/013,617, filed on Dec. 13, 2007, provisional application No. 61/016,312, filed on Dec. 21, 2007.

(51) Int. Cl.
| | |
|---|---|
| *B05D 3/06* | (2006.01) |
| *C09J 133/14* | (2006.01) |
| *B05D 1/02* | (2006.01) |
| *A61L 15/60* | (2006.01) |
| *C08F 2/48* | (2006.01) |
| *C08F 290/06* | (2006.01) |
| *C08F 299/00* | (2006.01) |

(52) U.S. Cl.
CPC .......... *B32B 38/0008* (2013.01); *C08F 2/48* (2013.01); *C08F 290/06* (2013.01); *C08F 290/061* (2013.01); *C08F 290/062* (2013.01); *C08F 299/00* (2013.01); *C09J 133/14* (2013.01); *B32B 2038/0076* (2013.01); *B32B 2305/74* (2013.01); *B32B 2307/728* (2013.01); *B32B 2386/00* (2013.01); *Y10T 428/1352* (2015.01)

(58) Field of Classification Search
USPC ...................................................... 428/195.1
See application file for complete search history.

(56) References Cited

U.S. PATENT DOCUMENTS

| | | | |
|---|---|---|---|
| 3,121,021 | A | 2/1964 | Copeland |
| 3,389,827 | A | 6/1968 | Abere |
| 3,645,835 | A | 2/1972 | Hodgson |
| 4,112,213 | A | 9/1978 | Waldman |
| 4,157,418 | A | 6/1979 | Heilmann |
| 4,444,961 | A | 4/1984 | Timm |
| 4,499,896 | A | 2/1985 | Heinecke |
| 4,597,975 | A | 7/1986 | Woodward |
| 4,598,004 | A | 7/1986 | Heinecke |
| 4,693,776 | A | 9/1987 | Krampe |
| 4,726,989 | A | 2/1988 | Mrozinski |
| 4,867,881 | A | 9/1989 | Kinzer |
| 4,873,299 | A | 10/1989 | Nowakowsky |
| 4,889,530 | A * | 12/1989 | Smith ................ A61L 26/0014 604/304 |
| 4,929,400 | A | 5/1990 | Rembaum |
| 4,971,732 | A | 11/1990 | Wichterle |
| 5,064,652 | A | 11/1991 | Bay |
| 5,088,483 | A | 2/1992 | Heinecke |
| 5,120,594 | A | 6/1992 | Mrozinski |
| 5,126,381 | A | 6/1992 | Liscomb |
| 5,160,315 | A | 11/1992 | Heinecke |
| 5,260,360 | A | 11/1993 | Mrozinski |
| 5,435,816 | A | 7/1995 | Spurgeon |
| 5,437,932 | A | 8/1995 | Ali |
| 5,506,279 | A | 4/1996 | Babu |
| 5,531,855 | A | 7/1996 | Heinecke |
| 5,667,541 | A | 9/1997 | Klun |
| 5,670,557 | A | 9/1997 | Dietz |
| 5,674,561 | A | 10/1997 | Dietz |
| 5,690,705 | A | 11/1997 | Holmes |
| 5,714,259 | A | 2/1998 | Holmes |
| 5,733,570 | A | 3/1998 | Chen |
| 5,738,642 | A | 4/1998 | Heinecke |
| 5,779,632 | A | 7/1998 | Dietz |
| 5,849,325 | A | 9/1998 | Heinecke |
| 5,962,544 | A | 10/1999 | Waller, Jr. |
| 6,372,407 | B1 | 4/2002 | Liu |
| 6,376,590 | B2 | 4/2002 | Kolb |
| 6,386,699 | B1 | 5/2002 | Ylitalo |
| 6,407,195 | B2 | 6/2002 | Sherman |
| 6,566,575 | B1 | 5/2003 | Stickels |
| 6,649,249 | B1 | 11/2003 | Engle |
| 6,709,716 | B2 | 3/2004 | Uy |
| 6,960,275 | B2 | 11/2005 | Vesley |
| 7,005,143 | B2 | 2/2006 | Abuelyaman |
| 7,105,809 | B2 | 9/2006 | Wood |
| 7,223,364 | B1 | 5/2007 | Johnston |
| 7,420,013 | B2 | 9/2008 | Riegel |
| 2002/0122771 | A1* | 9/2002 | Holland .............. A61L 26/0066 424/43 |
| 2003/0021961 | A1 | 1/2003 | Ylitalo |
| 2003/0054025 | A1 | 3/2003 | Cantor |
| 2005/0049323 | A1* | 3/2005 | Gvozdic ................. C08J 3/075 521/141 |
| 2005/0058821 | A1 | 3/2005 | Smith |
| 2005/0215752 | A1 | 9/2005 | Popp |
| 2006/0034899 | A1 | 2/2006 | Ylitalo |
| 2006/0035039 | A1 | 2/2006 | Ylitalo |
| 2006/0051384 | A1 | 3/2006 | Scholz |
| 2006/0051385 | A1 | 3/2006 | Scholz |
| 2006/0052452 | A1 | 3/2006 | Scholz |
| 2006/0148950 | A1 | 7/2006 | Davidson |
| 2006/0155057 | A1 | 7/2006 | Hermeling |
| 2006/0212011 | A1 | 9/2006 | Popp |
| 2006/0235141 | A1 | 10/2006 | Riegel |
| 2007/0031505 | A1 | 2/2007 | Roy |
| 2007/0048505 | A1 | 3/2007 | Shimada |
| 2007/0196601 | A1 | 8/2007 | Ray |
| 2008/0207794 | A1 | 8/2008 | Wright |
| 2008/0300339 | A1 | 12/2008 | Wright |

FOREIGN PATENT DOCUMENTS

| | | |
|---|---|---|
| EP | 1245240 | 10/2002 |
| JP | 10018125 | 1/1998 |
| JP | 11-092305 | 4/1999 |
| JP | 2002180361 | 6/2002 |
| WO | WO 2000/73082 | 12/2000 |
| WO | WO 2007/73083 | 12/2000 |
| WO | WO 2001/02093 | 1/2001 |
| WO | WO 2001/41818 | 6/2001 |
| WO | WO 2004-000568 | 12/2003 |
| WO | WO 2004/000569 | 12/2003 |
| WO | WO 2004/087635 | 10/2004 |
| WO | WO 2006/011062 | 2/2006 |
| WO | WO 2006/027702 | 3/2006 |
| WO | WO 2006/027703 | 3/2006 |
| WO | WO 2006/079631 | 8/2006 |
| WO | WO 2007/018422 | 2/2007 |
| WO | WO 2007/070310 | 6/2007 |
| WO | WO 2007/146722 | 12/2007 |

OTHER PUBLICATIONS

Calvert, 224th ACS National Meeting. Abstract MTLS-008. 2002.
DiRamio, "Poly(ethylene glycol) Methacrylate/Dimethacrylate Hydrogels for Controlled Release of Hydrophobic Drugs," *Biotechnol. Prog.*, Jul.-Aug. 2005;21(4):1281-8.
Drtina, "Highly Cross-Linked Azlactone Functional Supports of Tailorable Polarity," *Macromolecules*, 1996;29(13):4486-4489.
Hanh, *Biomaterials*, 2006;27(12):2519-2524.
Karp, *Biomaterials* 27 (2006), "A photolithographic method to create cellular micropatterns", Feb. 15, 2006; (27):4755-4764.
Kizilel, "Photopolymerization of Poly(Ethylene Glycol) Diacrylate on Eosin-Functionalized Surfaces," *Langmuir*, Sep. 28, 2004;20(20):8652-8658.
Lee, "Multilayer Transfer Printing on Microreservoir-Patterned Substrate Employing Hydrophilic Composite Mold for Selective Immobilization of Biomolecules," *Langmuir*, Aug. 29, 2006; 22(18): 7689-7694.
Lensen, "Micro- and Nanopatterened Star Poly(ethylene glycol) (PEG) Materials Prepared by UV-based Imprint Lithography," *Langmuir*, Jul. 3, 2007;23(14):7841-6.
Wente, V.A., "Superfine Thermoplastic Fibers," *Industrial Engineering Chemistry*, 1956;48:1342-1346.
Wente, V.A., "Manufacture of Super Fine Organic Fibers," *Naval Research Laboratories*, Report No. 4364, May 25, 1954.

(56) References Cited

OTHER PUBLICATIONS

Zhou, *229$^{th}$ ACS National Meeting*, Abstract BIOT-078, 2005.
U.S. Appl. No. 61/013,300, filed Dec. 12, 2007.
U.S. Appl. No. 61/016,312, filed Dec. 21, 2007.
U.S. Appl. No. 61/013,617, filed Dec. 13, 2007.
U.S. Appl. No. 61/013,085, filed Dec. 12, 2007.
International Search Report, PCT/US2008/086508, dated Mar. 11, 2009, 6 pages.
Written Opinion of the International Searching Authority, PCT/US2008/086508, dated Mar. 11, 2009, 8 pages.

\* cited by examiner

HYDROPHILIC GEL MATERIALS AND METHODS OF MAKING

CROSS REFERENCE TO RELATED APPLICATIONS

This application is a divisional of the U.S. Ser. No. 12/747,558, filed Jun. 11, 2010, which is a 35 U.S.C. 371 of PCT/US2008/086508, filed Dec. 12, 2008, which claims priority to U.S. Application No. 61/013,300, filed on Dec. 12, 2007; U.S. Application No. 61/013,617, filed on Dec. 13, 2007; and U.S. Application No. 61/016,312, filed on Dec. 21, 2007, the disclosures of which is incorporated by reference in their entirety herein.

BACKGROUND

There are numerous commercial uses for hydrophilic gel materials including industrial, medical, and biological uses. Applications for hydrophilic gel materials continue to increase and expand in scope. For example, numerous applications are available for hydrophilic gel materials having defined shapes in biological uses, medical uses, and industrial uses. Also, there is a continuing need for hydrophilic gel materials with unique physical properties, chemical properties, and versatility, including, for example, those having defined shapes.

Numerous methods for making hydrophilic gel materials, including those having defined shapes, are known. For example, molds for forming hydrophilic gel materials with defined shapes are known. There is always a desire for improvements in hydrophilic gel materials and processes for making them. In particular, there is a desire for new hydrophilic gel materials on a substrate suitable for medical and biological applications, such as in wound care articles (e.g., bandages and wound dressings), which are available in a variety of designs to protect wounds from environmental conditions during the healing process. For example, coating a hydrophilic gel material containing one or more biological actives, such as antimicrobials, onto a substrate may be desirable in wound care articles to prevent or treat infections. There is also a need for forming hydrophilic gel materials having defined shapes on a microscopic level for use in many applications.

SUMMARY

The present disclosure describes hydrophilic gel-containing articles and methods for making such articles.

In one embodiment, the present invention provides a method of making an article comprising a substrate and a hydrophilic gel material disposed thereon (preferably, adhered thereto), the method comprising: providing a precursor composition comprising: (a) at least 10 weight percent polar solvent based on a total weight of the precursor composition; and (b) polymerizable material capable of free-radical polymerization and having an average number of ethylenically unsaturated groups per molecule equal to at least 1.2, wherein the polymerizable material is miscible with the polar solvent; providing a mold having at least two separate wells; adding the precursor composition to the mold, the precursor composition being positioned in at least a portion of at least two separate wells; providing a substrate and positioning the substrate to at least partially contact the precursor composition; and exposing the precursor composition within the wells to radiation to at least partially polymerize the polymerizable material and to form a first swollen shaped hydrophilic gel material on (preferably, adhered to) the substrate.

In another embodiment, the present invention provides a method of making an article comprising a substrate and a hydrophilic gel material disposed thereon (preferably, adhered thereto), the method comprising: providing a precursor composition comprising: (a) at least 5 weight percent polar solvent based on a total weight of the precursor composition; and (b) polymerizable material capable of free-radical polymerization and having an average number of ethylenically unsaturated groups per molecule greater than 1.0, wherein the polymerizable material is miscible with the polar solvent; providing a mold having a substrate in contact therewith in a manner to form at least two separate wells; adding the precursor composition to the mold, the precursor composition being positioned in at least a portion of at least two separate wells; and exposing the precursor composition within the wells to radiation to at least partially polymerize the polymerizable material and to form a first swollen shaped hydrophilic gel material on (preferably, adhered to) the substrate.

In another embodiment, the present invention provides a method of making an article comprising a substrate and a hydrophilic gel material disposed thereon (preferably adhered thereto), the method comprising: providing a precursor composition comprising: (a) at least 5 weight percent polar solvent based on a total weight of the precursor composition; and (b) polymerizable material capable of free-radical polymerization and having an average number of ethylenically unsaturated groups per molecule greater than 1.0, wherein the polymerizable material is miscible with the polar solvent; coating the precursor composition on at least a portion of at least one surface of a substrate; and exposing the precursor composition to radiation to at least partially polymerize the polymerizable material to provide a coating of first swollen hydrophilic gel material on (preferably, adhered to) the substrate.

The present invention also provides an article comprising a substrate and a shaped hydrophilic gel material disposed thereon (preferably, adhered thereto), the article made by one of the methods described herein.

The present invention also provides an article comprising a substrate and a coating of a hydrophilic gel material disposed thereon (preferably, adhered thereto), the article made by one of the methods described herein.

In one embodiment, the present invention provides an article comprising a substrate having a shaped hydrophilic gel material disposed thereon (preferably, adhered thereto), wherein the shaped hydrophilic gel material is prepared from a precursor composition that is at least partially polymerized and shaped in a mold having at least two separate wells (when in contact with the substrate), wherein the precursor composition comprises: (a) at least 10 weight percent polar solvent based on the total weight of the precursor composition, wherein the polar solvent comprises water; and (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide) (meth)acrylate) having at least 2 (meth)acryloyl groups and having at least 5 alkylene oxide units.

In another embodiment, the present invention provides an article comprising a substrate having a shaped hydrophilic gel material disposed thereon (preferably, adhered thereto), wherein the shaped hydrophilic gel material is prepared from a precursor composition that is at least partially polymerized and shaped in a mold having at least two separate wells (when in contact with the substrate), wherein the precursor composition comprises: (a) at least 10 weight percent polar solvent based on the total weight of the precursor composition; and (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units, the poly(alkylene oxide (meth)acrylate) having a weight average molecular weight less than 2,000 g/mole.

In another embodiment, the present invention provides an article comprising a substrate having a coating of a hydrophilic gel material disposed thereon (preferably, adhered thereto), wherein the hydrophilic gel material is prepared from a precursor composition that is at least partially polymerized (when in contact with the substrate), and wherein the precursor composition comprises: (a) at least 5 weight percent polar solvent based on a total weight of the precursor composition; and (b) polymerizable material capable of free-radical polymerization and having an average number of ethylenically unsaturated groups per molecule greater than 1.0, wherein the polymerizable material is miscible with the polar solvent.

Articles of the present invention may include an active agent (preferably, a bioactive agent) in the hydrophilic gel material. This may be added in the precursor composition, or it may be added by first removing at least a portion of the polar solvent from the (first swollen) hydrophilic gel material to form a dried hydrophilic gel material, and then contacting the dried hydrophilic gel material with a sorbate for a time sufficient for the dried shaped hydrophilic gel material to sorb at least a portion of the sorbate, wherein the sorbate comprises at least one active agent.

Articles of the present invention can be medical articles comprising the hydrophilic gel material in a layered format. If desired, the hydrophilic gel may be in direct contact with the wound and/or skin surface.

In certain embodiments, such medical articles can be wound dressings. Such wound dressings can include a fluid permeable facing layer and/or a moisture vapor permeable backing layer with the hydrophilic gel layer attached thereto. Preferably, the backing layer is both moisture vapor permeable and liquid impermeable. If desired, the hydrophilic gel may be in direct contact with the wound and/or skin surface.

As used herein "hydrophilic gel" or "hydrogel" refers to hydrophilic polymeric material that is swollen or capable of being swollen with a polar solvent. The polymeric material typically swells but does not dissolve when contacted with the polar solvent. That is, the hydrogel is insoluble in the polar solvent.

Herein, "precursor composition" refers to the reactant mixture that is subjected to radiation. That is, the precursor composition describes the reaction mixture prior to polymerization. The precursor composition contains a polar solvent and polymerizable material that is miscible with the polar solvent. The precursor composition can also include other optional additives such as processing agents, active agents, or mixtures thereof.

As used herein the terms "front surface" and "back surface" used with respect to the hydrophilic gel layer and the backing layer, refers to the major surface of the indicated layer that, in use, faces toward the wound surface or away from the wound surface, respectively.

The recitation of numerical ranges by endpoints includes all numbers subsumed within that range (e.g., 1 to 5 includes 1, 1.5, 2, 2.75, 3, 3.8, 4, and 5). As used herein, "up to" a value "includes" that value.

As included in this specification and the appended claims, the singular forms "a", "an", and "the" include plural referents unless the content clearly dictates otherwise. Thus, for example, reference to a composition containing "a compound" includes a mixture of two or more compounds. As used in this specification and appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains errors necessarily resulting from the standard deviations found in their respective testing measurements.

Although the present disclosure is herein described in terms of specific embodiments, it will be readily apparent to those skilled in the art that various modifications, rearrangements, and substitutions can be made without departing from the spirit of the invention. The scope of the present invention is thus only limited by the claims appended hereto.

DETAILED DESCRIPTION IN ILLUSTRATIVE EMBODIMENTS

Figure 1:
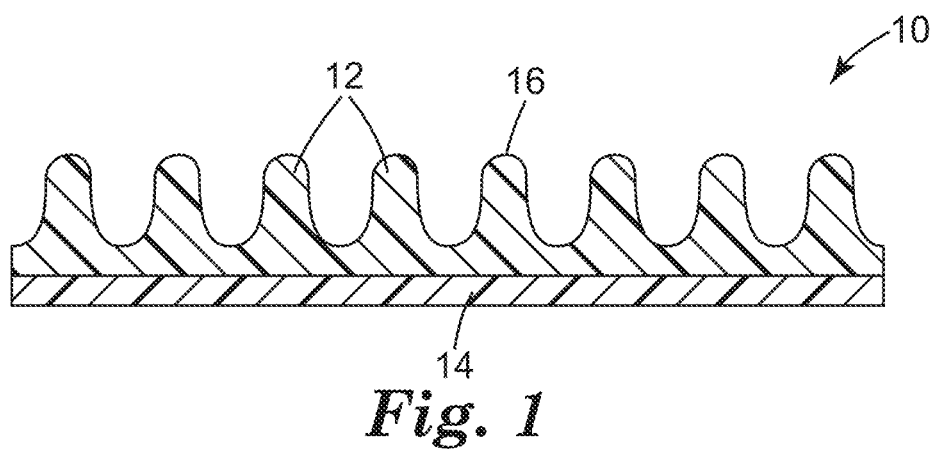
FIG. 1 is a cross-section of an exemplary article according to the present invention.

The present invention provides articles, such as medical articles, that include a substrate having a hydrophilic gel material disposed thereon, and methods for making such articles from a precursor composition. In certain embodiments, the hydrophilic gel material is shaped. In certain other embodiments, the hydrophilic gel material forms a coating, such as a discontinuous coating, on the substrate. Typically, for forming a discontinuous coating, a hydrophilic gel material is disposed on a substrate by non-contact deposition.

The precursor composition useful for making hydrophilic gel materials includes a polar solvent and a polymerizable material. In most embodiments, the polymerizable material forms a single phase with the polar solvent. That is, the polymerizable material is miscible in the polar solvent. As used herein, the term "miscible" means that the polymerizable material is predominantly soluble in the polar solvent or compatible with the polar solvent such that a single phase is formed.

The polymerizable material has ethylenically unsaturated groups which can be at least partially polymerized when exposed to radiation. The polymerizable material has an average number of ethylenically unsaturated groups per molecule equal to at least 1.0, greater than 1.0, and more preferably at least 1.2, and is capable of free-radical polymerization. Herein, "polymerizable material" does not include the polar solvent.

For preparing articles with shaped hydrophilic gel material disposed on a substrate, the precursor composition is added to a mold having at least two separate wells, and then exposed to radiation to at least partially polymerize the polymerizable material to form a swollen shaped polymeric material (i.e., a swollen shaped hydrophilic gel material (e.g., a crosslinked hydrogel)). In this embodiment, the swollen shaped polymeric material has a shape and dimensions similar to the wells of the mold. A substrate can be positioned to contact the precursor composition after it is added to the mold; however, the wells of the mold can be formed using the substrate and the precursor composition added after the substrate is positioned on the mold in a manner to form such wells. Such a mold would typically only have sidewalls and the bottom of each well would be formed by the substrate.

For preparing articles with a hydrophilic gel material coated on a substrate, the precursor composition can be coated on a substrate using a wide variety of techniques. In particular, a discontinuous coating of a hydrophilic gel material can be coated on a substrate by non-contact deposition of the precursor composition onto the substrate. After coating the precursor composition onto the substrate, the precursor composition may be at least partially solidified by exposing the precursor composition to radiation either directly or through the substrate or both. The radiation at least partially polymerizes the polymerizable material and forms a substrate with a coating, e.g., a discontinuous coating, of first swollen hydrophilic gel material on the substrate surface. The polymerizable material polymerizes by a free-radical polymerization process.

Thus, the present invention provides several methods. In one exemplary method, a precursor composition is provided that includes at least 10 weight percent of a polar solvent based on the total weight of the precursor composition and no greater than 90 weight percent of a polymerizable material based on the total weight of the precursor composition. The polar solvent comprises water. The polymerizable material forms a single phase with the polar solvent and is capable of free-radical polymerization. The polymerizable material has an average number of ethylenically unsaturated groups per molecule equal to at least 1.0, preferably greater than 1.0, and more preferably at least 1.2. The polymerizable material comprises a poly(alkylene oxide (meth)acrylate) having at least 2 (meth)acryloyl groups and at least 5 alkylene oxide units. The method further includes providing a mold having at least two separate wells. The precursor composition is added to the mold and positioned in at least a portion of the at least two separate wells. The method further includes providing a substrate and positioning it to at least partially contact the precursor composition. Within the wells, the precursor composition is exposed to radiation to at least partially polymerize the polymerizable material, and to form a first swollen shaped polymeric material.

In another exemplary method, a precursor composition is provided that includes: (a) at least 10 weight percent polar solvent based on the total weight of the precursor composition, wherein the polar solvent comprises water; and (b) no greater than 90 weight percent polymerizable material based on the total weight of the precursor composition, the polymerizable material being capable of free-radical polymerization and having an average number of ethylenically unsaturated groups per molecule equal to at least 1.0, preferably greater than 1.0, and more preferably at least 1.2, wherein the polymerizable material forms a single phase with the polar solvent and comprises a poly(alkylene oxide (meth) acrylate) having at least 2 (meth)acryloyl groups and having at least 5 alkylene oxide units. The method further includes providing a mold having a substrate in contact therewith in a manner to form at least two separate wells; adding the precursor composition to the mold, the precursor composition being positioned in at least a portion of at least two separate wells; and exposing the precursor composition within the wells to radiation to at least partially polymerize the polymerizable material and to form a first swollen shaped hydrophilic gel material on a substrate.

In yet another exemplary method, a precursor composition is provided that includes at least 10 weight percent, and preferably greater than 10 weight percent, of a polar solvent based on the total weight of the precursor composition, and a polymerizable material (preferably no greater than 90 weight percent based on the total weight of the precursor composition). The polymerizable material forms a single phase with the polar solvent and is capable of free-radical polymerization. The polymerizable material has an average number of ethylenically unsaturated groups per molecule equal to at least 1.0, preferably greater than 1.0, and more preferably at least 1.2. In certain embodiments, the polymerizable material comprises a poly(alkylene oxide (meth) acrylate) having at least 2 (meth)acryloyl groups and at least 5 alkylene oxide units. The average molecular weight of the poly(alkylene oxide (meth)acrylate) is less than 2,000 g/mole. The method further includes providing a mold having at least two separate wells. The precursor composition is added to the mold, and positioned in at least a portion of the at least two separate wells. The method further includes providing a substrate and positioning the substrate to contact the precursor composition. Within the wells, the precursor composition is exposed to radiation (e.g., through the substrate and/or mold) to at least partially polymerize the polymerizable material, and to form a first swollen shaped polymeric material.

In still another exemplary method, a precursor composition is provided that includes: (a) at least 5 weight percent (for certain embodiments, at least 10 weight percent) polar solvent based on the total weight of the precursor composition; and (b) a polymerizable material (preferably, no greater than 90 weight percent based on the total weight of the precursor composition), the polymerizable material being capable of free-radical polymerization. The polymerizable material has an average number of ethylenically unsaturated groups per molecule equal to at least 1.0, preferably greater than 1.0, and more preferably at least 1.2. In certain embodiments, the polymerizable material forms a single phase (or is miscible) with the polar solvent and comprises a poly(alkylene oxide (meth)acrylate) having at least 2 (meth)acryloyl groups and having at least 5 alkylene oxide units, the poly(alkylene oxide (meth)acrylate) having a weight average molecular weight less than 2,000 g/mole. The method further includes: providing a mold having a substrate in contact therewith in a manner to form at least two separate wells; adding the precursor composition to the mold, the precursor composition being positioned in at least a portion of at least two separate wells; and exposing the precursor composition (e.g., through the substrate and/or the mold) within the wells to radiation to at least partially polymerize the polymerizable material and to form a first swollen shaped hydrophilic gel material on a substrate.

In another exemplary embodiment, the method for making a substrate with a coating, preferably a discontinuous coating, of hydrophilic gel material comprises providing a precursor composition having a polymerizable material containing a poly(alkylene oxide (meth)acrylate) having at least 2 (meth)acryloyl groups and at least 5 alkylene oxide units such that the poly(alkylene oxide (meth)acrylate) has an average molecular weight less than 2,000 g/mole, and a polar solvent. The polymerizable material has an average number of ethylenically unsaturated groups per molecule equal to at least 1.0, and more preferably 1.2, and is capable of free-radical polymerization.

The polar solvent does not necessarily include water. The method for making the substrate with a coating of hydrophilic gel material comprises providing a substrate onto which the precursor composition is coated onto the substrate. Typically, for a discontinuous coating this is done by non-contact deposition. The coating of the precursor composition on the substrate, whether a discontinuous or continuous coating, is exposed to radiation directly or through the substrate or both to at least partially polymerize the polymerizable material, and to form a substrate containing a coating of first swollen hydrophilic gel material.

Swollen hydrophilic gel materials are generally referred to as hydrogels. Hydrogels are hydrophilic materials, and can be swollen or are capable of being swollen with a polar solvent (e.g., water). Hydrogels can be swollen with polar solvents other than water. Hydrogels typically do not dissolve when contacting a polar solvent, but rather swell. Hydrogels can be dried to remove at least some of the polar solvent to form dried hydrogels.

Swollen hydrophilic gel materials are commonly referred to as crosslinked hydrogels. Herein, hydrophilic gel materials include both shaped materials and coatings, whether discontinuous or continuous.

A shaped hydrophilic gel material can be described as a shaped polymeric material, a hydrogel shaped polymeric material, a shaped polymeric material swollen with solvent, a polymeric shaped hydrophilic gel material, a dried shaped hydrophilic gel material, or a dried shaped polymeric material, for example. All these terms may be used herein, depending on the condition of being dried or swollen.

A coating of hydrophilic gel material can be described as a swollen coating of hydrophilic gel material or a hydrogel coating of hydrophilic gel material. A discontinuous coating of hydrophilic gel material can be described as a swollen discontinuous coating of hydrophilic gel material or a discontinuous hydrogel coating of hydrophilic gel material.

The polymeric material in the swollen hydrophilic gel material may be generally crosslinked, but it may contain some unreacted polymerizable or reactive groups. The unreacted polymerizable groups typically include ethylenically unsaturated groups capable of further free-radical reactions. Other types of polymerizable groups such as hydroxyl groups or amino groups can be present that are capable of condensation reactions or nucleophilic substitution reactions.

Whatever the nature of the basic polymer components of the hydrophilic gel material used herein, such materials will preferably be crosslinked. Crosslinking serves to render the hydrophilic gel materials used in this invention substantially water-insoluble, and crosslinking thus, in part, determines the gel volume and extractable polymer characteristics of the hydrophilic gel materials formed. The crosslinked, hydrogel-forming polymer gelling agents used in the present invention may be employed in their partially neutralized form. Suitable salt-forming cations include, but are not limited to, alkali metal, ammonium, substituted ammonium and amines. This percentage of the total monomers utilized that are neutralized acid group-containing monomers is referred to herein as the "degree of neutralization."

Optionally, an active agent may be included in the hydrophilic gel materials of the present invention. Some exemplary swollen hydrophilic gel materials may contain no greater than 90 weight percent polymeric material, at least 10 weight percent polar solvent, and 0 to 30 weight percent active agent based on a total weight of the hydrophilic gel materials.

The polymeric matrix, which includes the polar solvent and polymeric material, is usually present as a single phase in the swollen hydrophilic gel material, with no discernible boundary between the solvent and the polymeric material. If an active agent is present, however, the active agent may or may not be distributed homogeneously throughout the hydrophilic gel material. Further, the active agent may be present in a separate phase from the polymeric matrix.

Generally, the homogeneity of the hydrophilic gel materials (i.e., without an active agent) are characterized by having no discernible porosity or voids when viewed under a microscope such as an environmental scanning electron microscope with magnification up to 50 times. The hydrophilic gel materials often have no discernible porosity or voids when viewed under a field emission scanning electron microscope with a magnification up to 50,000 times.

Swollen hydrophilic gel materials that are prepared without the use of opaque components that might scatter light can be clear or transparent, with little or no opacity or haziness. In some embodiments, swollen hydrophilic gel materials that are clear are preferred. In other embodiments, clarity is not necessary and various components can be added that may affect the appearance of the hydrophilic gel materials.

The term "transparent" as used in reference to the hydrophilic gel materials, means that the hydrophilic gel materials do not show significant scatter of visible light in an amount that can be visually detected. In some embodiments, air or other gases may be entrained in the hydrophilic gel materials, which can create opacity at the phase boundaries; however, this is not phase-separation of the polymeric material in the polar solvent. Hydrophilic gel materials are considered transparent if a colorless, virtually void-free cured film having a thickness of 250 microns containing smooth or flat parallel faces (i.e., patternless) has a transmission at a wavelength of 550 nanometers of at least 85 percent. In some embodiments, at least 88 percent, at least 90 percent, at least 95 percent of light having a wavelength of 550 nanometers is transmitted through the hydrophilic gel material.

The haze or opacity can be characterized using a haze meter, such as a BYK-Gardner Hazegard Plus hazemeter, which has a broadband light source. The transmittance through hydrophilic gel material can be at least 85 percent, at least 88 percent, at least 90 percent, or at least 95 percent with haze being less than 10 percent, less than 8 percent, less than 5 percent, or less than 3 percent.

Precursor Composition

The precursor composition for making materials of the present invention (e.g., shaped hydrophilic gel materials) includes a polar solvent and a polymerizable material. In certain embodiments, the precursor composition includes at least 5 weight percent (wt-%), greater than 5 weight percent, at least 10 weight percent, or greater than 10 weight percent, of a polar solvent based on the total weight of the precursor composition. In certain embodiments, the precursor composition includes no greater that 90 weight percent polymerizable material based on the total weight of the precursor composition. The polymerizable material is capable of free-radical polymerization when exposed to radiation. The polymerizable material has an average number of ethylenically unsaturated groups per molecule equal to at least 1.0, preferably greater than 1.0, and more preferably at least 1.2. In certain embodiments, the polymerizable material forms a single phase with (or is miscible in) the polar solvent. In certain embodiments, the polymerizable material comprises a poly(alkylene oxide (meth)acrylate) having at least 2 (meth)acryloyl groups and at least 5 alkylene oxide units. In some embodiments, the polar solvent comprises water. In other embodiments, the polar solvent may not comprise water.

In one aspect, the precursor composition contains polar solvent comprising water and a polymerizable material.

In a second aspect, the precursor composition comprises a polar solvent and a polymerizable material containing a poly(alkylene oxide (meth)acrylate) having at least 2 (meth) acryloyl groups, at least 5 alkylene oxide units, and an average molecular weight less than 2,000 g/mole. The polar solvent does not necessarily comprise water.

The polar solvent of the precursor composition may contain water, a water-miscible organic solvent, or a mixture thereof. The polar solvent is generally not reactive in the precursor composition, such that the polar solvent typically swells the resulting hydrophilic gel material. In some instances, the polar solvent may be involved in chain transfer reactions. The polymerizable material is at least partially polymerized in the presence of the polar solvent resulting in a hydrophilic gel material swollen with the polar solvent. Swollen hydrophilic gel materials generally contain at least some of the polar solvents of the precursor composition.

The polar solvent can be tap water, well water, deionized water, spring water, distilled water, sterile water, sea water, inorganic aqueous buffer solutions, organic aqueous buffer solutions or any other suitable type of water. A water miscible organic solvent refers to an organic solvent that is typically capable of hydrogen bonding and forms a single phase solution when mixed with water at 23° C. Water miscible solvents often contain hydroxyl or oxy groups, including alcohols, polyols having a weight average molecular weight no greater than 300 g/mole, ethers, and polyethers having a weight average molecular weight no greater than 300 g/mole. Some examples of water miscible solvents include, but are not limited to, methanol, ethanol, isopropanol, n-propanol, ethylene glycol, triethylene glycol, glycerol, polyethylene glycol, propylene glycol, dipropylene glycol, polypropylene glycol, random and block copolymers of ethylene oxide and propylene oxide, dimethyoxytetraglycol, butoxytriglycol, trimethylene glycol trimethyl ether, ethylene glycol dimethyl ether, ethylene glycol monobutyl ether, ethylene glycol monoethyl ether, ethylene carbonate, dimethylformamide, N-methylpyrrolidinone, urea, and mixtures thereof. The solvent can be a liquid, or a melted solid at or above 23° C.

In some precursor compositions, the polar solvent present in the precursor composition is at least 5 weight percent, or greater than 5 weight percent, based on the total weight of the precursor composition. In some precursor compositions, the polar solvent present in the precursor composition is at least 10 weight percent, or greater than 10 weight percent, based on the total weight of the precursor composition. In some precursor compositions, the polar solvent present in the precursor composition can be at least 15 weight percent, at least 20 weight percent, at least 25 weight percent, at least 40 weight percent, or at least 50 weight percent based on the total weight of the precursor composition. The polar solvent present in the precursor composition can be in an amount up to (which "includes") 90 weight percent, up to 85 weight percent, up to 80 weight percent, up to 65 weight percent, or up to 60 weight percent based on the total weight of the precursor composition. The polar solvent present in the precursor composition can be in a range of 10 to 90 weight percent, 10 to 85 weight percent, 15 to 80 weight percent, or in a range of 20 to 65 percent based on the total weight of the precursor composition.

In addition to the polar solvent, the precursor composition includes a polymerizable material that is miscible with the polar solvent. Polymerizable material generally refers to a monomer, an oligomer, or a mixture of monomers and/or oligomers. The terms "monomer" and "monomer molecule" are used interchangeably to refer to a compound that contains at least one polymerizable group capable of free-radical polymerization. The polymerizable group is usually an ethylenically unsaturated group.

The polymerizable material includes a monomer and/or oligomer of a single chemical structure, or it may include a plurality of different monomers and/or oligomers (i.e., a mixture of monomers and/or oligomers having different chemical structures). Whether the polymerizable material includes one monomer/oligomer or a mixture of monomers/ oligomers, the polymerizable material has an average number of polymerizable groups (e.g., ethylenically unsaturated groups) per molecule equal to at least 1.0, preferably greater than 1.0, and more preferably at least 1.2. The polymerizable material can include, for example, a single type of monomer that has two or more polymerizable groups. Alternatively, the polymerizable material can include a plurality of different types of monomers such that the average number of polymerizable groups per molecule is equal to at least 1.0, preferably greater than 1.0, and more preferably at least 1.2. In some embodiments, the average number of polymerizable groups per (monomer or oligomer) molecule is equal to at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, or at least 3.0.

The average number of polymerizable groups per molecule is determined by calculating the relative molar concentration of each monomer molecule and its functionality (number of polymerizable groups). For example, a polymerizable material that contains X mole percent of a first monomer having n polymerizable groups and (100−X) mole percent of a second monomer having m polymerizable groups has an average number of polymerizable groups per molecule equal to [n(X)+m(100−X)]/100. In another example, a polymerizable material that contains X mole percent of a first monomer having n polymerizable groups, Y mole percent of a second monomer having m polymerizable groups, and (100−X−Y) mole percent of a third monomer having q polymerizable groups has an average number of polymerizable groups per molecule equal to [n(X)+m(Y)+q(100−X−Y)]/100.

The polymerizable material of the precursor composition comprises monomers with ethylenically unsaturated groups capable of free radical polymerization. The polymerizable material forms a single phase with the polar solvent and does not phase separate from the polar solvent at 23° C. The polymerizable material is considered miscible with the polar solvent, such that polymerizable material is predominantly soluble or compatible in the polar solvent. The single phase is essentially transparent as determined by visible spectroscopy on a cured 250 micron thick film formed from the precursor composition having light transmission of at least 85 percent or greater at a wavelength of 550 nm. On occasion, there can be a small amount of undissolved polymerizable material in the polar solvent. For example, the polymerizable material may have an impurity that does not dissolve in the polar solvent. Preferably, at least 95 weight percent, at least 97 weight percent, at least 98 weight percent, at least 99 weight percent, at least 99.5 weight percent, at least 99.8 weight percent, or at least 99.9 weight percent of the polymerizable material is soluble in the polar solvent.

The polymerizable material includes at least one monomer having two or more polymerizable groups. Likewise, a first monomer having three or more polymerizable groups can be mixed with a second monomer having one polymerizable group, a second monomer having two polymerizable groups, or a mixture thereof provided that the mixture contains an average number of polymerizable groups per molecule equal to at least 1.0, preferably greater than 1.0, and more preferably at least 1.2. Often, a monomer nominally having three or more polymerizable groups contains monomeric impurities having two polymerizable groups, one polymerizable group, or a mixture thereof.

The polymerizable material often includes one or more (meth)acrylates. As used herein, the term "(meth)acrylate" refers to a methacrylate, acrylate, or mixture thereof. The (meth)acrylate contains a (meth)acryloyl group. The term "(meth)acryloyl" refers to a monovalent group of formula $H_2C=CR^b-(CO)-$ where $R^b$ is hydrogen or methyl, and (CO) denotes that the carbon is attached to the oxygen with a double bond. The (meth)acryloyl group is the polymerizable group (i.e., the ethylenically unsaturated group) of the (meth)acrylate that is capable of free-radical polymerization. All of the polymerizable materials can be (meth)acrylates or the polymerizable materials can include one or more (meth) acrylates in combination with other monomers that have ethylenically unsaturated groups.

The polymerizable material of the precursor composition includes a poly(alkylene oxide (meth)acrylate). The terms poly(alkylene oxide (meth)acrylate), poly(alkylene glycol (meth)acrylate), alkoxylated (meth)acrylate, and alkoxylated poly(meth)acrylate can be used interchangeably to refer to a (meth)acrylate having at least one group that contains two or more alkylene oxide residue units (also referred to as alkylene oxide units). There are often at least 5 alkylene oxide residue units. The alkylene oxide unit is a divalent group of formula —OR— where R is an alkylene having up to 10 carbon atoms, up to 8 carbon atoms, up to 6 carbon atoms, or up to 4 carbon atoms. The alkylene oxide units are often selected from ethylene oxide units, propylene oxide units, butylene oxide units, or mixtures thereof.

In some embodiments, the polymerizable material includes a poly(alkylene oxide (meth)acrylate) having at least 2 (meth)acryloyl groups per molecule. The poly(alkylene oxide (meth)acrylate) can be used alone or in combination with other monomers/oligomers to provide an average of at least 1.0, preferably greater than 1.0, and more preferably at least 1.2 ethylenically unsaturated groups per molecule. The alkoxylated portion (i.e., the poly(alkylene oxide) portion) often has at least 5 alkylene oxide units selected from ethylene oxide units, propylene oxide units, butylene oxide units, or a combination thereof. That is, each mole of the poly(alkylene oxide (meth)acrylate) contains at least 5 moles of alkylene oxide units. The plurality of alkylene oxide units facilitates the solubility of the poly (alkylene oxide (meth)acrylate) in the polar solvent. Some exemplary poly(alkylene oxide (meth)acrylates) contain at least 6 alkylene oxide units, at least 8 alkylene oxide units, at least 10 alkylene oxide units, at least 12 alkylene oxide units, at least 15 alkylene oxide units, at least 20 alkylene oxide units, at least 30 alkylene oxide units, or at least 50 alkylene oxide units. The poly(alkylene oxide (meth)acrylate) can contain poly(alkylene oxide) chains that are homopolymer chains, block copolymer chains, random copolymer chains, or mixtures thereof. In some embodiments, the poly(alkylene oxide) chains are poly(ethylene oxide) chains.

Any molecular weight of the poly(alkylene oxide (meth) acrylate) having at least 2 (meth)acryloyl groups can be used as long as hydrophilic gel materials (e.g., shaped hydrophilic gel materials) can be formed from the precursor composition. The weight average molecular weight of the poly (alkylene oxide (meth)acrylate) is often no greater than 2,000 g/mole, or is often less than 2,000 g/mole, less than 1,800 g/mole, less than 1,600 g/mole, less than 1,400 g/mole, less than 1,200 g/mole, or less than 1,000 g/mole.

The preparation of some exemplary poly(alkylene oxide (meth)acrylates) having multiple (meth)acryloyl groups are described in U.S. Pat. No. 7,005,143 (Abuelyaman et al.), and U.S. Pat. Appl. Pub. Nos. 2005/0215752 A1 (Popp et al.), 2006/0212011 A1 (Popp et al.), and 2006/0235141 A1 (Riegel et al.). Suitable poly(alkylene oxide (meth)acrylates) having an average (meth)acryloyl functionality per molecule equal to at least 2 and having at least 5 alkylene oxide units are commercially available, for example, from Sartomer (Exton, Pa.) under the trade designations "SR9035" (ethoxylated (15) trimethylolpropane triacrylate), "SR499" (ethoxylated (6) trimethylolpropane triacrylate), "SR502" (ethoxylated (9) trimethylolpropane triacrylate), "SR415" (ethoxylated (20) trimethylolpropane triacrylate), "CD501" (propoxylated (6) trimethylolpropane triacrylate) and "CD9038" (ethoxylated (30) bis-phenol A diacrylate). The number in parentheses refers to the average number of alkylene oxide units per molecule. Other suitable poly (alkylene oxide (meth)acrylates) include polyalkoxylated trimethylolpropane triacrylates such as those commercially available from BASF (Ludwigshafen, Germany) under the trade designation "LAROMER" with at least 30 alkylene oxide units.

In some embodiments, precursor compositions contain a poly(alkylene oxide (meth)acrylate) having at least 2 (meth) acryloyl groups per molecule, having at least 5 ethylene oxide units, and a weight average molecular weight less than 2,000 g/mole. This polymerizable material can be the only polymerizable material in the precursor composition or can be combined with other monomers that form a single phase with the polar solvent. Whether the poly(alkylene oxide) (meth)acrylate is the only monomer in the precursor composition or is combined with other monomers, the polymerizable material has an average functionality per (monomer or oligomer) molecule equal to at least 1.0, preferably greater than 1.0, and more preferably at least 1.2.

More specific precursor compositions contain a poly(ethylene oxide) (meth)acrylate having at least 2 (meth)acryloyl groups per molecule, having at least 5 alkylene oxide units, and preferably having a weight average molecular weight no greater than 2,000 g/mole, or less than 2,000 g/mole. An even more specific exemplary precursor composition can include an ethoxylated trimethylolpropane triacrylate having a weight average molecular weight of no greater than 2,000 g/mole, or less than 2,000 g/mole. Often the ethoxylated trimethylolpropane triacrylate contains impurities having one (meth)acryloyl group, two (meth)acryloyl groups, or mixtures thereof. For example, commercially available "SR415" (ethoxylated (20) trimethylolpropane triacrylate), often has an average functionality per molecule less than 3 (when analyzed, the average functionality per molecule was 2.5). Although impurities may be present, the average functionality per molecule in the precursor composition is equal to at least 1.0, preferably greater than 1.0, and more preferably at least 1.2.

As long as the average number of ethylenically unsaturated groups (e.g., (meth)acryloyl groups) per molecule is equal to at least 1.0, preferably greater than 1.0, and more preferably at least 1.2, the polymerizable material can include a single (meth)acrylate (i.e., poly(alkylene oxide) (meth)acrylate) or a mixture of (meth)acrylates. To provide an average number of (meth)acryloyl groups per molecule equal to at least 1.0, preferably greater than 1.0, and more preferably at least 1.2, at least some of the (meth)acrylate present in the polymerizable material has two or more (meth)acryloyl groups per molecule. For example, the polymerizable material can contain a (meth)acrylate having two (meth)acryloyl groups per molecule or can contain a mixture of a (meth)acrylate having two (meth)acryloyl groups per molecule in combination with one or more (meth)acrylates having one (meth)acryloyl group per molecule. In another example, the polymerizable material can contain a (meth)acrylate having two or more (meth)acryloyl groups per molecule and a (meth)acrylate having three (meth)acryloyl groups per molecule, or the polymerizable material can contain a mixture of a (meth)acrylate having two or more (meth)acryloyl groups per molecule, a (meth)acrylate having three (meth)acryloyl groups per molecule in combination with one or more (meth)acrylates having one (meth)acryloyl group per molecule, two (meth)acryloyl groups per molecule, or a mixture thereof.

Specific examples of suitable polymerizable materials with one ethylenically unsaturated group per molecule include, but are not limited to, 2-hydroxyethyl (meth)acrylate, 2-hydroxypropyl (meth)acrylate, 3-hydroxypropyl (meth)acrylate, 4-hydroxybutyl (meth)acrylate, (meth)acrylonitrile, (meth)acrylamide, caprolactone (meth)acrylate, poly(alkylene oxide (meth)acrylate) (e.g., poly(ethylene oxide (meth)acrylate), poly(propylene oxide (meth)acrylate), and poly(ethylene oxide-co-propylene oxide (meth)acrylate)), alkoxy poly(alkylene oxide (meth)acrylate), (meth)acrylic acid, β-carboxyethyl (meth)acrylate, tetrahydrofurfuryl (meth)acrylate, N-vinyl pyrrolidone, N-vinylcaprolactam, N-alkyl(meth)acrylamide (e.g., N-methyl (meth)acrylamide), and N,N-dialkyl(meth)acrylamide (e.g., N,N-dimethyl(meth)acrylamide).

Suitable polymerizable materials with two ethylenically unsaturated groups per molecule include, for example, alkoxylated di(meth)acrylates. Examples of alkoxylated di(meth)acrylates include, but are not limited to, poly(alkylene oxide di(meth)acrylates) such as poly(ethylene oxide di(meth)acrylates) and poly(propylene oxide di(meth)acrylates); alkoxylated diol di(meth)acrylates such as ethoxylated butanediol di(meth)acrylates, propoxylated butanediol di(meth)acrylates, and ethoxylated hexanediol di(meth)acrylates; alkoxylated trimethylolpropane di(meth)acrylates such as ethoxylated trimethylolpropane di(meth)acrylate and propoxylated trimethylolpropane di(meth)acrylate; and alkoxylated pentaerythritol di(meth)acrylates such as ethoxylated pentaerythritol di(meth)acrylate and propoxylated pentaerythritol di(meth)acrylate.

Examples of suitable polymerizable materials with three ethylenically unsaturated groups per molecule include, for example, alkoxylated tri(meth)acrylates. Examples of alkoxylated tri(meth)acrylates include, but are not limited to, alkoxylated trimethylolpropane tri(meth)acrylates such as ethoxylated trimethylolpropane tri(meth)acrylates, propoxylated trimethylolpropane tri(meth)acrylates, and ethylene oxide/propylene oxide copolymer trimethylolpropane tri(meth)acrylates; and alkoxylated pentaerythritol tri(meth)acrylates such as ethoxylated pentaerythritol tri(meth)acrylates.

Suitable polymerizable materials with at least four ethylenically unsaturated groups per monomer include, for example, alkoxylated tetra(meth)acrylates and alkoxylated penta(meth)acrylates. Examples of alkoxylated tetra(meth)acrylates include alkoxylated pentaerythritol tetra(meth)acrylates such as ethoxylated pentaerythritol tetra(meth)acrylates.

In addition to the precursor composition containing a poly(alkylene oxide (meth)acrylate) having at least 2 (meth)acryloyl groups per molecule, the precursor composition can include other monomers that are added to impart certain characteristics to the hydrophilic gel material (e.g., a shaped polymeric material). In some instances, the precursor composition can contain an anionic monomer. As used herein, the term "anionic monomer" refers to a monomer that contains an ethylenically unsaturated group in addition to an acidic group selected from a carboxylic acid (i.e., carboxy) group (—COOH) or a salt thereof, a sulfonic acid group (—SO$_3$H) or a salt thereof, a sulfate group (—SO$_4$H) or a salt thereof, a phosphonic acid group (—PO$_3$H$_2$) or a salt thereof, a phosphate group (—OPO$_3$H) or a salt thereof, or a mixture thereof. Depending on the pH of the precursor composition, the anionic monomer can be in a neutral state (acidic form) or in the form of a salt (anionic form). The counterions of the anionic form are often selected from alkali metals, alkaline earth metals, ammonium ion, or an ammonium ion substituted with various alkyl groups such as a tetraalkylammonium ion.

Suitable anionic monomers having carboxy groups include, but are not limited to, acrylic acid, methacrylic acid, and various carboxyalkyl(meth)acrylates such as 2-carboxyethylacrylate, 2-carboxyethylmethacrylate, 3-carboxypropylacrylate, and 3-carboxypropylmethacrylate. Other suitable anionic monomers with carboxy groups include (meth)acryloylamino acids such as those described in U.S. Pat. No. 4,157,418 (Heilmann et al.). Exemplary (meth)acryloylamino acids include, but are not limited to, N-acryloylglycine, N-acryloylaspartic acid, N-acryloyl-β-alanine, and 2-acrylamidoglycolic acid. Suitable anionic monomers having sulfonic acid groups include, but are not limited to, various (meth)acrylamidosulfonic acids such as N-acrylamidomethanesulfonic acid, 2-acrylamidoethanesulfonic acid, 2-acrylamido-2-methylpropanesulfonic acid, and 2-methacrylamido-2-methylpropanesulfonic acid. Suitable anionic monomers having phosphonic acid groups include, but are not limited to, (meth)acrylamidoalkylphosphonic acids such as 2-acrylamidoethylphosphonic acid and 3-methacrylamidopropylphosphonic acid. Some suitable anionic monomers having phosphate groups include phosphates of alkylene glycol (meth)acrylates such as phosphates of ethylene glycol (meth)acrylate and phosphates of propylene glycol (meth)acrylate. Salts of any of these acidic monomers can also be used.

The anionic monomer, if present in a precursor composition, can affect the degree, the rate or combinations thereof, of the swelling of the hydrophilic gel material (e.g., shaped polymeric material). That is, the degree of swelling can often be altered by varying the amount of the anionic monomer as well as the amount of other hydrophilic monomer(s) in the precursor composition. The degree of swelling is usually proportional to the total amount of polar solvent that can be sorbed by the hydrophilic gel material. The amount of the anionic monomer is controlled so that the average number of ethylenically unsaturated groups per molecule of polymerizable material is at least 1.0, preferably greater than 1.0, and more preferably at least 1.2. The anionic monomer may be present in an amount ranging from 0 to less than 50 weight percent based on the total weight of the polymerizable material. The polymerizable material may contain at least 0 weight percent, at least 2 weight percent, at least 3 weight percent, or at least 5 weight percent anionic monomer. The polymerizable material may contain up to 50 weight percent, up to 25 weight percent, up to 15 weight percent, or up to 10 weight percent anionic monomer. The polymerizable material may contain 0 to 50 weight percent, 0 to 25 weight percent, 0 to 15 weight percent, or 0 to 10 weight percent anionic monomer. Some polymerizable materials do not contain an anionic monomer. Low levels or the complete absence of anionic monomer(s) may be found in precursor compositions containing certain biologically active agents. For example, certain cationic antimicrobial agents may be too tightly bound within the hydrophilic gel material to elute or diffuse from as desired in the presence of anionic monomers.

In some embodiments, the precursor composition may include a cationic monomer. As used herein, the term "cationic monomer" refers to a monomer having an ethylenically unsaturated group as well as an amino group, a salt of an amino group, or a mixture thereof. For example, the cationic monomer can be an amino (meth)acrylate or an amino (meth)acrylamide. The amino group can be a primary amino group or a salt thereof, a secondary amino group or a salt thereof, a tertiary amino group or a salt thereof, or a quaternary salt. The cationic monomers often include a tertiary amino group or a salt thereof or a quaternary amino salt. Depending on the pH of the precursor composition, some cationic monomer can be in a neutral state (basic form) or in the form of a salt (cationic form). The counterions of the cationic form are often selected from halides (e.g., bromides or chlorides), sulfates, alkylsulfates (e.g., methosulfate or ethosulfate), as well as various carboxylate anions (e.g., acetate).

Examples of some amino (meth)acrylates include N,N-dialkylaminoalkyl(meth)acrylates and N-alkylaminoalkyl (meth)acrylates such as, for example, N,N-dimethylaminoethylmethacrylate, N,N-dimethylaminoethylacrylate, N,N-diethylaminoethylmethacylate, N,N-diethylaminoethylacrylate, N,N-dimethylaminopropylmethacrylate, N,N-dimethylaminopropylacrylate, N-tert-butylaminopropylmethacrylate, and N-tert-butylaminopropylacrylate. Exemplary amino (meth)acrylamides include, for example, N-(3-aminopropyl)methacrylamide, N-(3-aminopropyl)acrylamide, N-[3-(dimethylamino)propyl]methacrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzoimidazolylpropyl)acrylamide, and N-(3-benzoimidazolylpropyl)methacrylamide.

Exemplary monomeric quaternary salts include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other exemplary monomeric quaternary amino salts include a dimethylalkylammonium group with the alkyl group having 2 to 22 carbon atoms or 2 to 20 carbon atoms. That is, the monomer includes a group of formula —N(CH$_3$)$_2$(C$_n$H$_{2n+1}$)$^+$ where n is an integer having a value of 2 to 22. Exemplary monomers include, but are not limited to monomers of the following formula

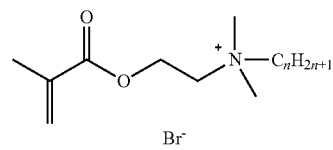

such that n is an integer in the range of 2 to 22. The synthesis of these monomers is described in U.S. Pat. No. 5,437,932 (Ali et al.).

Some cationic monomers, such as those having a quaternary amino group, can impart antimicrobial properties to the hydrophilic gel material. The cationic monomer is often present in an amount ranging from 0 to 50 weight percent based on the total weight of the polymerizable material. The polymerizable material may contain at least 0 weight percent, at least 1 weight percent, at least 2 weight percent, or at least 5 weight percent cationic monomer. The polymerizable material may contain up to 50 weight percent, up to 30 weight percent, up to 20 weight percent, up to 15 weight percent, or up to 10 weight percent cationic monomer. The polymerizable material may contain 0 to 50 weight percent, 1 to 30 weight percent, 2 to 20 weight percent, or 5 to 10 weight percent cationic monomer. Some polymerizable materials do not contain a cationic monomer.

Some exemplary polymerizable materials contain only nonionic monomers. That is, the polymerizable material is substantially free of both anionic monomers and cationic monomers. As used herein with reference to the anionic or cationic monomers, "substantially free" means that the polymerizable material contains less than 1 weight percent, less than 0.5 weight percent, less than 0.2 weight percent, or less than 0.1 weight percent anionic monomer or cationic monomer based on the total weight of the polymerizable material.

The precursor composition generally contains no greater than 90 weight percent polymerizable material based on the total weight of the precursor composition. For example, the precursor composition contains at least 10 weight percent, at least 20 weight percent, at least 25 weight percent, at least 30 weight percent, at least 40 weight percent, or at least 50 weight percent polymerizable material. The precursor composition contains no greater than 90 weight percent, no greater than 80 weight percent, no greater than 75 weight percent, no greater than 70 weight percent, or no greater than 60 weight percent polymerizable material. In some precursor compositions, the amount of polymerizable material is in the range of 10 to no greater than 90 weight percent, 20 to no greater than 90 weight percent, 30 to no greater than 90 weight percent, or 50 to no greater than 80 weight percent based on the total weight of the precursor composition.

In addition to the polar solvent and the polymerizable material, the precursor composition may include one or more optional additives such as processing agents, active agents, or mixtures thereof. Any of these optional additives can be dissolved or dispersed in the precursor composition.

The term "processing agent" refers to a compound or mixture of compounds that is added primarily to alter the physical or chemical characteristics of either the precursor composition or the hydrophilic gel material (e.g., shaped polymeric material). That is, the processing agent is added for the purpose of altering the precursor composition or facilitating the formation of the hydrophilic gel material. If added, the processing agent is typically added to the precursor composition. These processing agents are typically not considered to be active agents.

Suitable processing agents include, but are not limited to, rheology modifiers such as polymeric thickeners (such as gum, cellulose, pectin, and the like) or inorganic thickeners (such as clays, silica gels, and the like), surfactants that modify the surface tension, emulsifiers that stabilize the precursor composition, solubilizers that enhance the solubility of the polymerizable material in the polar solvent, initiators to facilitate polymerization of the polymerizable material, chain transfer or retarding agents, binders, dispersants, fixatives, foaming agents, flow aids, foam stabilizers, foam boosters, gellants, glossers, propellants, waxes, compounds to depress the freezing point and/or increase the boiling point of the precursor composition, and plasticizers.

The optional processing agent can be present in an amount no greater than 20 weight percent, no greater than 15 weight percent, no greater than 10 weight percent, no greater than 8 weight percent, no greater than 6 weight percent, no greater than 4 weight percent, no greater than 2 weight percent, no greater than 1 weight percent, or no greater than 0.5 weight percent based on the total weight of the precursor composition.

An initiator is a processing agent found in most precursor compositions for the free-radical polymerization reaction. The initiator can be a photoinitiator, a thermal initiator, or a redox couple. The initiator can be either soluble in the precursor composition or dispersed in the precursor composition.

An example of a suitable soluble photoinitiator is 2-hydroxy-1-[4-(2-hydroxyethoxyl)phenyl]-2-methyl-1-propanone, which is commercially available under the trade designation IRGACURE 2959 from Ciba Specialty Chemicals (Tarrytown, N.Y.). An example of a suitable dispersed photoinitiator is alpha, alpha-dimethoxy-alpha-phenylacetophenone, which is commercially available under the trade designation IRGACURE 651 from Ciba Specialty Chemicals. Other suitable photoinitiators are the acrylamidoacetyl photoinitiators, described in U.S. Pat. No. 5,506,279 (Babu et al.) that contain a polymerizable group as well as a group that can function as an initiator. The initiator is usually not a redox initiator as used in some polymerizable compositions known in the art. Such initiators could react with bioactive agents, if present.

Suitable thermal initiators include, for example, azo compounds, peroxides or hydroperoxides, persulfates, or the like. Exemplary azo compounds include 2,2'-azobis[2-(2-imidazolin-2-yl)propane]dihydrochloride, 2,2'-azobis(2-amidinopropane)dihydrochloride, and 4,4'-azobis-(4-cyanopentanoic acid). Examples of commercially available thermal azo compound initiators include materials available from DuPont Specialty Chemical (Wilmington, Del.) under the "VAZO" trade designation such as "VAZO 44", "VAZO 56", and "VAZO 68". Suitable peroxides and hydroperoxides include acetyl peroxide, t-butyl hydroperoxide, cumene hydroperoxide, and peroxyacetic acid. Suitable persulfates include, for example, sodium persulfate and ammonium persulfate.

In other examples, the free radical initiator is a redox couple such as ammonium or sodium persulfate and N,N,N',N'-tetramethyl-1,2-diaminoethane; ammonium or sodium persulfate and ferrous ammonium sulfate; hydrogen peroxide and ferrous ammonium sulfate; cumene hydroperoxide and N,N-dimethylaniline; or the like.

In some embodiments, the precursor composition includes only the polymerizable material, the polar solvent, and an initiator such as a photoinitiator. In most embodiments, the initiator is present in an amount no greater than 4 weight percent, no greater than 3 weight percent, no greater than 2 weight percent, no greater than 1 weight percent, or no greater than 0.5 weight percent based on the total weight of the polymerizable material in the precursor composition.

Optional Active Agents

The precursor compositions and/or hydrophilic gel materials of the present invention can include one or more optional active agents. The active agent provides some added functionality to the hydrophilic gel material (e.g., shaped polymeric material). The hydrophilic gel material functions as a carrier for the active agent. If present, the active agents are usually present in an amount no greater than 30 weight percent, no greater than 25 weight percent, no greater than 20 weight percent, no greater than 15 weight percent, no greater than 10 weight percent, or no greater than 5 weight percent based on the total weight of the precursor composition.

In some embodiments, the active agent can migrate into and out of the hydrophilic gel material (e.g., shaped polymeric material). In other embodiments, the active agent tends to be stationary and remain within the hydrophilic gel material. For example, the molecular size of the active agent may prevent elution or diffusion of the active agent out of the hydrophilic gel material. In another embodiment, the active agent may be attached to the hydrophilic gel material with a covalent or ionic bond. Active agents optionally can have one or more ethylenically unsaturated groups that can react with other ethylenically unsaturated groups to become part of the polymerizable material or to become attached to the polymeric material of the hydrophilic gel material.

Some active agents are biologically active agents. As used herein, the terms "biologically active agent," "biological active," and "bioactive agent" are used interchangeably and refer to a compound or mixture of compounds that has some known effect on living systems such as, for example, a bacteria or other microorganisms, plant, fish, insect, or mammal. The bioactive agent is added for the purpose of affecting the living system such as affecting the metabolism of the living system.

Examples of bioactive agents include, but are not limited to, medicaments, herbicides, insecticides, antimicrobial agents, disinfectants and antiseptic agents, local anesthetics, astringents, antifungal agents, antibacterial agents, growth factors, vitamins, herbal extracts, antioxidants, steroids or other anti-inflammatory agents, compounds that promote wound healing, vasodilators, exfoliants such as alpha-hydroxy acids or beta-hydroxy acids, enzymes, nutrients, proteins, and carbohydrates. Still other bioactive agents include artificial tanning agents, tanning accelerants, skin soothing agents, skin tightening agents, anti-wrinkle agents, skin repair agents, sebum inhibiting agents, sebum stimulators, protease inhibitors, anti-itch ingredients, agents for inhibiting hair growth, agents for accelerating hair growth, skin sensates, anti-acne treatments, depilating agents, hair removers, corn removers, callus removers, wart removers, sunscreen agents, insect repellants, deodorants and antiperspirants, hair colorants, bleaching agents, and anti-dandruff agents. Any other suitable bioactive agent known in the art can be used.

Examples of suitable bioactive agents include metal-containing compounds (e.g., silver-containing compounds, zinc-containing compounds, copper-containing compounds, gold-containing compounds, and platinum-containing compounds), fatty acid monoesters, polyhexamethylenebiguanide, chlorhexidine, triclosan, peroxides, iodines and complexes thereof (e.g., iodophores), derivatives thereof, and combinations thereof. Additional biological actives that are suitable for use with the present invention include medicinal ingredients disclosed in Cantor et al., U.S. Pat. Appl. Pub. No. US2003/0054025 A1.

The silver-containing compounds suitable for the bioactive agent include compounds that are soluble in aqueous solvents (e.g., silver nitrate) and sparingly soluble silver-containing (SSSC) compounds, as described in U.S. Pat. Appl. Pub. Nos. 2006/0035039 and 2006/034899. The silver-containing compounds suitable for the bioactive agent provide antimicrobial activity by a sustained release of silver ions from the hydrophilic gel materials when in contact with moist environments, such as a wound bed. Examples of suitable silver-containing compounds include silver oxide, silver sulfate, silver acetate, silver chloride, silver lactate, silver phosphate, silver stearate, silver thiocyanate, silver proteinate, silver carbonate, silver nitrate, silver sulfadiazine, silver alginate, and combinations thereof. Examples of particularly suitable silver-containing compounds include silver oxides, silver carbonates, and silver acetates. Examples of suitable concentrations of the silver-containing compound range from 0.1 wt-% to 15.0 wt-%, based on the total weight of the precursor composition.

Fatty acid monoesters suitable for the biological active are desirably considered food grade and recognized as safe (GRAS) by the U.S. Food and Drug Administration (FDA). Such fatty acid monoesters may be derived from $C_8$ to $C_{12}$ fatty acids such as glycerol monoesters of caprylic acid, capric acid, and lauric acid; propylene glycol monoesters of caprylic acid, capric acid, and lauric acid; fatty acids; and combinations thereof. Examples of suitable fatty acid monoesters include glycerol monolaurate commercially available under the trade designation "LAURICIDIN" from Med-Chem Laboratories, East Lansing, Mich.; glycerol monocaprylate commercially available under the trade designation "POEM M-100" from Riken Vitamin Ltd., Tokyo, Japan; glycerol monocaprate commercially available under the trade designation "POEM M-200" from Riken Vitamin Ltd.; propylene glycol monolaurate, propylene glycol monocaprylate, and propylene glycol monocaprate, all commercially available from Uniquema International, Chicago, Ill.; and combinations thereof. Examples of suitable concentrations of the fatty acid monoester in the precursor composition range from 1.0 wt-% to 30.0 wt-%, based on the total weight of the precursor composition.

Examples of suitable chlorhexidine materials for the bioactive agent include chlorhexidine, chlorhexidine salt derivatives such as chlorhexidine digluconate (typically referred to as chlorhexidine gluconate or CHG) and chlorhexidine acetate, and combinations thereof. Examples of suitable concentrations of the chlorhexidine materials in the precursor composition range from 1.0 wt-% to 40.0 wt-%, based on the total weight of the precursor composition. Examples of particularly suitable concentrations of the chlorhexidine materials in the precursor composition range from 5.0 wt-% to 20.0 wt-%, based on the total weight of the precursor composition.

Enhancers may be used to increase the biological activity of certain biological active agents (e.g., fatty acid monoesters, fatty acids, and halogenated phenolic compounds such as triclosan). Examples of suitable enhancers include chelating agents such as ethylenediaminetetraacetic acid (EDTA) and salts thereof; organic acids such as lactic acid, tartaric acid, adipic acid, succinic acid, citric acid, ascorbic acid, malic acid, mandelic acid, acetic acid, sorbic acid, benzoic acid, and salicylic acid; alcohols such as ethanol, isopropanol, and long chain alcohols, such as octyl alcohol and decyl alcohol; and combinations thereof. Examples of suitable concentrations of the enhancers in the fluid solution range from 1.0 wt-% to 20.0 wt-%, based on the total weight of the precursor composition.

The concentration of the bioactive agent in the precursor composition desirably is such that the concentration of the bioactive agent is therapeutically effective. As such, the concentration of the bioactive agent in the precursor composition will vary depending on a variety of factors, such as the type of biological active used, the design of the article, the condition to be treated, and the length of time the article will be used. Generally the concentration of the bioactive agent in the precursor composition ranges from 0.01 wt-% to 50.0 wt-%, based on the total weight of the precursor composition Other active agents suitable for use in the present invention are not biologically active. These active agents are added to provide some non-biological functionality to the hydrophilic gel material. That is, these active agents are not added for the purpose of affecting a living system such as affecting the metabolism of the living system. Suitable active agents, for example, can be selected to alter the odor, charge, color, density, pH, osmolarity, water activity, ionic strength, or refractive index of the hydrophilic gel material. The active agent can also be selected to provide a reactive group or compound. Examples of non-biologically active agents include emulsifiers or surfactants (including anionic surfactants, cationic surfactants, zwitterionic surfactants, non-ionic surfactants, and combinations thereof), pigments, inorganic oxides (such as silicon dioxide, titania, alumina, and zirconia), fragrances such as aromatherapy agents and perfumes, odor absorbing agents, humectants, lubricants, dyes, bleaching or coloring agents, flavorings, decorative agents such as glitter, emollients, acids, bases, buffers, indicators, soluble salts, chelating agents, and the like. Some humectants that are liquids at room temperature that are miscible with water (e.g., glycols and other polyols) in the amounts used are considered to be part of the polar solvent when the precursor composition of the swollen hydrophilic gel material or dried hydrophilic gel material is calculated.

In some embodiments, the active agent is an indicator. Any suitable chemistry can be used for the indicator. The indicator can detect, for example, a specific pH range or the presence of a specific class of compounds. The presence of some specific classes of compounds can result in a color change. Ninhydrin, for example, can be used to detect the presence of a protein or amino group. The indicator can also be a typical pH indicator such as methyl blue or phenolphthalein.

Inorganic oxide nanoparticles can be added to the hydrophilic gel material to increase the refractive index of the hydrophilic gel material. For example, the hydrophilic gel material can be loaded with zirconia nanoparticles or titania nanoparticles. Zirconia nanoparticles can be prepared using the methods described, for example, in U.S. Pat. No. 6,376, 590 (Kolb et al.) and U.S. Pat. Appl. Pub. No. 2006/0148950A1 (Davidson et al.).

Any of the active agents may have a polymerizable group. The use of a polymerizable group on the active agent can be used to prevent the migration of the active agent out of the hydrophilic gel material. Cationic monomers having an ethylenically unsaturated group as well as a quaternary amino group may function as an antimicrobial agent and can be included in the polymerizable material of the precursor composition. The cationic monomer is often a (meth)acrylate having a quaternary amino group.

Because the hydrophilic gel material (e.g., shaped polymeric material) typically has unreacted polymerizable groups, the hydrophilic gel material can be reacted post-formation with active agents having polymerizable groups. For example, a cationic monomer having an ethylenically unsaturated group and a quaternary amino group can be reacted with the hydrophilic gel material having unreacted ethylenically unsaturated groups. A mixture containing the polymerizable material, the cationic monomer, and a photoinitiator can be exposed to actinic radiation to react the ethylenically unsaturated group of the cationic monomer with an unreacted ethylenically unsaturated group of the polymerizable material. The reaction product is a hydrophilic gel material with attached quaternary amino groups.

Active agents can be present in the precursor composition used to prepare the swollen hydrophilic gel material. Alternatively, the swollen hydrophilic gel materials can be dried and swollen a second time with a sorbate. That is, the dried hydrophilic gel material can sorb the sorbate to form a second swollen hydrophilic gel material (e.g., a second swollen shaped polymeric material). The sorbate often includes an active agent. The active agent can be a biologically active agent, a non-biologically active agent, or a mixture thereof. Suitable active agents are described herein.

When included in the precursor composition, the active agents are preferably stable and/or resistant to the radiation used to polymerize the material. The amount of radiation and length of exposure may also be adjusted to prevent the degradation of the active agent when added to the precursor composition prior to curing. Alternatively, active agents that are not stable or resistant to radiation may fare better if added after formation of the hydrophilic gel material (e.g., the shaped polymeric material can be dried and then exposed to a sorbate that includes the active agent). Unlike the active agents that often can be added to either to the precursor composition or after formation of the hydrophilic gel material (e.g., shaped polymeric material), the processing agents are typically included in the precursor composition prior to cure.

The amount of the active agent can be in the range of 0 to no greater than 70 weight percent based on the weight of the swollen hydrophilic gel material. In some exemplary swollen hydrophilic gel materials, the amount of the active agent is no greater than 50 weight percent, no greater than 40 weight percent, no greater than 30 weight percent, no greater than 20 weight percent, no greater than 10 weight percent, no greater than 5 weight percent, no greater than 2.5 weight percent, or no greater than 1 weight percent of the swollen hydrophilic gel materials.

Shaped Materials

Figure 2:
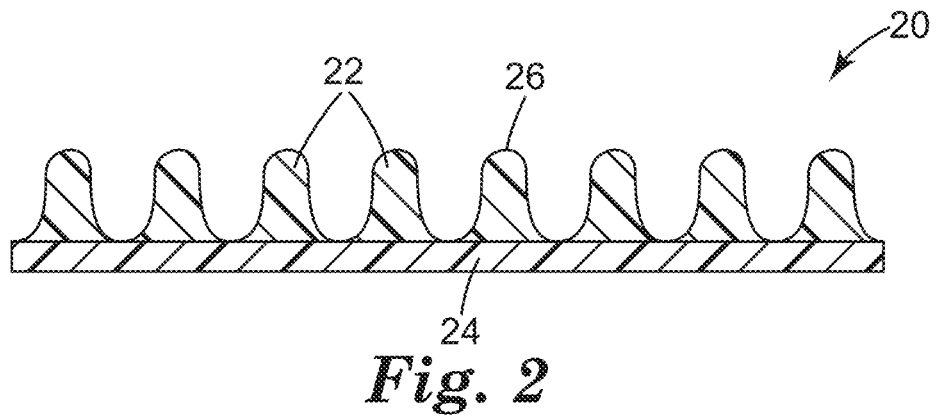
FIG. 2 is a cross-section of another exemplary article according to the present invention.

FIG. 1 and FIG. 2 illustrate a swollen shaped hydrophilic gel material formed according to the present invention. The swollen shaped polymeric material contains the inverse topography of a mold having at least two separate wells (such as that represented in FIG. 3).

FIG. 1 shows a cross-section of one embodiment of a hydrophilic gel layer of the invention. Article 10 comprises a hydrophilic gel material 12 and a backing layer 14. The hydrophilic gel material 12 is cured in an overfilled mold to form an integral continuous layer of shapes 16. The continuous layer of hydrophilic gel material 12 is attached to backing layer 14 by any suitable means, such as by laminating the layers together or be means of an adhesive layer (not shown).

FIG. 2 shows an alternative embodiment of a hydrophilic article of the invention. Article 20 comprises a hydrophilic gel material 22 that forms shapes 26 attached to backing layer 24 in a discontinuous coating on backing layer 24. The shapes 26 may be laminated to backing layer 24 as part of the mold and cure process, or the shapes 26 may be formed as discrete shapes 26 and attached to backing layer 24 by any suitable attachment, such as an adhesive. This embodiment results when the wells of the mold are not overfilled with precursor composition.

The shaped hydrophilic gel materials may be rigid or elastomeric and may or may not be easily crushed (e.g., friable). A higher content of polymeric material tends to increase the modulus and crush strength of the shaped polymeric material. A greater amount of crosslinking achieved by using a precursor composition with a higher average functionality also tends to increase the modulus and crush strength of the shaped hydrophilic gel materials. The average functionality refers to the average number of polymerizable groups (ethylenically unsaturated groups) per molecule.

The shaped hydrophilic gel materials can have a wide variety of sizes. The dimensions of the shaped hydrophilic gel materials depends on the at lease two separate wells (including the features on the surfaces of the wells) within the mold used to generate the shapes of the precursor composition prior to radiation curing, and can range from less than one micrometer to several thousand micrometers. Particularly suitable dimensions, such as the height or depth of the shaped hydrophilic gel materials are in the range of 0.5 to 5000 micrometers, in the range of 1 to 1000 micrometers, in the range of 10 to 1000 micrometers, or in the range of 100 to 1000 micrometers. The length or widths of the shaped hydrophilic gel materials are in the range of 0.5 to 5000 micrometers, in the range of 1 to 1000 micrometers, or in the range of 100 to 1000 micrometers.

After exposing the precursor composition to radiation, the polymerizable material is at least partially polymerized to form a first swollen shaped hydrophilic gel material. The first swollen shaped hydrophilic gel material (disposed on a substrate) can be removed form the mold. The swollen shaped polymeric material generally has the dimensions of the well of the mold. Conventionally, the shaped hydrophilic gel material (disposed on a substrate) can be removed from the mold by gravity, vibratory techniques, or by simply pulling the substrate with the shaped hydrogel material adhered thereto out of the mold.

The swollen shaped hydrophilic gel materials are generally homogeneous and do not contain discernible features other than those made discernible by the mold. Development of channels or features on the swollen shaped hydrophilic gel materials may result from surface structures within a well.

In certain embodiments, the precursor composition may fill less than 100% of the volume of the wells or may fill an excess of 100 percent of the wells. The precursor composition may then be at least partially solidified by exposing the precursor composition to radiation as described herein. The exposure to radiation may occur, at least in part, through the substrate. Following such exposure, the resulting article may be removed from the mold and exposed to additional radiation. Optionally, partially solidified shaped hydrophilic gel materials may be attached to a substrate following their exposure to radiation through a variety of means including for example through the use of an adhesive.

Molds and Methods of Making Shaped Materials

The shaped polymeric material can be formed in a mold having at least two wells. A mold is provided to define the size and shape of the shaped polymeric material. A precursor composition is added and retained within the wells of the mold. The precursor composition is then exposed to radiation to at least partially polymerize the polymerizable material. The partially polymerized material within the wells forms a first swollen shaped hydrophilic gel material.

A mold may be a film, a sheet, a web, a belt, a roller, a drum, a ribbon, discrete particles or other three dimensional shapes or structures, or combinations thereof for which a flowable or partially flowable material, such as a precursor composition, can be applied. The mold can be formed from a polymeric material, a metallic material, a ceramic material, or a combination thereof. The material selected for the mold generally has properties suitable for a particular application. Some properties to consider in forming a mold include physical, chemical, optical, electrical, release, and thermal properties.

A mold may be transparent to the radiation used to polymerize the precursor composition such that the precursor composition can be at least partially polymerized through the mold. In another embodiment, the mold can be opaque to the radiation used to polymerize the precursor composition. In such embodiment, exposing the precursor composition to radiation can occur through the substrate. In certain embodiments, for "transparent" molds and substrates, exposing the precursor composition to radiation can occur through either or both the mold and substrate.

A mold can be made of a material that allows easy release of the polymerized hydrophilic gel material. For example, by being made of thermoplastic resin, the mold can have a low-energy surface that affords good release from a polymeric gel. Good release is assured when there is a significant difference in surface energy between the surfaces of the mold and the polymeric gel, the latter typically being 40-41 dynes/cm. Because the surface energy of each of polypropylene and polyethylene is 30-31 dynes/cm, these afford easy separation of the polymeric gel. Certain mold materials, such as poly(vinylchloride) and cellulose acetate butyrate, may require the use a release agent. Polyolefins are more transparent to and stable towards ultraviolet radiation than are poly(vinylchloride) and cellulose acetate butyrate.

A mold can be formed having features on its surfaces. These features can be transferred from the mold to a flowable or partially flowable material applied or coated onto the mold. The surfaces of the mold may be smooth, partially smooth, textured, or a combination thereof. Examples of textured or structured surfaces comprising nano-, micro-, and macro-replicated features and patterns are described in U.S. Pat. No. 6,649,249 (Engle et al.) and U.S. Pat. No. 7,105,809 (Wood et al.). The mold may further include structured surfaces having regular or random features spatially located throughout the surface.

Molds further include features commonly known as wells. Wells may be referred to as cavities, regions, pockets, ridges, channels, and the like. The well provides a location on a surface for retaining a flowable or partially flowable material. Wells generally have volumes with dimensions such as diameter, radius, height, width, and length. The material in the wells can be retained by walls and/or other features located on or within the mold. In one embodiment, the wells can be located within a structured surface of a mold. The wells of the mold can be located separately from each other with a land (e.g., region) separating the wells.

Wells may have different shapes. Examples of shapes of the wells may include conical, cubic, triangular, rectangular, pyramidal, and other shapes suitable for retaining a volume of a material. The base of the well refers to a location within the well generally spaced a distance from the top of the well. The top of the well may refer to a land or a surface to distinguish individual wells from one another. In a mold having at least two wells, a first well may have the same shape as a second well. In another mold, the first well may have a different shape than the second well.

Similarly, the wells can have random or precisely spaced features positioned on the walls of the well, on the land areas, and within the wells. Some of these features may include protrusions and depressions. These features are commonly referred to as topographical features.

Some examples of topographical features of wells range from the extreme of cubic wells with parallel vertical, planar walls to the extreme of hemispherical wells, with any possible solid geometrical configuration of walls between those extremes. Other example topographies or topographical features include conical wells with angular, planar walls, truncated pyramid wells with angular, planar walls, and cube corner shaped wells.

Some of the topographical features in the wells, or defining the shapes of the wells themselves may be formed on a nano-, micro-, or macro-scale. Similarly, some of the topographical features may be found on the mold or at least on the land areas between the wells. The dimensions of these features may be limited to the tooling or equipment for manufacturing the features. Generally, a mold having a microstructured surface, for example, may have a desired topography on at least one surface. These microstructures include a configuration of features such that at least two dimensions of the features are microscopic. Microscopic features are sufficiently small so as to require an optic aid to the naked eye to determine their shape. The dimensions of the topographical features range from two hundred microns or less in at least two or the three possible dimensions (in/out of the plane of the mold, and in each direction along the plane of the mold). The topographical features have a desired characteristic size (such as length measured along any dimension) and feature density (features per unit area of mold surface). A feature, as described earlier can be anything that represents a departure or deviation from a flat planar surface. Some of the features can include those that protrude (nodules, posts, lumps, ridges), or those which are recessed (hoes, pits, fissures, crevices). Microstructured surfaces may also possess a combination of protruding and recessed features (e.g., furrows and ridges, protruding and recessed pyramids). In the case of ridges, furrows, or intersecting planes, a feature may be a corner or linear intersection of such ridges, furrows, or planes.

A feature may be such that its characteristic length is in all three dimensions (i.e., into and out of the plane of the film, and in each orthogonal direction along the plane of the film is similar). Conversely, a feature may be such that the characteristic length in one or more directions is somewhat longer, or even much longer, than in the other directions (i.e., in the case of features such as ridges or furrows).

Figure 3:
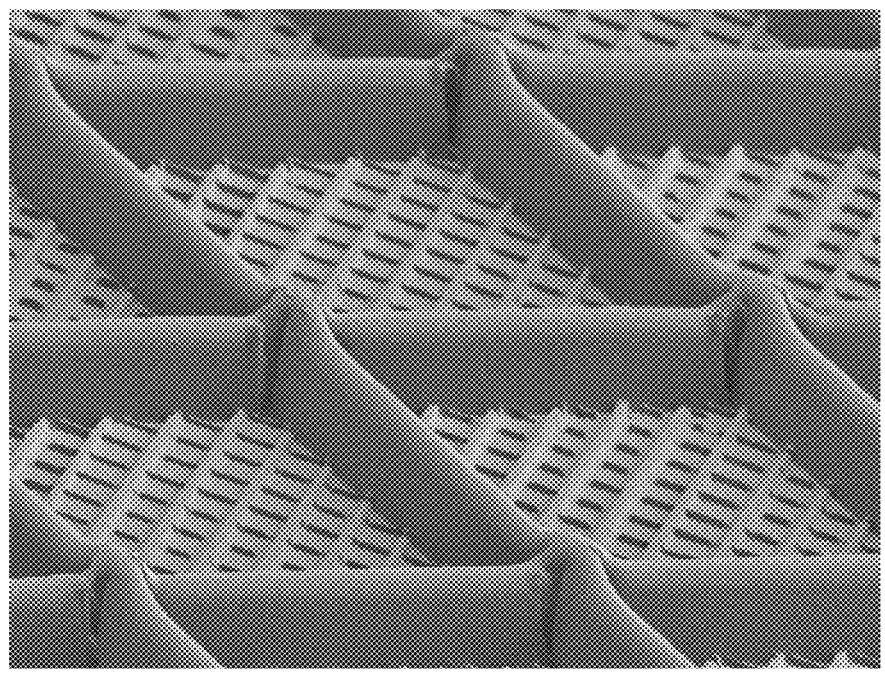
FIG. 3 is an optical micrograph of a mold having at least two wells.

In some embodiments, the microstructured features include those possessing a maximum characteristic length in one or more directions of two hundred microns. In some embodiments, the maximum characteristic length is fifty microns, and in another embodiment, the characteristic length is less than 10 microns. In some embodiments, the minimum characteristic length in one or more directions is one nanometer. In other, the minimum characteristic length is ten nanometers, and in another embodiment the minimum characteristic length is one hundred nanometers. Also, in some embodiments, microstructured feature densities in a mold can be in a range of 100 features or greater per square millimeter (mm$^2$). In some embodiments, the mold may have a density of greater than 1,000 features or greater per square millimeter (mm), and in other embodiments, a density of greater of than 10,000 features or greater per square mm. FIG. 3 illustrates a mold having at least two separate wells, and features located within the wells.

Some features may be present on a regular repeating basis, or they may be random. The features may be present over the entire area of the mold, or they may be present only in areas such as the wells or optionally on the land areas, in which the flowable or partially flowable material is to be deposited.

In some embodiments, the wells are formed with the substrate positioned against the mold. Any suitable materials can be used for the substrate so long as the material is sufficiently porous, or otherwise retains a structural shape that allows the substrate to form a well when positioned against the mold when the mold does not consist of defined wells (e.g., as with a scrim).

In one embodiment, a porous substrate (or membrane) can be used as the substrate positioned on the mold to form a well for receiving the precursor composition. Suitable porous substrate may be selected from any which is coatable, and comprises openings or pores. Suitable porous substrates include, but are not limited to, porous membranes, porous nonwoven webs, and porous fibers. The porous substrate may be formed from a variety of materials, such as a polymeric membrane, a plastic mesh, a fiberglass matte or a metal screen, for example, as described below in the section entitled SUBSTRATES.

In one embodiment, the porous substrate has an average pore size less than 10 micrometers. In some embodiments, the average pore size of the porous substrate is greater than 10 nanometers. Suitable porous substrates include, but are not limited to, nanoporous membranes, microporous membranes, microporous nonwoven webs, and microporous fibers. In some embodiments, the porous substrate may have a combination of different pore sizes (e.g., micropores and nanopores).

In some embodiments, the porous substrate is hydrophobic and comprises one or more of the polymeric materials described below in the section entitled SUBSTRATES.

In some embodiments, the porous substrate is a hydrophilic porous membrane such as a thermally-induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. TIPS membranes are disclosed in U.S. Pat. No. 1,529,256 (Kelley); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and 5,962,544 (Waller, Jr.). In some embodiments, TIPS membranes comprise polymeric materials such as poly(vinylidene fluoride) (i.e., PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. TIPS membranes comprising PVDF are further described in U.S. Pat. App. Pub. No. 2005/0058821 (Smith et al.).

In some embodiments, the porous substrate is a nonwoven web. The average pore size is typically greater than 25 micrometers. Melt-blown microfiber nonwoven webs are described using methods and equipments similar to those in Wente, V. A., "Superfine Thermoplastic Fibers"; *Industrial Engineering Chemistry*, 48, 1342-1346 (1956), and Wente, V. A., "Manufacture of Super Fine Organic Fibers"; *Naval Research Laboratories* (Report No. 4364), May 25, 1954. For example, the non-woven web can be prepared from ethylene-vinyl alcohol copolymers as described in U.S. Pat. No. 5,962,544 (Waller, Jr.). In one embodiment, the non-woven web can be prepared from nylon.

Suitable porous substrates include commercially available materials such as hydrophilic and hydrophobic microporous membranes known under the trade designations DURAPORE and MILLIPORE EXPRESS MEMBRANE, available from Millipore Corporation of Billerica, Mass. Other suitable commercial microporous membranes known under the trade designations NYLAFLO and SUPOR are available from Pall Corporation of East Hills, N.Y.

In one embodiment, a non-woven scrim can be used as the substrate. The nonwoven scrim may be positioned against a surface, such as a film, and the nonwoven scrim may be impregnated with the precursor composition. The precursor composition may then be at least partially cured as described herein.

For preferred medical articles, the shapes of the shaped hydrophilic gel may be any shape imparted by the mold that aids in the desired properties of the medical article such as delivery of the actives, increased surface for absorption, and/or enhanced gel layer integrity upon hydration. For such embodiments, the shapes include, but are not limited to, ridges, channels, mounds, peaks, hemispheres, pyramids, cylinders, cones, blocks, and truncated variations and combinations thereof.

At least two separate wells of the mold can be used to retain a flowable or partially flowable material such as a precursor composition. The precursor composition is generally a liquid composition consisting of curable, polymerizable or crosslinkable molecules, which are cured while in contact with the mold. The precursor composition generally has a viscosity sufficient for flowing and adding the composition into the at least two separate wells of the mold.

Preferably, a precursor composition has a viscosity generally less than 5,000 centipoise (cps). Above that range, air bubbles may be entrapped and the precursor may not completely fill the pattern of the mold. However, inexact replication of the mold pattern is normally acceptable, and minor blemishes, entrapped air bubbles or fractures in the hydrophilic gel layer will still be useful.

The precursor composition can be positioned in at least a portion of at least two separate wells of the mold by different methods. Some of the positioning or addition methods include, but are not limited to, gravity filling, pressure filling, or vacuum filling. In one example, the precursor composition may be positioned in at least a portion of the wells by capillary action. The precursor composition may be positioned in at least a portion of the wells, such that the precursor composition is positioned in at least 5 percent of the volume of the at least two separate wells. In some embodiments, the precursor composition may be positioned in at least 15 percent, in at least 25 percent, or at least 35 percent of the volume of the at least two separate wells. The precursor composition may be positioned up to 100 percent, up to 90 percent, up to 80 percent, or up to 70 percent of the volume of the at least two separate wells. The precursor composition may be positioned in at least a portion of the at least two separate wells in a range of 5 to 100 percent, 15 to 90 percent, 25 to 80 percent, or 35 to 70 percent of the volume of the at least two separate wells.

In some embodiments, the precursor composition may be positioned to fill in excess of 100 percent of the volume of the at least two separate wells. At this volume, the precursor composition may occupy the land areas between the wells providing for connection between the two separate wells. The shaped polymeric material may be in the form of a film or sheet having the polymerizable material of the wells attached to the film or sheet, and further disposed on a substrate.

In particularly preferred embodiments, particularly medical articles, it is preferred that the shaped hydrophilic gel layer, in both single layer and multilayer formats, have a void volume of 10-90%, and preferably a void volume of 15-80%. Knowing the calipered thickness of a particular gel absorbent layer, the percentage of the apparent volume, which constitutes voids, can readily be calculated. The caliper of the gel may be measured with a conventional thickness gauge in which a pair of opposed feet respectively contacts the smooth surface of the hydrophilic gel layer and several of the highest points of the shaped hydrogel projecting from the surface in a plane tangential to the highest points of the shapes projecting from the surface. The apparent volume of a unit area of gel layer is calculated as the product of area and calipered thickness. The calipered thickness of the gel layer is, of course, greater than the thickness of a gel layer having the same volume of polymer but with two smooth parallel faces.

After positioning the precursor composition in the wells of the mold, it may be at least partially solidified by exposing the precursor composition to radiation within the two separate wells. The radiation at least partially polymerizes the polymerizable material, which has an average number of ethylenically unsaturated groups per molecule equal to at least 1.0, preferably greater than 1.0, and more preferably at least 1.2. The polymerizable material polymerizes by a free-radical polymerization process.

The polymerized material assumes the shape and features within the two separate wells of the mold. Most of the features within the wells or on the microstructured surface of the mold will be the negative image of the features designed or displayed on a shaped polymeric material. For example, ridges having wells on the surface of the mold will manifest as channels on a surface of the shaped polymeric material.

Figure 5:
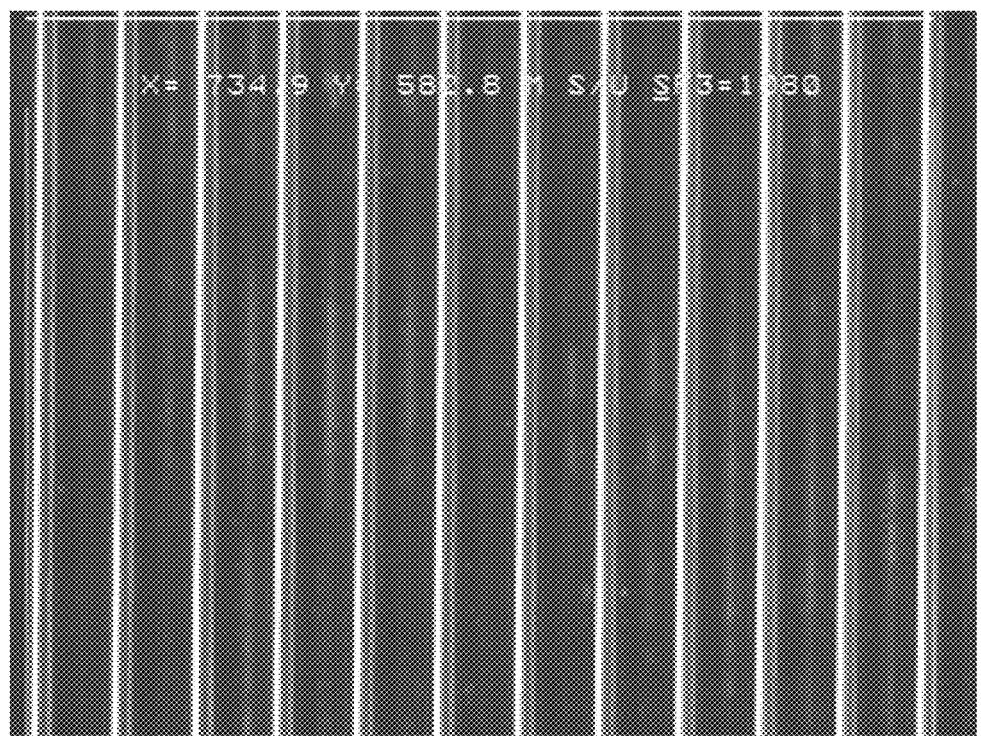
FIG. 5 is an optical micrograph of a metal tool used to form a shaped hydrophilic gel material.
Figure 6:
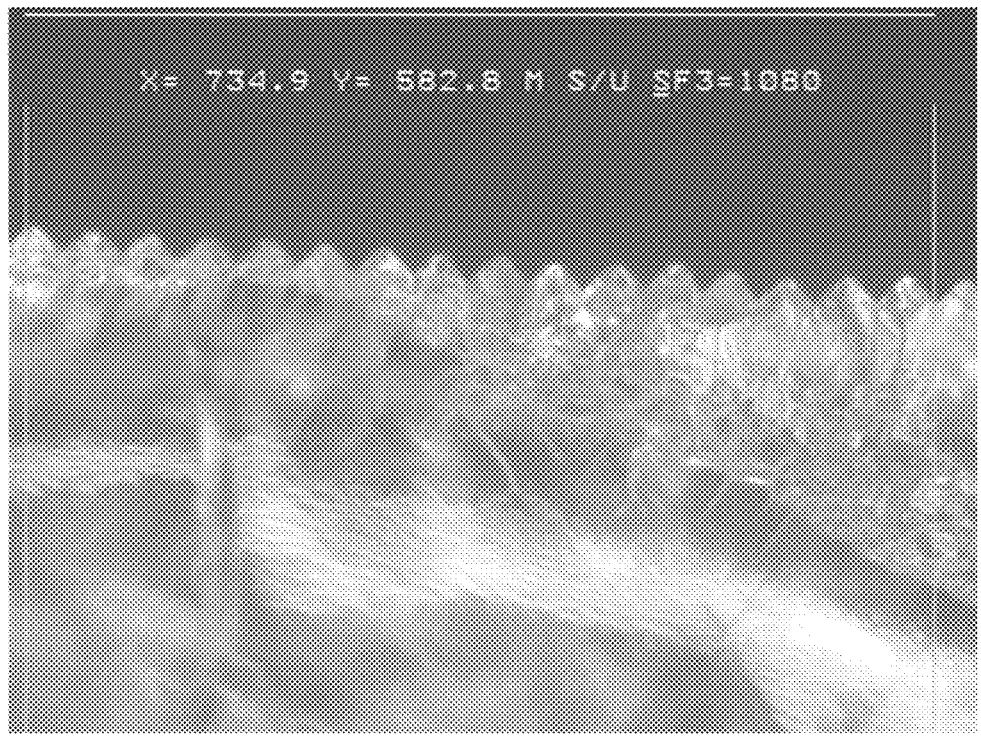
FIG. 6 is an optical micrograph of a cross-section of a shaped hydrophilic gel material.

In an exemplary embodiment, a precursor composition can be poured onto a metal tool having a raised 90 degree prismatic pattern at 60 micrometer spacing as shown in FIG. 5. A substrate can be placed over and in contact with the precursor composition and the metal tool surface. After at least partial polymerization of the polymerizable material, the composite structure of the hydrogel can be removed from the metal tool forming a hydrogel having an inverse shape of the wells replicated on the surface opposite the substrate. The shaped hydrophilic gel materials can be adjoined by a land if the wells are overfilled. FIG. 6 illustrates formation of the shaped hydrophilic gel materials adjacent to one another connected by land areas, which is disposed on a substrate (although substrate not shown in FIG. 6).

Non-Contact Deposition and Other Coating Methods

The precursor composition can be applied as a coating on a substrate using a variety of methods. Such methods include, both contact methods, for example, roll coating, knife coating, gravure coating, pattern coating, offset gravure coating, wire-wound rod coating, kiss coating, and non-contact deposition methods such as inkjet printing, spray atomization deposition, electrostatic deposition, microdispensing, condensation deposition, evaporative deposition, curtain coating, and mesoscale deposition and other coating methods known to those skilled in the art. The coating can be continuous or discontinuous, regardless of whether contact or non-contact coating methods are used. In certain embodiments, non-contact deposition methods are used to form discontinuous coatings.

Figure 4:
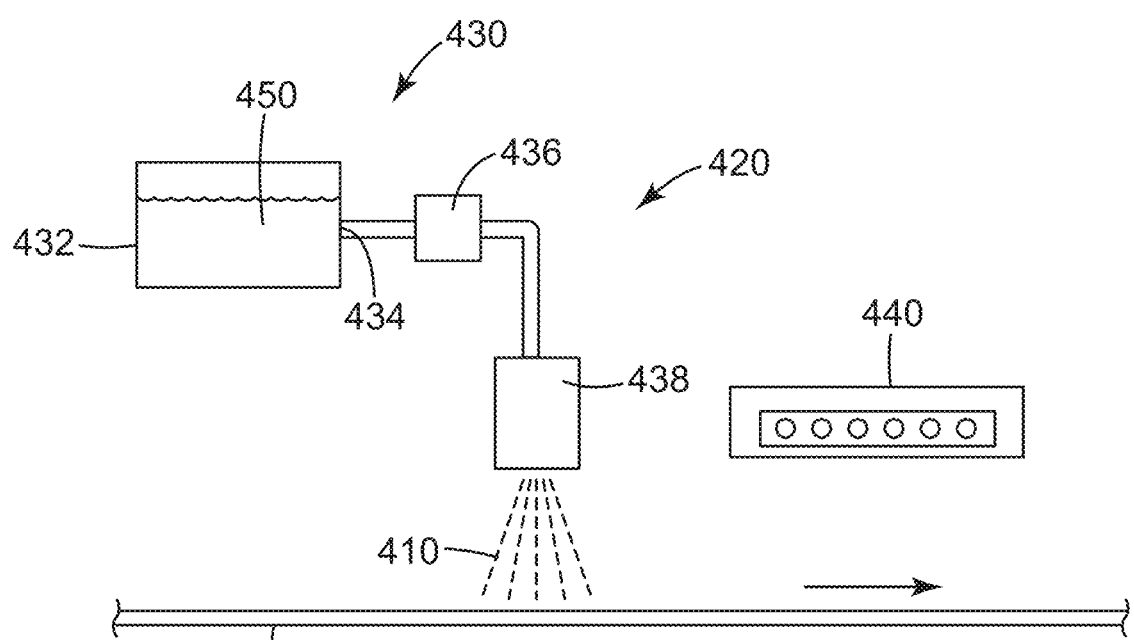
FIG. 4 is a schematic diagram of an exemplary embodiment of a process and equipment for making the hydrophilic gel material on a substrate.

The precursor composition can be applied in a discontinuous coating on a substrate by non-contact deposition. FIG. 4 is a schematic representation of one exemplary non-contact deposition process for making a substrate with a discontinuous coating of hydrophilic gel materials. Process 420 includes a feed system 430 and a curing system 440. Precursor composition 450 passes through feed system 430, optionally through a pump 436, and is deposited by a non-contact deposition device 438, such as an ultrasonic atomizer. The output 410 of the non-contact deposition device 438 is deposited on a substrate 405. The curing system 40 provides radiation such that the output 410 on a substrate 405 is exposed to radiation and undergoes a polymerization reaction to form cured material.

Each of feed system 430 and curing system 440 of process 420 can include various elements. Feed system 430 includes a reservoir 432 having an outlet 434. Reservoir 432 may be a pot, vessel, hopper, hose, funnel, or other element into which a volume of the precursor composition 450 can be poured or otherwise added. Reservoir 432 may be metal, plastic, glass, or any other suitable material; preferably, precursor composition 450 does not interact with reservoir 432. Outlet 434 may be as simple as an aperture or hole in reservoir 432, or may be a separate element. In the embodiment shown in FIG. 4, outlet 434 is merely an aperture in receiver 432.

Curing system 440 may include a radiation source and a shielding device. The shielding device is often present to direct the radiation from the source to the desired location and to protect persons or equipment that may be in close proximity. The shielding device may also provide environmental control around the curing process.

As depicted in FIG. 4, a method of the present invention involves providing a precursor composition 450 that may optionally contain one or more bioactive agents. The precursor composition 450 is applied to the substrate 405 by non-contact deposition, and is exposed to radiation to at least partially polymerize the polymerizable material. When the precursor composition contains a bioactive agent, the method of application and curing will be such that the biological active remains active on or near the surface of the substrate 405. Optionally the biological active may be added after curing by resorbing the biological active into the dried hydrophilic gel material.

The precursor composition 450 of the present invention may include a variety of different biological actives, such as antimicrobials, antibiotics, antifungals, antivirals, and antiseptics (discussed in further detail below). The hydrophilic gel material may incorporate low concentrations of the biological active, while still exhibiting effective levels of antimicrobial activity, as measured by the Zone of Inhibition Test described below.

Non-contact deposition techniques suitable for the present invention are generally independent of the surface being coated. As such, a non-contact deposition mechanism may be moved in a transverse direction to the surface 405 being coated, while imparting substantially no transverse force to the surface 405. In contrast to contact coating techniques, non-contact deposition allows the same processing equipment to be used for coating a variety of different surfaces without requiring changes in formulations or process parameters. Examples of suitable non-contact deposition techniques include inkjet printing, spray atomization deposition, electrostatic deposition, microdispensing, condensation deposition, evaporative deposition, curtain coating, and mesoscale deposition. Particularly suitable non-contact deposition techniques include inkjet printing and spray atomization deposition.

Inkjet printing operates by ejecting the precursor composition onto the substrate 405 (FIG. 4) in controlled patterns of fluid droplets. Examples of suitable inkjet printing methods include thermal inkjet, continuous inkjet, piezo inkjet, bubble inkjet, drop-on-demand inkjet, and acoustic inkjet. Printheads for such printing methods are commercially available from Hewlett-Packard Corporation, Palo Alto, Calif. and Lexmark International, Lexington, Ky. (thermal inkjet); Domino Printing Sciences, Cambridge, UK (continuous inkjet); and Trident International, Brookfield, Conn., Epson, Torrance, Calif., Hitachi Data Systems Corporation, Santa Clara, Calif., Xaar PLC, Cambridge, UK, Spectra, Lebanon, N.H., and Idanit Technologies, Ltd., Rishon Le Zion, Israel (piezo inkjet).

Examples of a suitable inkjet printhead models include the NOVA series such as the NOVA-Q printhead commercially available from Spectra Inc., and the XJ128 series such as the XJ128-200 printhead commercially available from Xaar PLC. When using the XJ128-200 printhead, the precursor composition 450 may be coated on the substrate 405 by piezoelectrically driving the printhead at 1.25 kilohertz (kHz) and 35 volts (V), with a printing resolution of 300×300 dots-per-inch (dpi). This generates drops with nominal volumes of 70 picoliters (pL).

Based on the printing resolution, the percent of the surface covered (i.e., the pixel coverage), and whether the biological active is present in the precursor composition, the concentration of the biological active (Concentration$_{B.A.}$) in the precursor composition prior to cure as applied on the substrate may be determined as follows:

$$Concentration_{B.A.} = \left(\frac{\#ofDrops}{(Inch)^2}\right)\left(\frac{\% \ Coverage}{100}\right)\left(\frac{Volume}{Drop}\right)(Density_{F.S.})\left(\frac{Wt \ \%_{B.A.}}{100}\right)$$

The (#ofDrops/Inch$^2$) is the number of print pixels in a square inch of the substrate and is based on the selected printing resolution, and the (% Coverage/100) is the fraction of the surface that is printed on. For example, with a printing resolution of 300×300 dpi and a 100% surface coverage of the surface, a total of 90,000 drops of the precursor composition is deposited per square inch of the substrate. By this definition, the percent coverage may be greater than 100%, where a fraction of the pixels are double printed as the printhead executes multiple passes over the article. For example, with a printing resolution of 300×300 dpi and a 200% surface coverage of the surface, a total of 180,000 drops of the precursor composition are deposited per square inch of the surface, where 90,000 drops are deposited in the first pass of the printhead, and another 90,000 drops are deposited over the first set of drops in a second pass.

The (Volume/Drop) is the nominal volume of the drops generated by the selected printhead (e.g., 70 pL is the drop volume typically generated by the XJ128-200 printhead). The (Density$_{F.S.}$) is the average density of the precursor composition and the (Wt %$_{B.A.}$/100) is the weight percent concentration of the biological active in the precursor composition prior to inkjet printing.

The percentage surface coverage of the precursor composition inkjet printed onto the surface may vary as individual needs may require. The percentage required generally depends upon the composition of the precursor composition, including the biological active, the activity level of the selected biological active, and the level of biological activity desired. Examples of suitable percentage surface coverage of the precursor composition inkjet printed onto the surface range from 1% to 500%.

Inkjet printing also allows for the creation of indicia and graphics on the surface of the substrate. As such, the pattern that the precursor composition is inkjet printed onto the surface may also convey textual and graphical messages. In one embodiment, the messages may be visually observable through the use of pigments or dyes contained in the precursor composition. Preferably, however, the biological active itself provides coloration for the messages on the substrate. For example, silver-containing compounds, such as silver oxide, are clear when in the fluid solution, but turn a dark brown color when dried. This precludes the need for additional colorants to render the inkjet printed patterns visually observable. Examples of suitable messages include company logos, instructions for use of the article, brand names, and designs for aesthetic appearance.

Spray atomization deposition operates by emitting the precursor composition 450 (FIG. 4) through an air impingement nozzle or air stripping nozzle to atomize the precursor composition to some degree. The atomized precursor composition 410 is then directed onto the substrate 405. While droplets of the precursor composition may be disposed in a generally uniform pattern on the substrate (which is typical of inkjet printing), spray atomization deposition generally provides a more random pattern of droplets.

An example of suitable spray atomization deposition systems includes commercially available spray heads and bodies, such as those from Spraying Systems Co., Wheaton, Ill. The spray heads may also include fan spray adaptations to fan out the primary atomization sources for creating elliptical patterns. Suitable operating conditions include spraying the precursor composition on the surface of the substrate 405 with a volumetric flow rate of 5 milliliters/minute (mL/min), a web speed of 15 feet/minute (4.6 meters/minute), an atomizer nozzle setting of 23 pounds/inch$^2$ (psi) (159 kilopascals (kpa)), and a fan nozzle setting of 20 psi (138 kpa).

The spray heads generate droplets with diameters ranging from 2 micrometers to 20 micrometers. After the precursor composition 450 dries, the remaining dried droplets on the substrate 405 (FIG. 4) exhibit diameters ranging up to 30 micrometers due to agglomerated droplets. When present in the precursor composition prior to cure, the concentration of the biological active (Concentration$_{B.A.}$) in the precursor composition sprayed on the substrate 405 may be determined as follows:

$$Concentration_{B.A.} = (\% \, SurfaceArea_{F.S.})\left(\frac{\text{Volume}}{\text{Area}}\right)(Density_{F.S.})\left(\frac{\text{Wt }\%_{B.A.}}{100}\right)$$

The percent surface area of the precursor composition (% SurfaceArea$_{F.S.}$) is the ratio of the total surface area of the precursor composition droplets to the surface area of the surface of substrate 405 (FIG. 4), as physically viewed with digital microscopy. The precursor composition droplets are digitally shown as dark drops on a clear background. As such, the total area of the dark regions and the total area of the clear regions may be compared to provide the ratio.

The (Volume/Area) is a conversion of the surface area of the precursor composition droplets to the volume of the precursor composition droplets. The (Density$_{F.S.}$) is the average density of the precursor composition and the (Wt %$_{B.A.}$/100) is the weight percent concentration of the biological active in the precursor composition prior to spraying.

The precursor composition 450 (FIG. 4) may also be deposited on the substrate 405 through separate non-contact deposition systems, such as a plurality of inkjet printing systems. For example, a first inkjet printing system may print a first precursor composition containing a first biological active, and simultaneously or subsequently, a second inkjet printing system may print a second precursor composition containing a second biological active. This is particularly useful for coating multiple biological actives on the same surface, where the biological actives are incompatible in a single precursor composition. The small drop sizes of the precursor composition obtainable by non-contact deposition, reduces the risk of adverse interactions between the first and second biological actives.

The precursor composition may also be deposited by non-contact deposition in a concentration gradient with multiple passes of the non-contact deposition system. For example, a first pass could contain a high concentration of the biological active, and a subsequent pass could contain a low concentration of the same or a different biological active. This is beneficial for controlling the delivery of the biological active. Moreover, the precursor composition may be deposited in a manner such that the biological active is concentrated in certain areas of the surface. For example, the concentration of the biological active may be greater at the central regions of the substrate 405, and less at the periphery. This allows lower concentrations of expensive biological actives to be used.

The precursor composition 450 (FIG. 4) desirably exhibits a sufficiently low viscosity to be coated by non-contact deposition. The desired viscosity will generally depend on the non-contact deposition technique used. For example, for inkjet printing, the precursor composition desirably exhibits a viscosity below 30 centipoise (i.e., 30 milliPascal-seconds), preferably below 25 centipoise, and more preferably below 20 centipoise at the desired inkjetting temperature (typically from 25° C. to 65° C.). However, the optimum viscosity characteristics for the precursor composition will depend primarily upon the inkjetting temperature and the type of inkjet system used. For piezo inkjet applications, suitable viscosities range from 3 to 30 centipoise, preferably from 10 to 16 centipoise, at temperatures ranging from 25° C. to 65° C.

Substrates

A precursor composition can be coated, for example, by non-contact deposition, onto a substrate. Alternatively, a precursor composition can be placed in a mold in contact with a substrate. The precursor composition is then exposed to radiation to at least partially polymerize the polymerizable material of the precursor composition when in contact with the substrate. Thus, a coating of, or shaped, hydrophilic gel material described herein is disposed on (or placed in contact with) a substrate and then cured as a composite structure resulting in the hydrophilic gel material being adhered to the substrate.

The amount of adhesion between the hydrophilic gel material and the substrate can be modified by surface treatment of at least a portion of a substrate's surface prior to contacting the precursor composition with the treated surface. Surface treatments can be by chemical means, such as use of chemical tie-layers or primers (e.g., as disclosed in U.S. Pat. Pub. No. 2003/0021961, or it can be physical methods such as corona treating (e.g., oxygen or nitrogen), plasma treating, or flame treating. Such methods are commonly used to enhance the adhesion of coatings to substrates and are well known to those skilled in the art. Adhesive coatings can also be used, such as, for example, acrylate-based adhesives, A hydrophilic gel material "adheres to" a substrate if the hydrophilic gel material remains adherent to the substrate under normal handling conditions. In some cases, more aggressive adhesion is desirable and suitable chemical or physical means to increase the level of adhesion may be required, as described above. For example, a film that does not adhere to the hydrophilic gel materials of the present invention, and is not considered a suitable substrate, is a fluorinated film such as THV 200 fluorinated copolymer film obtained from 3M Dyneon of St. Paul, Minn. Such a film is typically used as a release liner for hydrogels of the present invention.

In the present invention, a hydrophilic gel material is disposed on the surface of a substrate, or on a surface of a coating applied to at least a portion of at least one surface of a substrate (e.g., an adhesive coating), rather than buried within either the substrate itself or within a coating (e.g., binder layer) applied to at least a portion of at least one surface of a substrate. Thus, for example, preferably, methods described herein and articles resulting therefrom do not typically use hydrophilic gel materials that have been fully polymerized prior to contact with a substrate. For example, the present invention does not include individual shaped hydrophilic gel materials that have been combined with a distinct binder and then coated on a substrate (although it is envisioned that such materials could be mixed with the precursor composition and then used in accordance with the present invention). Surface coatings are advantageous in that the greater effective surface area of the hydrophilic gel material disposed on a surface allows for enhanced accessibility and efficacy, for example, of an active delivered from the hydrophilic gel material to a second surface (e g, skin) in contact with the hydrophilic gel material, as well as a lower amount of an active.

Suitable substrate materials include, for example, fabric, nonwoven fibrous webs, woven fibrous webs, knits, polymer films, foams, and the like. Such substrates can be porous or nonporous. Examples of nonporous substrates are described above. Suitable substrates can be made of natural or synthetic fibers, including, for example, cotton, rayon, wool, hemp, jute, alginates, fiberglass, ceramic fibers, natural rubber, elastomeric polymers, thermoplastic polymers, other familiar backing materials, and combinations thereof. Such materials are typically used as backing substrates in a variety of conventional medical products.

Suitable polymeric materials include, but are not limited to, polyolefins, poly(isoprenes), poly(isobutylenes), poly(butadienes), fluorinated polymers, chlorinated polymers, polyesters, polyamides (e.g., nylon), polyimides, polyethers, poly(ether sulfones), poly(sulfones), polystyrenes, polyphenylene oxides, polyphenylene sulfides, vinyls (including poly(vinylchloride), ethylene-vinyl acetate, poly(vinyl acetates), copolymers of vinyl acetate, poly(vinyl esters), poly(vinyl ethers), poly(vinyl alcohols)), poly(phosphazenes), poly(carbonates), polyurethanes (including polyurethane foams), polyacetates, polyacrylics, and ethylene-propylene-diene rubbers. Suitable polyolefins include, but are not limited to, poly(ethylene), poly(propylene), poly(1-butene), copolymers of ethylene and propylene, copolymers of ethylene and butylene, alpha-olefin copolymers (such as copolymers of 1-butene, 1-hexene, 1-octene, and 1-decene), poly(ethylene-co-1-butene) and poly(ethylene-co-1-butene-co-1-hexene). Suitable fluorinated polymers include, but are not limited to, poly(vinyl fluoride), poly(vinylidene fluoride), copolymers of vinylidene fluoride (such as poly(vinylidene fluoride-co-hexafluoropropylene)), and copolymers of chlorotrifluoroethylene (such as poly(ethylene-co-chlorotrifluoroethylene)). Suitable polyamides include, but are not limited to, poly(imino(1-oxohexamethylene)), poly(iminoadipoyliminohexamethylene), poly(iminoadipoyliminodecamethylene), and polycaprolactam. Suitable polyimides include, but are not limited to, poly(pyromellitimide). Suitable poly(ether sulfone)s include, but are not limited to, poly(diphenylether sulfone), and poly(diphenylsulfone-co-diphenylene oxide sulfone). Suitable copolymers of vinyl acetate include, but are not limited to, poly(ethylene-co-vinyl acetate) and such copolymers in which at least some of the acetate groups have been hydrolyzed to afford various poly(vinyl alcohols).

Suitable substrates (which can form backing or facing layers of a medical article, as described below) can be translucent or transparent polymeric elastic films. The substrate may be made from a radiation-transparent material (e.g., a thermoplastic material). If so, the hydrophilic gel precursor can be at least partially polymerized by being irradiated through the substrate.

Suitable substrates (which can form backing or facing layers of a medical article, as described below) can be a high moisture vapor permeable film.

The substrate may also include a pressure sensitive adhesive (PSA). Examples of suitable PSA's include those based on acrylates, polyurethanes, silicones, rubber based adhesives (including natural rubber, polyisoprene, polyisobutylene, and butyl rubber), and combinations thereof. Examples of suitable acrylates include polymers of alkyl acrylate monomers such as methyl methacrylate, ethyl methacrylate, n-butyl methacrylate, methyl acrylate, ethyl acrylate, n-butyl acrylate, iso-octyl acrylate, iso-nonyl acrylate, 2-ethyl-hexyl acrylate, decyl acrylate, dodecyl acrylate, n-butyl acrylate, hexyl acrylate, and combinations thereof. An example of particularly suitable PSA's include silicone-based adhesives, which exhibit several beneficial properties over traditional PSA's used in wound care applications. For example, silicone-based adhesives may be formulated to offer good skin adhesion characteristics, offer excellent conformability, and provide a gentle release from the skin and wound site. Typically, silicone-based adhesives are formed from the reaction of a polysiloxane gum and a resin as a two part system, one part hindered system to prevent premature reaction, or even as a hot melt system. Examples of suitable silicone-based adhesives include polydiorganosiloxane-based adhesives; adhesives commercially available under the trade designation "SILASTIC 7-6860" Biomedical Grade Adhesive from Dow Corning Corp., Midland, Mich.; adhesives disclosed in Sherman et al., U.S. Pat. No. 6,407,195, and combinations thereof.

Radiation

The radiation used to at least partially polymerize the polymerizable material can be referred to as actinic radiation (e.g., radiation having a wavelength in the ultraviolet or visible region of the spectrum), accelerated particles (e.g., electron beam radiation), thermal (e.g., heat or infrared radiation), or the like. The radiation is often actinic radiation or accelerated particles, because these energy sources tend to provide good control over the initiation and rate of polymerization. Additionally, actinic radiation and accelerated particles can be used for curing at relatively low temperatures. This avoids degrading components that might be sensitive to the relatively high temperatures that might be required to initiate the polymerization reaction with thermal radiation. Alternatively, the radiation can be controlled to avoid degrading components sensitive to heat and/or light, such as active agents, by minimizing radiation levels, and/or longer exposure times.

For the coated article embodiments, exposing the polymerizable material to radiation can be done directly and/or through the substrate, for example. For the shaped hydrogels on a substrate, exposing the polymerizable material to radiation can be done through the substrate and/or wells of the mold, for example.

Any suitable actinic radiation sources that can produce energy in the desired region of the electromagnetic spectrum can be used. Exemplary sources of actinic radiation include mercury lamps, including high, medium and low-pressure, xenon lamps, xenon/mercury lamps, carbon arc lamps, tungsten filament lamps, excimer lamps, lasers, sunlight, light emitting devices (LED) and the like. A plurality of a single type of source or a combination of more than one type of source may be used. Suitable sources may be continuous sources or pulsed sources of actinic radiation. Additionally, filters can be used to screen out detrimental wavelengths from one or more sources that might cause degradation of a component, such as an active, present in the precursor composition.

The radiation source may be a single radiation source or a plurality of radiation sources that are the same or different. The radiation source provides energy such as infrared radiation, visible radiation, ultraviolet radiation, electron beam radiation, microwave radiation, or radio frequency radiation. The particular energy source used will depend upon the particular precursor composition. Suitable non-ionizing radiation sources include continuous and pulsed sources and may be broadband or narrowband sources such as monochromatic sources. Exemplary non-ionizing radiation sources include, but are not limited to, mercury lamps (such as low, medium, and high-pressure versions as well as their additive or doped versions), fluorescent lamps, germicidal lamps, metal halide lamps, halogen lamps, light emitting diodes, lasers, excimer lamps, pulsed xenon lamps, tungsten lamps, and incandescent lamps. Infrared radiation sources and microwave radiation sources may be used, as well as ionizing radiation sources such as electron beams. A combination of radiation sources may also be used.

In some exemplary methods, electromagnetic radiation having a wavelength in the range of 100 to 1000 nanometers, 100 to 800 nanometers, or 100 to 700 nanometers can be used. In some methods, ultraviolet radiation having a wavelength in the range of 100 to 400 nanometers or 200 to 400 nanometers can be used. Ultraviolet radiation at wavelengths below 200 nm from excimer sources, for example, can be used. In some embodiments, the radiation source is a high-radiance ultraviolet source, such as a medium-pressure mercury lamp of at least 100 W/inch (40 W/cm). Low-radiance lamps, including low-pressure mercury lamps such as germicidal lamps, can also be used.

The precursor composition may be exposed to radiation for a time generally no more than 30 seconds, no more than 15 seconds, no more than 10 seconds, no more than 5 seconds, no more than 3 seconds, no more than 2 seconds, no more than 1 second or no more than 0.5 seconds. Upon exposure to radiation, the polymerizable material can at least partially polymerize to form a swollen hydrophilic gel material (e.g., shaped polymeric material). The polymerizable material may crosslink or the polymer chains may propagate during exposure to radiation.

The hydrophilic gel materials are formed by subjecting the precursor composition to radiation resulting in the free-radical polymerization of the polymerizable material. For example, the shaped hydrophilic gel materials are formed by subjecting the precursor composition to radiation within the wells resulting in the free-radical polymerization of the polymerizable material. In this embodiment, the polymerized polymeric material assumes the shape of the wells of the mold. Because the precursor composition includes polar solvent in addition to the polymerizable material, hydrophilic gel materials can be swollen with the polar solvent.

Dried Materials and Uses of Swollen and Dried Materials

In some embodiments of the hydrophilic gel material and the methods of making the hydrophilic gel material, at least a portion of the polar solvent can be removed from the first swollen hydrophilic gel material to form a dried hydrophilic gel material. The dried hydrophilic gel material can then be contacted with a sorbate for a time sufficient for the dried hydrophilic gel material to sorb at least a portion of the sorbate. That is, a first swollen hydrophilic gel material can be dried to form a dried polymeric hydrophilic gel material that can then be contacted with a sorbate to form a second swollen shaped hydrophilic gel material. The sorbate can contain at least one active agent. In addition to the active agent, the sorbate can include a fluid such as a liquid or a supercritical fluid. Some exemplary sorbates include an active agent plus a polar solvent.

As used herein, the term "sorb" refers to adsorb, absorb, or a combination thereof. Likewise, the term "sorption" refers to adsorption, absorption, or a combination thereof. The sorption can be a chemical process (i.e., a chemical reaction occurs), a physical process (i.e., no chemical reaction occurs), or both. The term "sorbate" refers to a composition that can be sorbed by hydrophilic gel materials such as dried hydrophilic gel materials.

More specifically, a method of making a hydrophilic gel material that includes an active agent is provided. The method includes forming a precursor composition containing (a) a polar solvent and (b) polymerizable material that forms a single phase with the polar solvent. The polymerizable material is capable of free-radical polymerization and has an average number of ethylenically unsaturated groups per molecule of at least 1.0, preferably greater than 1.0, and more at least 1.2.

In some embodiments, the method further includes adding a portion of the precursor composition to a mold having at least two wells, wherein the precursor composition is retained within the wells. The wells of the mold may be formed by contacting a substrate with the mold (e.g., a screen-type mold with only side walls) prior to adding the precursor composition to the wells, or a substrate may be positioned to contact the precursor composition after it is added to the wells of the mold. The precursor composition is positioned in at least a portion of the two separate wells. The precursor composition within the wells is exposed to radiation for a time sufficient to at least partially polymerize the polymerizable material and to form a first swollen shaped polymeric material. The method further includes removing at least a portion of the polar solvent from the first swollen shaped polymeric material to form a dried shaped polymeric material. The dried shaped polymeric material is then contacted with a sorbate for a time sufficient for the dried shaped polymeric material to sorb at least a portion of the sorbate and to form a second swollen shaped polymeric material. The sorbate typically contains an active agent. The active agent can be a biologically active agent, a non-biologically active agent, or a mixture thereof.

In other embodiments, the method further includes coating a substrate by non-contact deposition a coating of precursor composition. The precursor composition coated on the substrate is exposed to radiation for a time sufficient to at least partially polymerize the polymerizable material and to form a first swollen coating of hydrophilic gel material. The method further includes removing at least a portion of the polar solvent from the first swollen coating of hydrophilic gel material to form a dried coating of hydrophilic gel material coated on the substrate. The dried coating of hydrophilic gel material is then contacted with a sorbate for a time sufficient for the dried coating of hydrophilic gel material to sorb at least a portion of the sorbate and to form a second swollen coating of hydrophilic gel material coated on the substrate. The sorbate can contain an active agent. The active agent can be a biologically active agent, a non-biologically active agent, or a mixture thereof.

The amount of polar solvent removed from the first swollen hydrophilic gel material to form a dried polymeric material can be any amount desired up to the amount present in the original precursor composition. The dried polymeric material often contains at least a small amount of polar solvent remaining in the polymeric material. Additionally, if the polymeric material will be contacted with a sorbate to sorb an active agent into or onto the polymeric hydrophilic gel materials, the amount of polar solvent present in the dried polymeric material is generally no more than 25 weight percent based on the weight of the dried hydrophilic gel material. The amount of polar solvent in the dried hydrophilic gel material can be less than 20 weight percent, less than 15 weight percent, less than 10 weight percent, less than 5 weight percent, less than 2 weight percent, or less than 1 weight percent of the weight of the dried polymeric hydrophilic gel material. Generally, the more solvent removed from the first swollen hydrophilic gel material, the greater is the amount of the sorbate that can be sorbed by the dried hydrophilic gel material.

In certain embodiments, the first swollen coating of hydrophilic gel material shrinks when the polar solvent is removed. In other embodiments, the first swollen shaped polymeric material shrinks when the polar solvent is removed and may resemble collapsed, deformed or deflated shapes based on the wells of the mold; some of the dried polymeric shaped hydrophilic gel materials may have different shapes when viewed in the cross-section. The cross-sectional shape of the dried shaped polymeric material will depend on the cross-sectional shape of the first swollen shaped polymeric material.

The amount of shrinkage depends on the volume of polar solvent initially present in the first swollen hydrophilic gel material (e.g., first swollen shaped polymeric material) and the extent to which it is removed by drying. The hydrophilic gel materials may experience shrinking in all three dimensions separately or uniformly.

The dried hydrophilic gel material (particularly in the absence of an active agent or other insoluble additives) generally remains homogeneous and does not contain macroscopic (i.e., greater than 100 nm) internal pores or channels. Generally, the dried hydrophilic gel materials have no discernible porosity or voids when viewed under a microscope. Generally, there are no discernible pores when the dried hydrophilic gel materials are viewed using environmental scanning electron microscopy with magnification up to 50 times. Some dried hydrophilic gel materials have no discernible pores when viewed using field emission scanning electron microscopy with magnification up to 50,000 times. The dried hydrophilic gel materials may have high modulus, high crush strength, or a combination thereof. These properties can be similar to or greater than those of the swollen hydrophilic gel material.

A swollen hydrophilic gel material can be dried (i.e., the swollen polymeric material can have at least a portion of the polar solvent removed) by any of a variety of methods including heating in a conventional oven such as a convection oven, heating in a microwave oven, air-drying, freeze-drying, or vacuum-drying. The optimal method for drying a given hydrophilic gel material composition is dependent on the identity and amount of the polar solvent present in the swollen hydrophilic gel material as well as the heat stability of components in the hydrophilic gel material such as bioactive agents. When water is present, preferred drying methods include conventional ovens such as convection ovens, microwave ovens, vacuum ovens, and freeze-drying. For water, suitable temperatures for drying at atmospheric pressure are often close to or exceeding 100° C. Alternatively, a longer dwell time at a lower temperature is also acceptable for producing dried hydrophilic gel. In some cases it may be desirable to heat the dried hydrophilic gel material to higher temperatures. This may improve the hydrophilic gel material strength through condensation or other chemical reactions. For example, the hydrophilic gel materials can be heated to greater than 140° C., greater than 160° C., or even greater than 180° C. For example, the shaped hydrophilic gel material does not coalesce when dried to form, for example, a film or sheet. Rather, the dried shaped hydrophilic gel materials tend to remain as separate shaped hydrophilic gel materials.

The dried hydrophilic gel material can be readily swollen again, for example, by impregnating with a sorbate, back to its swollen state that can approximate the original size. Typically, the volume of sorbate that can be sorbed by the dried hydrophilic gel material to form a second swollen hydrophilic gel material is nearly equal to the volume of polar solvent and other non-polymerized components removed from the first swollen hydrophilic gel material during the drying process. In cases where the polar solvent present in the precursor composition and in the resulting first swollen hydrophilic gel material is different than the solvent in the sorbate used to swell the hydrophilic gel material a second time (e.g., swell a dried hydrophilic gel material), the dried hydrophilic gel material may swell very little or may swell beyond its original, as polymerized, dimensions. For example, a sorbate comprising a non-polar solvent may take a day or a period of time longer than a day to reswell the dried hydrophilic gel material to its final size.

Dried hydrophilic gel materials can be loaded with an active agent, especially those that are sensitive to the heat or radiation encountered during the formation of the swollen hydrophilic gel materials such as medicaments, pharmaceuticals, insecticides, herbicides, dyes, fragrances, or mixtures thereof. To provide a hydrophilic gel material with an active agent, the dried hydrophilic gel material can be contacted with a sorbate that contains the active agent. If the active agent is not a liquid, the sorbate typically also contains a fluid such as a polar solvent or supercritical fluid (e.g., carbon dioxide). The sorbate can be a solution, suspension, emulsion (e.g., macro emulsion, microemulsion, or a nanoemulsion) or dispersion. In many embodiments, the sorbate is a solution. The dried hydrophilic gel material typically sorbs at least a portion of the sorbate. Exposure of the dried hydrophilic gel material to the sorbate results in the impregnation of the hydrophilic gel material with an active agent.

The sorbate often includes the active agent and a liquid such as a polar solvent. Sorption of the liquid often causes the hydrophilic gel material to swell. The liquid typically facilitates the transport of the active agent into the hydrophilic gel material. The liquid will often carry the active agent throughout the hydrophilic gel material to form a homogeneous hydrophilic gel material. In some embodiments, however, the active agent may remain on the surface of the hydrophilic gel material or there may be a gradient of the active agent throughout the hydrophilic gel material with a higher concentration on the surface. For example, the size of the active agent (e.g., molecular size), its charge relative to the hydrophilic gel material, as well as the polar solvent composition may affect the migration (e.g., diffusion) of the active agent into the dried hydrophilic gel material The dried hydrophilic gel material can often sorb an amount of sorbate that is equal to at least 10 weight percent, at least 20 weight percent, at least 40 weight percent, at least 50 weight percent, at least 60 weight percent, at least 80 weight percent, at least 100 weight percent, at least 120 weight percent, at least 140 weight percent, at least 160 weight percent, at least 180 weight percent, or at least 200 weight percent based on the weight of the dried hydrophilic gel materials. The weight increase is typically less than 300 weight percent, less than 275 weight percent, or less than 250 weight percent based on the weight of the dried hydrophilic gel materials.

The hydrophilic gel materials can be a carrier for an active agent, which can be present in at least a portion of the interior of the hydrophilic gel material or on at least a portion of the surface of the hydrophilic gel material. The active agent can be included in the precursor composition used to form the hydrophilic gel material. Alternatively, the active agent can be sorbed by a hydrophilic gel material that has been at least partially dried. The hydrophilic gel material can provide diffusion-controlled transport both into and from the bulk. That is, in many embodiments, the active agent can diffuse into the hydrophilic gel material, diffuse out of the hydrophilic gel material, or both. The rate of diffusion should be controllable by, for example, varying the polymeric material and the crosslink density, by varying the polar solvent, by varying the solubility of the active agent in the polar solvent, and by varying the molecular weight of the active agent. The diffusion can take place over a period of several hours, several days, several weeks, or several months.

In some applications, it may be desirable that the hydrophilic gel material containing the active agent is in a dry state. After the addition of the active agent by exposing the dried hydrophilic gel material to the sorbate to form a second swollen hydrophilic gel material that contains the active agent, the second swollen hydrophilic gel material can be dried again. When this dried hydrophilic gel material is exposed to moisture, the active agent can diffuse from the hydrophilic gel material. The active agent can remain dormant in the hydrophilic gel material until exposed to moisture. That is, the active agent can be stored within the dry hydrophilic gel material until the hydrophilic gel material is exposed to moisture. This can prevent the waste or loss of the active agent when not needed and can improve the stability of many moisture sensitive active agents that may degrade by hydrolysis, oxidation, or other mechanisms. Potential applications taking advantage of the diffusion controlled uptake or delivery of the active agent include, for example, drug delivery, wound management, and sustained-released antibacterial and antifungal protection, air freshening agents, time-released insecticides, and time-released attractants for higher animals such as fish or mammals.

The hydrophilic gel materials may be regenerated multiple times by the steps of sorbing and drying. The hydrophilic gel materials may be regenerated multiple times with the sorbate. In another embodiment, hydrophilic gel materials containing a first active agent may be exposed to a concentrated solution of a second active agent or other material. The second active agent may sorb into hydrophilic gel materials to form hydrophilic gel materials having more than active agent. The second active agent may sorb into the hydrophilic gel material to the exclusion of the first agent from the hydrophilic gel material. A combination of active agents may be sorbed by the hydrophilic gel materials, and optionally dried.

As wound dressings, the hydrophilic gel materials can be loaded with various active agents that provide a therapeutic function. Wound dressings containing these active agents may reduce or eliminate infection of the wound. In addition, these wound dressings can speed the rate of wound healing when therapeutic active agents such as anti-inflammatory drugs, growth factors, alpha-hydroxyacids, enzyme inhibitors such as matrix metalloproteinase (MMP) inhibitors, enzyme activators, vasodilaters, chemotactic agents, hemostatic agents (e.g., thrombin), antimicrobial agents, antihistamines, antitoxins, anesthetics, analgesics, vitamins, nutrients, or combinations are added to the hydrophilic gel materials. When used in wound dressings, the hydrophilic gel materials are typically dry prior to use in highly exuding wounds but may be used swollen to add moisture to dry wounds.

Medical articles, such as wound dressings, may also include a liner to protect the substrate and the coating of hydrophilic gel material prior to use. Liners which are suitable for use may be made of materials such as kraft papers, polyethylene, polypropylene, polyester, and combinations thereof. The liners are preferably coated with compositions containing release agents, such as polymerized fluorochemicals or silicones. The low surface energy of the liner provides for an easy removal from the substrate, hydrophilic gel material, and/or any PSA present.

In some embodiments, the swollen hydrophilic gel material can be used to deliver antimicrobial agents to either mammalian tissue or another environment outside of the hydrophilic gel materials. Some exemplary antimicrobial agents that can be added to the hydrophilic gel material include iodine and its various complexed forms, which are commonly referred to as iodophors. Iodophors are complexes of elemental iodine or other iodine species (e.g., triiodide) with certain carriers. Iodophors can be formed between elemental iodine or other iodine species, and the polymer matrix itself. These iodophors function by not only increasing the iodine solubility but by reducing the level of free molecular iodine in solution and by providing a type of sustained release reservoir of iodine. Iodophors can be formed using polymeric carriers such as polyvinylpyrrolidone (PVP); copolymers of N-vinyl lactams with other unsaturated monomers such as, but not limited to, acrylates and acrylamides; various polyether glycols (PEGs) including polyether-containing surfactants such as nonylphenolethoxylates and the like; polyvinyl alcohols; polycarboxylic acids such as polyacrylic acid; polyacrylamides; and polysaccharides such as dextrose. Other suitable iodophors include the protonated amine oxide surfactant-triiodide complexes described in U.S. Pat. No. 4,597,975 (Woodward et al.). In some applications, the iodophor is povidone-iodine. This can be obtained commercially as povidone-iodine USP, which is a complex of K30 polyvinylpyrrolidone and iodide wherein the available iodine is present at 9 weight percent to 12 weight percent.

In some embodiments, various combinations of antimicrobial agents can be used in the precursor composition or sorbate. Any other known antimicrobial agents that are compatible with the precursor compositions or the resulting hydrophilic gel materials can be used. These include, but are not limited to, chlorhexidine salts such as chlorhexidine gluconate (CHG), parachlorometaxylenol (PCMX), triclosan, hexachlorophene, fatty acid monoesters and monoethers of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a ($C_{12}$-$C_{22}$) hydrophobe and a quaternary ammonium group or a protonated tertiary amino group, quaternary amino-containing compounds such as quaternary silanes and polyquaternary amines such as polyhexamethylene biguanide, silver containing compounds such as silver metal, silver salts such as silver chloride, silver oxide and silver sulfadiazine, methyl parabens, ethyl parabens, propyl parabens, butyl parabens, octenidene, 2-bromo-2-nitropropane-1,3 diol, or mixtures thereof. Other antimicrobial agents are described in U.S. Pat. Appl. Pub. Nos. 2006/0052452 (Scholz et al.), 2006/0051385 (Scholz et al.), and 2006/0051384 (Scholz et al.). Note that certain active agents such as antimicrobial agents that have a low solubility in water can be dissolved in volatile solvents that can be sorbed by the hydrophilic gel materials and subsequently removed by evaporation.

Active agents also can be sorbed into the hydrophilic gel materials of this invention and used to deliver any of the aforementioned active agents to the skin for transdermal delivery. This can be accomplished in a patch format which is similar to a wound dressing. The hydrophilic gel materials may or may not be in direct contact with the skin but will serve as a reservoir for the active agent.

Additionally, hydrophilic gel materials can be used to concentrate various materials such as contaminants or toxins. For example, the hydrophilic gel materials can be used to remove contaminants from water systems or ecosystems. By incorporation of various functionalities into the hydrophilic gel material such as chelating agents, it may be possible to remove heavy metals, radioactive contaminants, and the like.

Hydrophilic gel materials often contain unreacted ethylenically unsaturated groups. These ethylenically unsaturated groups can be reacted with other monomers, such as monomers in a coating composition. The hydrophilic gel materials can be polymerized into the final coating. Further, some hydrophilic gel materials have other functional groups that can be further reacted. For example, some of the poly (alkylene oxide (meth)acrylates) included in the precursor composition have hydroxy groups that can undergo various nucleophilic substitution reactions or condensation reactions.

Exemplary cosmetic and personal care applications, for which the hydrophilic gel materials may be used include, but are not limited to, wound care products such as absorbent wound dressings and wound packing to absorb excess exudates; first aid dressings, hot/cold packs, baby products, such as baby shampoos, lotions, powders and creams; bath preparations, such as bath oils, tablets and salts, bubble baths, bath fragrances and bath capsules; eye makeup preparations, such as eyebrow pencils, eyeliners, eye shadows, eye lotions, eye makeup removers and mascaras; fragrance preparations, such as colognes and toilet waters, powders and sachets; noncoloring hair preparations, such as hair conditioners, hair spray, hair straighteners, permanent waves, rinses, shampoos, tonics, dressings and other grooming aids; color cosmetics; hair coloring preparations such as hair dyes, hair tints, hair shampoos, hair color sprays, hair lighteners and hair bleaches; makeup preparations such as face powders, foundations, leg and body paints, lipsticks, makeup bases, rouges and makeup fixatives; manicuring preparations such as basecoats and undercoats, cuticle softeners, nail creams and lotions, nail extenders, nail polishes and enamels, and nail polish and enamel removers; oral hygiene products such as dentifrices, mouthwashes, and sustained release periodontal products and buccal cavity products each for the prevention and treatment of gingivitis; personal cleanliness products, such as bath soaps and detergents, deodorants, douches and feminine hygiene products; shaving preparations such as aftershave lotions, beard softeners, men's talcum powders, shaving creams, shaving soap and pre-shave lotions; skin care preparations such as cleansing preparations, skin antiseptics, depilatories, face and neck cleansers, body and hand cleansers, foot powders and sprays, moisturizers, night preparations, paste masks, and skin fresheners; and suntan preparations such as suntan creams, gels and lotions, and indoor tanning preparations.

In some applications, the hydrophilic gel material contains an indicator that can detect the presence or absence of another compound of interest. The indicator can be added either to the precursor composition or to the dried hydrophilic gel material using a sorbate that contains the indicator and an optional fluid such as a polar solvent (e.g., water, dimethylformamide, or the like). The hydrophilic gel materials can be contacted with samples that potentially contain the compound to be detected. The indicator can then change color if the sample contains the compound to be detected. If the indicator does not migrate out of the hydrophilic gel material when exposed to the sample, the hydrophilic gel material may change color. If the indicator migrates out of the material when exposed to the sample, the sample itself may change color.

More specifically, the hydrophilic gel material can be loaded with an indicator such as ninhydrin that is capable of detecting the presence of amino-containing materials. The dried hydrophilic gel materials, which often are clear and colorless, can be loaded with ninhydrin to form a hydrophilic gel material that has a yellow color. A sorbate that contains the ninhydrin as well as a polar solvent can be used to add the active agent to the hydrophilic gel material. Upon contact of the ninhydrin-containing hydrophilic gel material with an amino-containing material, the ninhydrin changes from a yellow to vivid purple color. Depending on the relative rates of diffusion of the ninhydrin and the amino-containing materials, the hydrophilic gel material can change color from yellow to purple or the ninhydrin can migrate out of the hydrophilic gel material and alter the color of an amino-containing sample. For example, small amino-containing materials can diffuse into the ninhydrin-containing hydrophilic gel material and change the color of the hydrophilic gel materials from yellow to purple. However, relatively large proteins cannot diffuse into the hydrophilic gel materials as easily as the ninhydrin can migrate out of the materials. The color of the sample containing the protein can change to a purple color while the hydrophilic gel material may not change to a purple color. In some other examples that contain a mixture of amino-containing materials, both the hydrophilic gel material and the amino-containing sample may change to a purple color.

Hydrophilic gel materials loaded with dyes can be used as saturation indicators. The dye-containing hydrophilic gel materials can be dried. When the hydrophilic gel material is contacted with water, the dye can diffuse out of the hydrophilic gel material and alter the color of the water. Alternatively, dyes can be incorporated that are colorless in the absence of water but turn colored when water is sorbed into the hydrophilic gel material. For example, certain pH indicators such as phenolphthalein are colorless when dry but will turn color when wet.

An article, such as a medical article, as described herein, may also include a porous or non-porous facing layer to provide a fluid permeable barrier between the wound site and the absorbent hydrophilic gel layer. The facing layer allows transport of moisture (i.e., fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one embodiment, the facing layer is conformable to animal (including human) anatomical surfaces, has a moisture vapor transmission rate of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations as a means for passing wound exudate through the facing layer. This means that the facing layer does not pass liquid water under normal wound treatment conditions except at the places in the facing layer which are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer must have the aforesaid MVTR. Therefore, if the facing layer is impermeable to liquid water except for the perforation means, the adhesive can be permeable to liquid water and vice versa. Porous or non-porous facing layers such as perforated polyurethane, polyamide, polyester, polypropylene, polyethylene, polyether-amide, polyurethanes, chlorinated polyethylene, styrene/butadiene block copolymers ("KRATON" brand thermoplastic rubber, Shell Chemical Company, Houston, Tex.) and polyvinyl chloride and those described in U.S. Pat. No. 3,121,021 that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. The backing can be a high moisture vapor permeable film backing Preferably the backing layer is impermeable to liquid water and has a moisture vapor transmission rate of at least 600 grams per square meter per 24 hours at an 80% relative humidity differential at 40° C. (per Chen, U.S. Pat. No. 5,733,570).

U.S. Pat. No. 3,645,835 describes methods of making such films and methods for testing their permeability. When used as a wound dressing, the backing layer is generally conformable to anatomical surfaces. As such, when the backing layer is applied to an anatomical surface, it conforms to the surface even when the surface is moved. The backing layer is also conformable to animal anatomical joints. When the joint is flexed and then returned to its unflexed position, the backing layer can be made such that it stretches to accommodate the flexion of the joint, but is resilient enough to continue to conform to the joint when the joint is returned to its unflexed position.

A description of preferred backing layers for use with wound dressings can be found in U.S. Pat. Nos. 5,088,483 and 5,160,315. Specific suitable backing materials are elastomeric polyurethane, co-polyester, or polyether block amide films. These films combine the desirable properties of resiliency, high moisture vapor permeability and transparency found in backings.

The preferred embodiments for the facing and backing layers are thin conformable polymeric films. Generally the films are from 12 to 50 microns in thickness, preferably from 12 to 25 microns. Conformability is somewhat dependent on thickness, thus the thinner the film the more conformable the film. When the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes, such as ESTANE polyurethanes (available from B.F. Goodrich, Cleveland, Ohio), elastomeric polyester such as HYTREL polyester elastomer (E.I. duPont deNemours & Co., Wilmington, Del.), blends of polyurethane and polyester, polyvinyl chloride, and polyether-amide block copolymer, such as PEBAX available from Elf-Atochem. Particularly preferred films for use in the present invention are polyurethane and elastomeric polyester films. The polyurethane and elastomeric polyester films exhibit a resilient property that allows the films to have good conformability.

Many different constructions of an absorbent dressing are possible with hydrophilic gel absorbent layer and the optional facing layer and/or backing layer. In one embodiment, the areas of the facing layer and the backing layer are greater than that of the absorbent layer and the facing layer is bonded to the backing layer, thereby forming a pouch, with the absorbent disposed between the two. In another embodiment the one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area that the gel layer. Alternatively, the backing and facing layers may be bonded to each other, and may or may not be bonded to the gel layer. In these last constructions, the absorbent layer is constrained within a pouch created by the attachment of the facing and backing layers to each other. The layers may be bonded to each other by any conventional means such as adhesives, heat sealing, or other bonding means.

In certain preferred embodiments, the facing and backing films are generally adhered to each other at the periphery of the hydrophilic gel layer to produce a composite article comprising a backing layer, a facing layer, and a hydrophilic gel layer disposed between the two. In such a construction the facing and backing layers, sealed at their periphery, form a reservoir with the absorbent hydrophilic gel layer disposed between the two.

It is preferred that the facing, gel, and backing layers of the present invention be at least translucent and more preferably sufficiently transparent so that the wound site to which they are applied can be viewed through the dressing. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films, such as ESTANE polyurethanes (B.F. Goodrich, Cleveland, Ohio); elastomeric polyesters, such as HYTREL polyester elastomers (E.I. duPont deNemours & Co., Wilmington, Del.; and, polyether block amides (PEBAX, Elf Altochem North America, Philadelphia, Pa.). Other useful films are those describes in U.S. Pat. Nos. 4,499,896; 4,598,004; and 5,849,325 (Heinecke et al.).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive which can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration -A-B-A- wherein each A is a thermoplastic polymer block with a glass transition temperature above room temperature (i.e., above 20° C.) having an average molecular weight between 5000 and 125,000 and B is a polymer block of a conjugated diene having an average molecular weight between 15,000 and 250,000. Additional examples of useful adhesives are acrylic adhesives such as iso-octyl acrylate/n-vinyl pyrrolidone copolymer adhesives and crosslinked acrylate adhesives such as for example those described in U.S. Pat. No. 4,112,213. Inclusion in the adhesive of medicaments is useful for enhancing wound healing and the inclusion of antimicrobial agents such as iodine is useful for preventing infection.

The adhesive may be chosen to be permeable to water or wound exudate, or the adhesive may be pattern coated on the front surface of the wound dressing (i.e., the surface in contact with the wound site, whether it is the front surface of the facing or backing layers) so as to not impede the flow of exudate to the absorbent layer, i.e., the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are Polyslik S-8004, 83 pound (135.4 g/m$^2$) bleached silicone release paper supplied by H.P. Smith Co., Chicago, Ill., and 80 pound (130.5 g/m$^2$) bleached two-sided silicone coated paper (2-80-BKG-157) supplied by Daubert Chemical Co., Dixon, Ill.

A wound dressing may also comprise a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. Nos. 5,531,855 and 5,738,642 (Heinecke et al.).

In the medical articles of the claimed invention that are used as wound dressings, the dressings preferably can remove excess exudate from the wound, maintain a moist wound environment, allow for delivery and active ingredient if desired, allow for gas exchange so that oxygen, water vapor, and carbon dioxide can pass through the dressing, are thermally insulating to maintain the wound at body temperature, may be impermeable to liquids and microorganisms to minimize contamination and infection, may be non-adherent to the wound so that no damage is done to the granulating tissue, and may minimize the need to cleanse the wound of dressing material. Further, the medical articles can be essentially transparent to allow visual inspection in healthcare applications without removal of the medical article.

Other useful aspects of the hydrophilic gel materials described herein include those identified for patterned hydrophilic gel layers in U.S. Pat. No. 6,566,575.

General Exemplary Embodiments

1. A method of making an article comprising a substrate and a hydrophilic gel material disposed thereon (preferably, adhered thereto), the method comprising:
    providing a precursor composition comprising:
    (a) at least 10 weight percent polar solvent based on a total weight of the precursor composition; and
    (b) polymerizable material capable of free-radical polymerization and having an average number of ethylenically unsaturated groups per molecule equal to at least 1.2, wherein the polymerizable material is miscible with the polar solvent;
    providing a mold having at least two separate wells;
    adding the precursor composition to the mold, the precursor composition being positioned in at least a portion of at least two separate wells;
    providing a substrate and positioning the substrate to at least partially contact the precursor composition; and
    exposing the precursor composition within the wells to radiation to at least partially polymerize the polymerizable material and to form a first swollen shaped hydrophilic gel material on (preferably, adhered to) the substrate.
2. The method of embodiment 1, wherein the polar solvent comprises water; and the precursor composition comprises no greater than 90 weight percent polymerizable material based on the total weight of the precursor composition, wherein the polymerizable material comprises a poly(alkylene oxide) (meth)acrylate) having at least 2 (meth)acryloyl groups and having at least 5 alkylene oxide units.
3. The method of embodiment 1, wherein the polar solvent is present in an amount of greater than 10 weight percent.
4. A method of making an article comprising a substrate and a hydrophilic gel material disposed thereon (preferably, adhered thereto), the method comprising:
    providing a precursor composition comprising:
    (a) at least 5 weight percent polar solvent based on a total weight of the precursor composition; and
    (b) polymerizable material capable of free-radical polymerization and having an average number of ethylenically unsaturated groups per molecule greater than 1.0, wherein the polymerizable material is miscible with the polar solvent;

providing a mold having a substrate in contact therewith in a manner to form at least two separate wells;

adding the precursor composition to the mold, the precursor composition being positioned in at least a portion of at least two separate wells; and exposing the precursor composition within the wells to radiation to at least partially polymerize the polymerizable material and to form a first swollen shaped hydrophilic gel material on (preferably, adhered to) the substrate.

5. The method of embodiment 4, wherein the precursor composition comprises:
    (a) at least 10 weight percent polar solvent based on the total weight of the precursor composition, wherein the polar solvent comprises water; and
    (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material comprises a poly(alkylene oxide (meth)acrylate) having at least 2 (meth)acryloyl groups and having at least 5 alkylene oxide units.

6. The method of any one of embodiments 1 through 5, wherein exposing the precursor composition within the wells to radiation comprises exposing the precursor composition through the wells.

7. The method of any one of the previous embodiments, further comprising removing the first swollen shaped hydrophilic gel material and substrate from the mold.

8. The method of any one of the previous embodiments, further comprising removing at least a portion of the polar solvent from the first swollen shaped hydrophilic gel material to form a dried shaped hydrophilic gel material.

9. The method of embodiment 8, further comprising contacting the dried shaped hydrophilic gel material with a sorbate for a time sufficient for the dried shaped hydrophilic gel material to sorb at least a portion of the sorbate to form a second swollen shaped hydrophilic gel material.

10. The method of embodiment 9, wherein the sorbate comprises at least one active agent.

11. The method of embodiment 10, wherein the at least one active agent in the sorbate comprises a bioactive agent.

12. The method of embodiment 10, further comprising drying the second swollen shaped hydrophilic gel material.

13. The method of any one of the previous embodiments wherein adding the precursor composition to the mold comprises overfilling the at least two separate wells, wherein the precursor composition resides on a first surface of the mold between the wells.

14. A method of making an article comprising a substrate and a hydrophilic gel material disposed thereon (preferably, adhered thereto), the method comprising:
    providing a precursor composition comprising:
        (a) at least 5 weight percent polar solvent based on a total weight of the precursor composition; and
        (b) polymerizable material capable of free-radical polymerization and having an average number of ethylenically unsaturated groups per molecule greater than 1.0, wherein the polymerizable material is miscible with the polar solvent;
    coating the precursor composition on at least a portion of at least one surface of a substrate; and
    exposing the precursor composition to radiation to at least partially polymerize the polymerizable material to provide a coating of first swollen hydrophilic gel material on (preferably, adhered to) the substrate.

15. The method of embodiment 14, wherein the precursor composition comprises:
    (a) greater than 10 weight percent polar solvent based on a total weight of the precursor composition; and
    (b) polymerizable material capable of free-radical polymerization and having an average number of ethylenically unsaturated groups per molecule equal to at least 1.2.

16. The method of embodiment 14, wherein the precursor composition comprises:
    (a) at least 10 weight percent polar solvent based on the total weight of the precursor composition, wherein the polar solvent comprises water; and
    (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material comprises a poly(alkylene oxide (meth)acrylate) having at least 2 (meth)acryloyl groups and having at least 5 alkylene oxide units.

17. The method of embodiment 14, wherein the precursor composition comprises:
    (a) at least 10 weight percent polar solvent based on the total weight of the precursor composition; and
    (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units and the poly(alkylene oxide (meth)acrylate) having a weight average molecular weight less than 2,000 g/mole.

18. The method of embodiment 14, wherein the precursor composition comprises:
    (a) greater than 10 weight percent polar solvent based on a total weight of the precursor composition; and
    (b) less than 90 weight percent polymerizable material based on the total weight of the precursor composition, the polymerizable material being capable of free-radical polymerization and having an average number of ethylenically unsaturated groups per molecule equal to at least 1.2, the polymerizable material being miscible in the polar solvent and comprising
        i) a poly(alkylene oxide (meth)acrylate) having at least 2 (meth)acryloyl functional groups and having at least 5 alkylene oxide units; and
        ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof 19. The method of any one of embodiments 14 through 18, wherein:
    coating the precursor composition comprises using a non-contact deposition technique; and
    exposing the precursor composition to radiation to at least partially polymerize the polymerizable material to provide a coating of first swollen hydrophilic gel material on a substrate comprises forming a discontinuous coating of first swollen hydrophilic gel material on at least a portion of at least one surface of a substrate.

20. The method of embodiment 19, wherein the non-contact deposition comprises inkjet printing.

21. The method of embodiment 19, wherein the non-contact deposition comprises spray atomization deposition.

22. The method of any one of embodiments 14 through 21, further comprising removing at least a portion of the polar solvent from the first swollen hydrophilic gel material to form a coating of dried hydrophilic gel material.

23. The method of embodiment 22, further comprising contacting dried hydrophilic gel material with a sorbate for a time sufficient for the dried hydrophilic gel material to sorb at least a portion of the sorbate to form a coating of second swollen hydrophilic gel material 24. The method of embodiment 23, wherein the sorbate comprises at least one active agent.

25. The method of any one of the previous embodiments, wherein the polymerizable material comprises a poly (alkylene oxide (meth)acrylate) having an average number of (meth)acryloyl groups per molecule equal to at least two.

26. The method of any one of the previous embodiments, wherein the poly(alkylene oxide (meth)acrylate) has a weight average molecular weight no greater than 2000 g/mole.

27. The method of any one of the previous embodiments, wherein the polymerizable material comprises a poly (alkylene oxide (meth) acrylate) having at least 3 (meth) acryloyl groups.

28. The method of any one of the previous embodiments, wherein the precursor composition further comprises a photoinitiator.

29. The method of embodiment 28 wherein the photoinitiator is 2-hydroxy-1-[4-(2-hydroxyethoxyl)phenyl]-2-methyl-1-propanone.

30. The method of any one of the previous embodiments, wherein the precursor composition further comprises an active agent.

31. The method of embodiment 30, wherein the active agent is a bioactive agent.

32. The method of any one of the previous embodiments, wherein the precursor composition is exposed to radiation through the substrate.

33. An article comprising a substrate and a shaped hydrophilic gel material disposed thereon (preferably, adhered thereto), the article made by the method of any one of embodiments 1 through 13 and embodiments 25 through 32 as they depend on embodiments 1 through 13.

34. An article comprising a substrate and a coating of a hydrophilic gel material disposed thereon (preferably, adhered thereto), the article made by the method of any one of embodiments 14 through 24 and embodiments 25 through 32 as they depend on embodiments 14 through 24.

35. An article comprising a substrate having a shaped hydrophilic gel material disposed thereon (preferably, adhered thereto), wherein the shaped hydrophilic gel material is prepared from a precursor composition that is at least partially polymerized and shaped in a mold having at least two separate wells when in contact with the substrate, wherein the precursor composition comprises:

(a) at least 10 weight percent polar solvent based on the total weight of the precursor composition, wherein the polar solvent comprises water; and (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units.

36. An article comprising a substrate having a shaped hydrophilic gel material disposed thereon (preferably, adhered thereto), wherein the shaped hydrophilic gel material is prepared from a precursor composition that is at least partially polymerized and shaped in a mold having at least two separate wells when in contact with the substrate, wherein the precursor composition comprises:

(a) at least 10 weight percent polar solvent based on the total weight of the precursor composition; and (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units, the poly(alkylene oxide (meth)acrylate) having a weight average molecular weight less than 2,000 g/mole.

37. The article of embodiment 35 or embodiment 36, wherein the precursor composition further comprises an active agent.

38. The article of embodiment 35 or embodiment 36, wherein the shaped hydrophilic gel material comprises an active agent.

39. The article of embodiment 37 or embodiment 38, wherein the active agent comprises a bioactive agent.

40. The article of any one of embodiments 35 through 39, wherein the shaped hydrophilic gel material is swollen with a polar solvent.

41. The article of embodiment 40 wherein the polar solvent comprises water.

42. The article of any one of embodiments 35 through 39, wherein the shaped hydrophilic gel material is in a dried form.

43. An article comprising a substrate having a coating of a hydrophilic gel material disposed thereon (preferably, adhered thereto), wherein the hydrophilic gel material is prepared from a precursor composition that is at least partially polymerized when in contact with the substrate, and wherein the precursor composition comprises:

(a) at least 5 weight percent polar solvent based on a total weight of the precursor composition; and (b) polymerizable material capable of free-radical polymerization and having an average number of ethylenically unsaturated groups per molecule greater than 1.0, wherein the polymerizable material is miscible with the polar solvent.

44. The article of embodiment 43, wherein the precursor composition comprises:

(a) greater than 10 weight percent polar solvent based on a total weight of the precursor composition; and (b) polymerizable material capable of free-radical polymerization and having an average number of ethylenically unsaturated groups per molecule equal to at least 1.2.

45. The article of embodiment 43, wherein the precursor composition comprises:
   (a) at least 10 weight percent polar solvent based on the total weight of the precursor composition, wherein the polar solvent comprises water; and
   (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material comprises a poly(alkylene oxide (meth)acrylate) having at least 2 (meth) acryloyl groups and having at least 5 alkylene oxide units.
46. The article of embodiment 43, wherein the precursor composition comprises:
   (a) at least 10 weight percent polar solvent based on the total weight of the precursor composition; and
   (b) no greater than 90 weight percent polymerizable material based on the total weight of the precursor composition, the polymerizable material being capable of free-radical polymerization and having an average number of ethylenically unsaturated groups per molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units and the poly(alkylene oxide (meth)acrylate) having a weight average molecular weight less than 2,000 g/mole.
47. The article of embodiment 43, wherein the precursor composition comprises:
   (a) greater than 10 weight percent polar solvent based on a total weight of the precursor composition; and
   (b) less than 90 weight percent polymerizable material based on the total weight of the precursor composition, the polymerizable material being capable of free-radical polymerization and having an average number of ethylenically unsaturated groups per molecule equal to at least 1.2, the polymerizable material being miscible in the polar solvent and comprising
      i) a poly(alkylene oxide (meth)acrylate) having at least 2 (meth)acryloyl functional groups and having at least 5 alkylene oxide units; and
      ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof
48. The article of any one of embodiments 43 through 47, wherein the coating is applied by a non-contact deposition technique.
49. The article of embodiment 48, wherein the coating formed is a discontinuous coating.
50. The article of any one of embodiments 43 through 49, wherein the precursor composition further comprises an active agent.
51. The article of any one of embodiments 43 through 50, wherein the coating of hydrophilic gel material comprises an active agent.
52. The article of embodiment 50 or embodiment 51, wherein the active agent comprises a bioactive agent.
53. The article of any one of embodiments 43 through 52, wherein the coating of hydrophilic gel material is swollen with a polar solvent.
54. The article of embodiment 53 wherein the polar solvent comprises water.
55. The article of any one of embodiments 43 through 52, wherein the coating of hydrophilic gel material is in a dried form.
56. The article of any one of embodiments 35 through 55, wherein the polymerizable material comprises a poly (alkylene oxide (meth) acrylate) having at least 3 (meth) acryloyl groups.
57. The article of any one of embodiments 35 through 56, wherein the precursor composition further comprises a photoinitiator.
58. The article of embodiment 57, wherein the photoinitiator is 2-hydroxy-1-[4-(2-hydroxyethoxy)phenyl]-2-methyl-1-propanone.
59. The article of any one of embodiments 33 through 58, which is a medical article comprising the hydrophilic gel material in a layered format.
60. The article of embodiment 59, which is a wound dressing.
61. The article of embodiment 60, wherein the wound dressing comprises a fluid permeable facing layer and/or a moisture vapor permeable backing layer with the hydrophilic gel layer attached thereto.
62. The article of embodiment 61, wherein the backing layer is both moisture vapor permeable and liquid impermeable.
63. The article of any one of embodiments 60 through 62, wherein the wound dressing further comprises a layer of pressure sensitive adhesive to secure the dressing to the skin.
64. The article of any one of embodiments 60 through 63, wherein the wound dressing comprises an active agent selected from the group consisting of a metal-containing compound, a fatty-acid monoester, a chlorhexidine, triclosan, a peroxide, iodine, complexes thereof, derivatives thereof, and combinations thereof
65. The article of any one of embodiments 60 through 64, wherein the wound dressing comprises chlorhexidine gluconate.

Exemplary Shaped Hydrophilic Gel Materials Embodiments

I-1. A method of making an article comprising a substrate and a shaped hydrophilic gel material disposed thereon, the method comprising:
   providing a precursor composition comprising:
      (a) at least 10 weight percent polar solvent based on the total weight of the precursor composition, wherein the polar solvent comprises water; and
      (b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth) acrylate) having at least 2 (meth)acryloyl groups and having at least 5 alkylene oxide units;
   providing a mold having at least two separate wells;
   adding the precursor composition to the mold, the precursor composition being positioned in at least a portion of at least two separate wells;
   providing a substrate and positioning the substrate to at least partially contact the precursor composition; and exposing the precursor composition within the wells to radiation to at least partially polymerize the polymerizable material and to form a first swollen shaped hydrophilic gel material on a substrate.

I-2. A method of making an article comprising a substrate and a shaped hydrophilic gel material disposed thereon, the method comprising:
   providing a precursor composition comprising:
   (a) at least 10 weight percent polar solvent based on the total weight of the precursor composition, wherein the polar solvent comprises water; and
   (b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units;
   providing a mold having a substrate in contact therewith in a manner to form at least two separate wells;
   adding the precursor composition to the mold, the precursor composition being positioned in at least a portion of at least two separate wells; and
   exposing the precursor composition within the wells to radiation to at least partially polymerize the polymerizable material and to form a first swollen shaped hydrophilic gel material on a substrate.

I-3. A method of making an article comprising a substrate and a hydrophilic gel material disposed thereon, the method comprising
   providing a precursor composition comprising:
   (a) greater than (or at least) 10 weight percent polar solvent based on a total weight of the precursor composition; and
   (b) polymerizable material (preferably no great than 90 wt-%, based on the total weight of the precursor composition) capable of free-radical polymerization and having an average number of ethylenically unsaturated groups per monomer molecule equal to at least 1.2, wherein the polymerizable material is miscible with (or forms a single phase with) the polar solvent (and preferably comprises a poly(alkylene oxide (meth) acrylate) having at least 2 (meth)acryloyl groups and having at least 5 alkylene oxide units, the poly(alkylene oxide (meth)acrylate) having a weight average molecular weight less than 2,000 g/mole);
   providing a mold having at least two separate wells;
   adding the precursor composition to the mold, the precursor composition being positioned in at least a portion of at least two separate wells;
   providing a substrate and positioning the substrate to contact the precursor composition; and
   exposing the precursor composition within the wells to radiation to at least partially polymerize the polymerizable material and to form a first swollen shaped hydrophilic gel material on a substrate.

I-4. A method of making an article comprising a substrate and a hydrophilic gel material disposed thereon, the method comprising
   providing a precursor composition comprising:
   (a) at least 5 (or at least 10) weight percent polar solvent based on a total weight of the precursor composition; and
   (b) polymerizable material (preferably no great than 90 wt-%, based on the total weight of the precursor composition) capable of free-radical polymerization and having an average number of ethylenically unsaturated groups per monomer molecule greater than 1.0 (preferably equal to at least 1.2), wherein the polymerizable material is miscible with (or forms a single phase with) the polar solvent (and preferably comprises a poly(alkylene oxide (meth)acrylate) having at least 2 (meth)acryloyl groups and having at least 5 alkylene oxide units, the poly(alkylene oxide (meth)acrylate) having a weight average molecular weight less than 2,000 g/mole);
   providing a mold having a substrate in contact therewith in a manner to form at least two separate wells;
   adding the precursor composition to the mold, the precursor composition being positioned in at least a portion of at least two separate wells; and
   exposing the precursor composition within the wells to radiation to at least partially polymerize the polymerizable material and to form a first swollen shaped hydrophilic gel material on a substrate.

I-5. The method of embodiment I-3 or I-4 wherein the polymerizable material comprises a poly(alkylene oxide (meth)acrylate) having an average number of (meth) acryloyl groups per monomer molecule equal to at least two.

I-6. The method of any one of embodiments I-1 through I-5 wherein the poly(alkylene oxide (meth)acrylate) has a weight average molecular weight no greater than 2000 g/mole.

I-7. The method of any one of embodiments I-1 through I-6, wherein the polymerizable material comprises a poly (alkylene oxide (meth) acrylate) having at least 3 (meth) acryloyl groups.

I-8. The method of any one of embodiments I-1 through I-7, wherein the precursor composition further comprises a photoinitiator and the radiation comprises actinic radiation.

I-9. The method of any one of embodiments I-1 through I-8, further comprising removing the first swollen shaped hydrophilic gel material and substrate from the mold.

I-10. The method of embodiment I-9, wherein removing the first swollen shaped hydrophilic gel material comprises applying a polar solvent to the first swollen hydrophilic gel material.

I-11. The method of any one of embodiments I-1 through I-10, further comprising removing at least a portion of the polar solvent from the first swollen shaped hydrophilic gel material to form a dried shaped hydrophilic gel material.

I-12. The method of embodiment I-11, further comprising contacting the dried shaped hydrophilic gel material with a sorbate for a time sufficient for the dried shaped hydrophilic gel material to sorb at least a portion of the sorbate to form a second swollen shaped hydrophilic gel material, wherein the sorbate comprises at least one active agent.

I-13. The method of embodiment I-12, wherein the at least one active agent in the sorbate comprises a bioactive agent.

I-14. The method of embodiment I-12, further comprising drying the second swollen shaped hydrophilic gel material.

I-15. The method of any one of embodiments I-1 through I-14, wherein adding the precursor composition to the mold comprises overfilling the at least two separate wells, wherein the precursor composition resides on a first surface of the mold between the wells.

I-16. The method of any one of embodiments I-1 through I-15, wherein the precursor composition further comprises an active agent.

I-17. The method of embodiment I-16, wherein the active agent in the precursor composition comprises a bioactive agent.

I-18. The method of any one of embodiments I-17, wherein the precursor composition is at least partially exposed to radiation through the substrate.

I-19. An article comprising a substrate and a shaped hydrophilic gel material disposed thereon, the article made by the method of any one of embodiments I-1 through I-18.

I-20. An article comprising a substrate having a shaped hydrophilic gel material disposed thereon, wherein the shaped hydrophilic gel material is prepared from a precursor composition that is at least partially polymerized and shaped in a mold having at least two separate wells, wherein the precursor composition comprises:
(a) at least 10 weight percent polar solvent based on the total weight of the precursor composition, wherein the polar solvent comprises water; and
(b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units.

I-21. An article comprising a substrate having a shaped hydrophilic gel material disposed thereon, wherein the shaped hydrophilic gel material is prepared from a precursor composition that is at least partially polymerized and shaped in a mold having at least two separate wells, wherein the precursor composition comprises:
(a) at least 10 weight percent polar solvent based on the total weight of the precursor composition; and
(b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units, the poly(alkylene oxide (meth)acrylate) having a weight average molecular weight less than 2,000 g/mole.

I-22. The article of embodiment I-20 or I-21, wherein the precursor composition further comprises an active agent.

I-23. The article of embodiment I-22, wherein the active agent in the precursor composition comprises a bioactive agent.

I-24. The article of embodiment I-20 or I-21, wherein the shaped hydrophilic gel material comprises an active agent.

I-25. The article of embodiment I-24, wherein the active agent in the shaped hydrophilic gel material comprises a bioactive agent.

I-26. The article of any one of embodiments I-20 through I-25, wherein the polymerizable material comprises a poly(alkylene oxide (meth) acrylate) having at least 3 (meth)acryloyl groups.

I-27. The article of any one of embodiments I-20 through I-26, wherein the precursor composition further comprises a photoinitiator.

I-28. The article of any one of embodiments I-20 through I-27, wherein the shaped hydrophilic gel material is swollen with a polar solvent.

I-29. The article of embodiment I-28, wherein the polar solvent comprises water.

I-30. The article of any one of embodiments I-20 through I-29, wherein the shaped hydrophilic gel material is in a dried form.

I-31. The article of any one of embodiments I-20 through I-30, which is a medical article comprising the shaped hydrophilic gel material in a layered format.

I-32. The article of embodiment I-31 which is a wound dressing.

I-33. The article of embodiment I-32, wherein the wound dressing comprises a fluid permeable facing layer and/or a moisture vapor permeable backing layer with the shaped hydrophilic gel layer attached thereto.

I-34. The article of embodiment I-33, wherein the backing layer is both moisture vapor permeable and liquid impermeable.

I-35. The article of any one of embodiments I-32 through I-34, wherein the wound dressing further comprises a layer of pressure sensitive adhesive to secure the dressing to the skin.

Exemplary Non-contact Deposition and Discontinuous Coating Embodiments

II-1. A method of making an article comprising a substrate and a hydrophilic gel material disposed thereon, the method comprising
providing a precursor composition comprising:
(a) at least 10 weight percent polar solvent based on the total weight of the precursor composition, wherein the polar solvent comprises water; and
(b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth)acryloyl groups and having at least 5 alkylene oxide units;
coating the precursor composition on at least a portion of at least one surface of a substrate by non-contact deposition; and
exposing the precursor composition to radiation to at least partially polymerize the polymerizable material to form a discontinuous coating of first swollen hydrophilic gel material on a substrate.

II-2. A method of making an article comprising a substrate and a hydrophilic gel material disposed thereon, the method comprising
providing a precursor composition comprising:
(a) at least 10 weight percent polar solvent based on the total weight of the precursor composition; and
(b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth) acrylate) having at least 2 (meth)acryloyl groups and having at least 5 alkylene oxide units and the poly(alkylene oxide (meth)acrylate) having a weight average molecular weight less than 2,000 g/mole;

coating the precursor composition on at least a portion of at least one surface of a substrate by non-contact deposition; and exposing the precursor composition to radiation to at least partially polymerize the polymerizable material to provide a discontinuous coating of first swollen hydrophilic gel material on a substrate.

II-3. A method of making an article comprising a substrate and a hydrophilic gel material disposed thereon, the method comprising providing a precursor composition comprising:
(a) greater than 10 weight percent polar solvent based on a total weight of the precursor composition; and
(b) less than 90 weight percent polymerizable material based on the total weight of the precursor composition, the polymerizable material being capable of free-radical polymerization and having an average number of ethylenically unsaturated groups per monomer molecule equal to at least 1.2, the polymerizable material being miscible in the polar solvent and comprising
  i) a poly(alkylene oxide (meth)acrylate) having at least 2 (meth)acryloyl functionality groups and having at least 5 alkylene oxide units; and
  ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof;

coating the precursor composition on at least a portion of at least one surface of a substrate by non-contact deposition; and exposing the precursor composition to radiation to at least partially polymerize the polymerizable material to provide a discontinuous coating of first swollen hydrophilic gel material on a substrate.

II-4. A method of making an article comprising a substrate and a hydrophilic gel material disposed thereon, the method comprising providing a precursor composition comprising:
(a) greater than 10 weight percent polar solvent based on a total weight of the precursor composition; and
(b) polymerizable material capable of free-radical polymerization and having an average number of ethylenically unsaturated groups per monomer molecule equal to at least 1.2, wherein the poloymerizable material is miscible with the polar solvent;

coating the precursor composition on at least a portion of at least one surface of a substrate by non-contact deposition; and exposing the precursor composition to radiation to at least partially polymerize the polymerizable material to provide a discontinuous coating of first swollen hydrophilic gel material on a substrate.

II-5. A method of making an article comprising a substrate and a hydrophilic gel material disposed thereon, the method comprising providing a precursor composition comprising:
(a) at least 5 weight percent polar solvent based on a total weight of the precursor composition; and
(b) polymerizable material capable of free-radical polymerization and having an average number of ethylenically unsaturated groups per monomer molecule greater than 1.0, wherein the polymerizable material is miscible with the polar solvent;

coating the precursor composition on at least a portion of at least one surface of a substrate by non-contact deposition; and exposing the precursor composition to radiation to at least partially polymerize the polymerizable material to provide a discontinuous coating of first swollen hydrophilic gel material on a substrate.

II-6. The method of embodiment II-4 or II-5 wherein the polymerizable material comprises a poly(alkylene oxide (meth)acrylate) having an average number of (meth)acryloyl groups per monomer molecule equal to at least two.

II-7. The method of embodiment II-6 wherein the poly(alkylene oxide (meth)acrylate) has a weight average molecular weight no greater than 2000 g/mole.

II-8. The method of any one of embodiments II-1 through II-7, wherein the precursor composition further comprises an active agent.

II-9. The method of any one of embodiments II-1 through II-8, wherein the polymerizable material comprises a poly(alkylene oxide (meth) acrylate) having at least 3 (meth)acryloyl groups.

II-10. The method of any one of embodiments II-1 through II-9, wherein the precursor composition further comprises a photoinitiator and the radiation comprises actinic radiation.

II-11. The method of any one of embodiments II-1 through II-10, further comprising removing at least a portion of the polar solvent from the first swollen hydrophilic gel material to form a coating of dried hydrophilic gel material.

II-12. The method of any one of embodiments II-1 through II-11, further comprising contacting dried hydrophilic gel material with a sorbate for a time sufficient for the dried hydrophilic gel material to sorb at least a portion of the sorbate to form a discontinuous coating of second swollen hydrophilic gel material II-13. The method of embodiment II-12, wherein the sorbate comprises at least one active agent.

II-14. The method of embodiment II-8 or II-13, wherein the at least one active agent comprises a bioactive agent.

II-15. The method of embodiment II-8 or II-13, wherein the active is selected from a group consisting of a metal-ion forming compound, a fatty-acid monoester, chlorhexidine, triclosan, a peroxide, iodine, complexes thereof, derivatives thereof, and combinations thereof.

II-16. The method of any one of embodiments II-1 through II-15, wherein the non-contact deposition comprises inkjet printing.

II-17. The method of any one of embodiments II-1 through II-16, wherein the non-contact deposition comprises spray atomization deposition.

II-18. An article comprising a substrate and a hydrophilic gel material disposed thereon by non-contact deposition, the article made by the method of any one of embodiments II-1 through II-17.

II-19. An article comprising a substrate having a hydrophilic gel material disposed thereon by non-contact deposition, wherein the hydrophilic gel material is prepared from a precursor composition that is at least partially polymerized and wherein the precursor composition comprises:
(a) at least 10 weight percent polar solvent based on the total weight of the precursor composition, wherein the polar solvent comprises water; and (b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth) acryloyl groups and having at least 5 alkylene oxide units.

II-20. An article comprising a substrate having a hydrophilic gel material disposed thereon by non-contact deposition, wherein the hydrophilic gel material is prepared from a precursor composition that is at least partially polymerized and wherein the precursor composition comprises:

(a) at least 10 weight percent polar solvent based on the total weight of the precursor composition; and (b) no greater than 90 weight percent polymerizable material based on the total weight of the precursor composition, the polymerizable material being capable of free-radical polymerization and having an average number of ethylenically unsaturated groups per monomer molecule equal to at least 1.2, wherein the polymerizable material forms a single phase with the polar solvent and comprises a poly(alkylene oxide (meth)acrylate) having at least 2 (meth) acryloyl groups and having at least 5 alkylene oxide units, the poly(alkylene oxide (meth)acrylate) having a weight average molecular weight less than 2,000 g/mole.

II-21. An article comprising a substrate having a hydrophilic gel material disposed thereon by non-contact deposition, wherein the hydrophilic gel material is prepared from a precursor composition that is at least partially polymerized and wherein the precursor composition comprises:

(a) greater than 10 weight percent polar solvent based on a total weight of the precursor composition; and (b) less than 90 weight percent polymerizable material based on the total weight of the precursor composition, the polymerizable material being capable of free-radical polymerization and having an average number of ethylenically unsaturated groups per monomer molecule equal to at least 1.2, the polymerizable material being miscible in the polar solvent and comprising i) a poly(alkylene oxide (meth)acrylate) having at least 2 (meth)acryloyl functionality groups and having at least 5 alkylene oxide units; and ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof.

II-22. An article comprising a substrate having a hydrophilic gel material disposed thereon by non-contact deposition, wherein the hydrophilic gel material is prepared from a precursor composition that is at least partially polymerized and wherein the precursor composition comprises:

(a) greater than 10 weight percent polar solvent based on a total weight of the precursor composition; and (b) polymerizable material capable of free-radical polymerization and having an average number of ethylenically unsaturated groups per monomer molecule equal to at least 1.2, wherein the poloymerizable material is miscible with the polar solvent.

II-23. An article comprising a substrate having a hydrophilic gel material disposed thereon by non-contact deposition, wherein the hydrophilic gel material is prepared from a precursor composition that is at least partially polymerized and wherein the precursor composition comprises:

(a) at least 5 weight percent polar solvent based on a total weight of the precursor composition; and (b) polymerizable material capable of free-radical polymerization and having an average number of ethylenically unsaturated groups per monomer molecule greater than 1.0, wherein the polymerizable material is miscible with the polar solvent.

II-24. The article of any one of embodiments II-19 through II-23, wherein the precursor composition further comprises an active agent.

II-25. The article of embodiment II-24, wherein the active agent in the precursor composition comprises a bioactive agent.

II-26. The article of any one of embodiments II-19 through II-23, wherein the hydrophilic gel material comprises an active agent.

II-27. The article of embodiment II-26, wherein the active agent in the hydrophilic gel material comprises a bioactive agent.

II-28. The article of any one of embodiments II-19 through II-23, wherein the polymerizable material comprises a poly(alkylene oxide (meth) acrylate) having at least 3 (meth)acryloyl groups.

II-29. The article of any one of embodiments II-19 through II-23, wherein the precursor composition further comprises a photoinitiator.

II-30. The article of any one of embodiments II-19 through II-23, wherein the hydrophilic gel material is swollen with a polar solvent.

II-31. The article of embodiment II-30 wherein the polar solvent comprises water.

II-32. The article of any one of embodiments II-19 through II-23, wherein the hydrophilic gel material is in a dried form.

II-33. The article of embodiments II-18 through II-32 which is a wound dressing.

II-34. The article of embodiments II-25 through II-33, wherein the at least one bioactive agent comprises chlorohexidine gluconate.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Test Methods

Zone of Inhibition Inoculated Agar Assay Method (I)

An inoculum suspension of *Staphyloccoccus epidermidis* (ATCC 12228) (American Type Culture Collection, Manassas, Va.) of approximately $1 \times 10^5$ colony forming unit (CFU) per milliliter was prepared in Phosphate Buffered Water (PBW) using a 0.5 McFarland Equivalence Turbidity Standard. A uniform bacterial concentration in agar was created by mixing twenty milliliters of the suspension with the agar of a Meuller Hinton plate. Disks (24-mm in diameter) of the substrate to be tested were placed on the agar plate, with the test composition facing the agar, and firmly pressed against the agar to insure sample to agar contact across the entire sample surface. Two disks were placed on each plate for zone analysis. The plates were incubated at 36° C.±1° C. for 24 hours. The average diameter of the inhibited zone was recorded for each disk.

Zone of Inhibition Test Method (II)

An inoculum suspension of either gram positive (*Staphylococcus aureus*, ATCC 6538, American Type Culture Collection, Manassas, Va.), or gram negative (*Pseudomonas aeruginosa* (ATCC 9027) was prepared that contained a concentration of approximately $1\times10^8$ colony forming units (CFU) per milliliter (mL) in Phosphate Buffered Saline (PBS) obtained from EMD Biosciences of Darmstadt, Germany, using a 0.5 McFarland Equivalence Turbidity Standard. A bacterial lawn was prepared by dipping a sterile cotton applicator into the suspension and swabbing the dry surface of a trypticase soy agar (TSA) plate in three different directions. Three 7-mm paper disks were prepared for each sample, placed onto the inoculated plate of each media type, and pressed firmly against the agar with sterile forceps to ensure complete contact with the agar. The plates were incubated at 4° C. for 3 hours and the incubated at 36° C.±1° C. for 24 hours. The area under and surrounding the samples was examined for bacterial growth. The reported results were the average values of the diameter of the circles surrounding each sample where no growth was observed. For example, a zone of 7 indicates that no growth was observed underneath the 7-mm disk, and a zone of 9 indicates that no growth was observed underneath the 7-mm disk, as well as in an area surrounding the disk, where the total diameter of the no growth area (i.e., including the area under the disk) was 9 mm.

I. Shaped Material Examples

Example I-1

Shaped Polymeric Material Film

A precursor composition was prepared by mixing 3.96 g of 20-mole ethoxylated trimethylolpropane triacrylate (TMPTA, SR-415), 6 grams of deionized water, and 0.4 grams photoinitiator (IRGACURE 2959) in a container. The precursor composition was heated for 2 minutes at 70° C. to dissolve the photoinitiator.

The precursor composition was poured onto a planar silicone rubber mold (GI-1000 silicone base, Sterling Supply Co., Minneapolis, Minn.) having a regular hexagonal pattern embedded in it. Each hexagon defined a well with opposite sides spaced 3 millimeters (mm) apart and a well depth of 1 mm. Wells were spaced 2.5 mm apart. A backing film of corona-treated polyethylene (112 microns) was laminated to the mold forcing the precursor composition to fill the individual wells. The multilayer structure was then passed under a 240 W/cm Fusion H bulb at 8 meters/minute, exposing the precursor composition through the backing film. The cured composition of shaped polymeric material adhered to the cover film was peel lifted out the mold. The composition comprising the cover film and partially solidified shaped hydrophilic gel materials was then passed through the UV processor with the polymeric material side facing the UV processor at 8 meters/minute under a nitrogen purge to complete the cure.

Example I-2

Example I-1 was repeated except the polyethylene cover film was replaced by a primed polyethylene terephtalate (PET) film (50 microns) (available under the trade designation SCOTCHPAR brand Type PH Polyester Film from Minnesota Mining and Manufacturing Co., St. Paul, Minn.). The final product was a PET film with individual raised hexagonal hydrogel features.

Example I-3

Example I-1 was repeated using a mold having the negative of a regular hexagonal pattern with opposite sides 15 mm apart, a depth of 1 mm, and a nearest neighbor spacing of 5 mm. The final product was a polyethylene film with a raised pattern of hydrogel replicating the channels between hexagons in the original mold.

Example I-4

Example I-1 was repeated using a mold having a regular cylindrical pattern with individual cylinders 1 mm in diameter and 1 mm deep with a 0.5 mm pattern width. The final product was a polyethylene film with raised individual cylinders.

Example I-5

The procedure of Example I-4 was repeated but the precursor composition consisted of a blend of 39.6 wt-% 20-mole ethoxylated TMPTA, 0.4 wt-% IRGACURE 2959, 4.0 wt-% chlorhexidine gluconate (CHG) and 56 wt-% water. The Zone of Inhibition Inoculated Agar Assay Method (I) was used with *Staphylococcus epidermidis* as the test organism to determine antimicrobial effectiveness. The 3-mm width hexagon structures on PET film produced zones of inhibition approximately 32-mm in diameter indicating excellent cidal activity.

Example I-6

Example I-5 was repeated using a silicone mold having a linear grooved pattern with channels 0.5 mm in height and width with a pattern spacing of 0.5 mm. Upon removal from the mold, the surface of the PET film contacting the mold showed a linear bar pattern of raised hydrogel containing CHG.

II. Non-Contact Deposition Examples

Example II-1

A hydrogel precursor composition consisting of 39.6% SR415 (ethoxylated (20) trimethylolpropane triacrylate), 0.4% IRGACURE 2959 (2-hydroxy-1-[4-(2-hydroxyethoxyl)phenyl]-2-methyl-1-propanone), 4% chlorhexidine gluconate and 56% deionized water was poured into the reservoir of a Model 9306 Six-Jet Atomizer from TSI, Inc. (Shoreview, Minn.). A piece of tubing was used to extend the exit port of the atomizer and invert it to a downward position. The exit from the tube was positioned about 2 centimeters above a conveyor belt. An air-pressure of 30 pounds per square inch (psi) was used to atomize the antimicrobial-containing hydrogel precursor solution through all six nozzles. A non-woven rayon backing (as described by U.S. Pat. No. 3,121,021) to be non-contact printed with antimicrobial-containing hydrogel droplets was placed on the conveyor belt and passed under the exit tube at a speed of 0.7 meter/minute such that the substrate came in contact with a fog consisting of the atomized droplets. An exhaust trunk removed the excess droplets. The coated substrate was then exposed under a bank of fluorescent 365 nm bulbs having a peak UVA irradiance of 38 mW/cm² for approximately 60 seconds in a nitrogen atmosphere.

Example II-2

A sample prepared in the same fashion of Example II-1, except that the substrate in Example II-2 was a polyurethane available from Noveon, Inc., Cleveland, Ohio extrusion coated on a carrier as further described by U.S. Pat. No. 4,598,004 and commercially available from Wausau-Mosinee Paper Corp. (Paper No. 78, silicone C15 SC RLFE B13E/SH11).

Example II-3

A sample prepared in the same fashion of Example II-1, except that the substrate in Example II-3 comprised an IOA/acrylamide (97/3) adhesive coated on one surface of the substrate of Example II-2. The hydrogel was coated onto the adhesive side. The adhesive IOA/Acrylamide (97/3) was made in accordance with U.S. Pat. No. 4,693,776 and coated at 25 grams/square meter coating weight. This sample was tested using the Zone of Inhibition Inoculated Agar Assay Method (I). The primary zone was 32 mm in diameter indicating good antimicrobial activity. A hydrogel antimicrobial discontinuously coated on an adhesive dressing would have the ability to adhere to the skin, the ability to absorb perspiration or wound exudate, and have antimicrobial characteristics to minimize the potential for infection.

Example II-4

Preparation of Printed Substrates

The hydrogel precursor composition selected for this example was a 40 wt-% solution of 20-mole ethoxylated trimethylolpropane triacrylate ($EO_{20}TMPTA$) containing 1 wt-% IRGACURE 2959 in deionized water. The solution had a Brookfield viscosity of 10 cps.

The print head was a Spectra SE-128 AA head (S/N 120086), available from Dimatix Technology Integration, Lebanon, N.H. This head has 128 nozzles and a droplet volume of 30 pL when fired under standard test conditions at the calibrated fire pulse amplitude. The jet velocity can range from 8 to 12 meters/second depending on firing frequency. The fire pulse amplitude was 100 V, the rise time was 1.8 microseconds (µs), the pulse width was 5.8 µs, and a fall time was 0.5 µs. The nozzle face was positioned 8 mm above the print media during printing. Two print media were coated. One was coated on 3M CONTROLTAC PLUS GRAPHIC FILM IJ180C-10 (commercially available from Minnesota Mining and Manufacturing Co., St. Paul, Minn.) and the other on paper.

Figure 7:
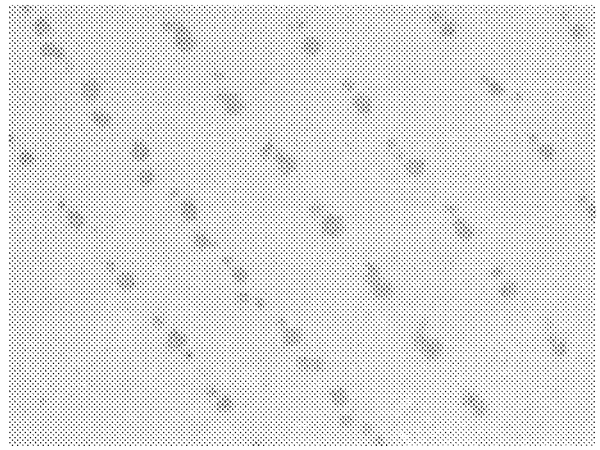
FIG. 7 is a micrograph of a hydrophilic gel material coated on a substrate by ink jet printing.
Figure 8:
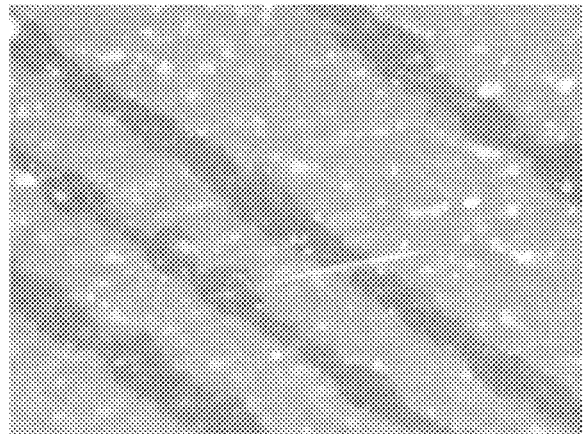
FIG. 8 is a micrograph of a hydrophilic gel material coated on a substrate by ink jet printing.

The hydrogel precursor composition was non-contact deposited (jetted) at room temperature. Multiple samples were created at 1, 5, 10, 15 and 20 kHz frequencies on the print head. The resulting samples were cured in air on a UV processor with two 80 W/cm mercury lamps at a belt speed at 20 meters/minute. FIG. 7 and FIG. 8 show micrographs of a hydrophilic gel material coated on a substrate by ink jet printing at 1 kHz, stained with methylene blue solution and 20 kHz, wetted with methylene blue solution, respectively.

Example II-5

Preparation of Active-Containing Hydrogel Coatings

Samples were jetted and cured in the same fashion as Example II-4 onto a 100-micron biaxially oriented polyester film (PET) (available under the trade designation SCOTCH-PAR brand Polyester Film from Minnesota Mining and Manufacturing Co., St. Paul, Minn.). These samples were dried in a vacuum oven at 90° C. for 2 hours to remove water. The following aqueous test solutions were prepared:
1. 8% cetylpyridinium chloride (CPC)
2. 8% benzalkonium chloride (BAC)

Upon removal from the oven, each sample was cut into a series of approximately 1-cm wide strips. Individual dried strips were placed into 50 milliliter plastic centrifuge tubes containing approximately 45 milliliters of a range of active solutions and the tubes were capped. The actives were allowed to diffuse into the dried hydrogel strips. The sealed tubes containing the strips and test solutions were gently agitated for 2.5 minutes to allow sorption of the test solution into the jetted and dried hydrogel droplets. The individual strips were then removed and washed in tap water for approximately 60 seconds followed by a 15-second rinse in distilled water. Strips were packaged separately by test solution to eliminate any sample cross contamination.

The strips were die cut into 15 millimeter (mL) disks. The disks were placed in wells containing 500 microliter (µL) phosphate-buffered water (PBW) and incubated at 35° C. for 30 minutes. Then 500 µL TSB (trypticase soy broth) containing approximately 44 CFU/mL *S. epidermidis* (ATCC #12228) was added to each well and incubated overnight at 35° C. Growth of bacteria was scored, and the broths were transferred to new wells for another overnight incubation to confirm growth/no growth. The results are shown in Table I below.

TABLE I

| Broth | 24 hrs | 48 hrs |
|---|---|---|
| Broth sterility control | −/− | −/− |
| Growth control | +/+ | +/+ |
| PBS sterility control | −/− | −/− |
| Backing control (no hydrogel, no antimicrobial) | ±/+/± | +/+/+ |
| Hydrogel control (backing + hydrogel, no antimicrobial) | +/+/± | +/+/+ |
| BAC soaked control | ±/± | +/+ |
| BAC 20 kHz | −/− | −/− |
| BAC 10 kHZ | −/− | −/± |
| BAC 8 kHz | −/± | +/+ |
| BAC 5 kHz | ±/± | +/+ |
| BAC 1 kHz | ±/± | +/+ |
| CPC soaked control | ±/± | +/+ |
| CPC 20 kHz | −/− | −/− |
| CPC 10 kHz | −/− | −/− |
| CPC 8 kHz | −/− | −/− |
| CPC 5 kHz | −/− | −/− |
| CPC 1 kHz | −/− | −/− |

+ means turbidity indicating growth
− means no turbidity/clear indicating no growth
± means some turbidity indicating some growth The growth control samples, which consisted of the polyester backing (PET substrate) and hydrogel coated backing showed no antimicrobial activity. Samples containing the cetylpyridinium chloride (CPC) all had excellent antimicrobial activity. For the benzalkonium chloride samples, the higher frequencies showed antimicrobial activity due to the increased amount of hydrogel deposited and antimicrobial absorbed.

Example II-6

In-line Curing of Inkjet Printed Antimicrobial Hydrogels

Antimicrobial solution was prepared by mixing 10 parts Bronopol (Trade designation MYACIDE AS PLUS), commercially available from BASF (Germany) with 30 parts isopropyl alcohol. A precursor composition (Sample A) was prepared by mixing 40 parts SR415, 20 parts water, 40 parts of the antimicrobial solution, and 2 parts photoinitiator IRGACURE 2959. A control precursor composition (Sample B) was prepared by mixing 40 parts SR415, 30 parts isopropyl alcohol, 30 parts water, and 2 parts photoinitiator IRGACURE 2959.

The two compositions were applied by inkjet printing at 10% surface coverage onto the Spunlace SX-156 substrate (23-cm x 23-cm available from VWR International, West Chester, Pa.) with a "XAAR XJ128-200 printhead." The printhead was peizoelectrically driven at 1.25 kHz and 35 V, with a printing resolution of 300×300 dpi. This generated drops of the fluid solution with nominal volumes of about 70 pL. The inkjetted solution was UV cured in-line using the EFOS ULTRACURE 100SS PLUS UV Light Curing System (Wavelength range: 320-500 nm) attached to the printhead. EFOS is a spot Cure UV-Vis system available from EXFO Electro-Optical Engineering Inc. (Quebec City, Canada).

Examination with light microscope showed that the hydrogel drops were about 100-120 micron in diameter, and they were deposited as discrete drops upon the Spunlace Substrate. Zone of inhibition testing was performed on Spunlace that was inkjet coated with Sample A and Sample B. Seven millimeter (7-mm) disks were applied onto agar plates that were innoculated with either *Staphylococcus aureus* or *Pseudomonas aeruginosa* as described in the Zone of Inhibition Test Method (II). The control sample, Sample B (no Myacide AS) did not show any zone with heavy growth of bacteria under the sample disks. Sample A, which contained Myacide AS, showed a 13-mm zone with *Staphylococcus aureus* and an 11-mm zone with *Pseudomonas aeruginosa.*

III. Contact Deposition Examples

Example III-1

Preparation of a Continuous Hydrogel Coating on a Film

A solution comprising 39.6 wt-% SR415 and 0.4 wt-% IRGACURE 2959 in water was coated using a No. 6 Mayer rod onto a corona-treated PET film (SCOTCHPAR brand polyester film from Minnesota Mining and Manufacturing Co., St. Paul, Minn., corona treated at 15 meters/minute at a 0.8 kW power level in air). The coating was cured at 15 meters/minute in a nitrogen atmosphere using a Fusion 240 W/cm H bulb. The cured coating was dry to the touch and had moderate adhesion to the substrate.

Various modifications and alterations of this disclosure will be apparent to those skilled in the art without departing from the scope and spirit of this disclosure, and it should be understood that this disclosure is not limited to the illustrative elements set forth herein. All patents and publications cited herein are incorporated by reference in their entirety as if individually incorporated.

What is claimed is:

1. A method of making an article comprising a substrate and a hydrophilic gel material adhered thereto, the method comprising:
   providing a precursor composition comprising:
   (a) at least 10 weight percent polar solvent based on a total weight of the precursor composition, wherein the polar solvent comprises water; and
   (b) polymerizable material capable of free-radical polymerization and having an average number of ethylenically unsaturated groups per molecule of polymerizable material equal to at least 1.2 relative to total polymerizable material, wherein the polymerizable material is miscible with the polar solvent and wherein the polymerizable material comprises a poly(alkylene oxide (meth)acrylate) having at least 2 (meth)acryloyl groups and having at least 5 alkylene oxide units;
   wherein the precursor composition comprises no greater than 90 weight percent polymerizable material based on the total weight of the precursor composition
   providing a mold having at least two separate wells;
   adding the precursor composition to the mold, the precursor composition being positioned in at least a portion of at least two separate wells;
   providing a substrate and positioning the substrate to at least partially contact the precursor composition; and
   exposing the precursor composition within the wells to radiation to at least partially polymerize the polymerizable material and to form a first swollen shaped hydrophilic gel material adhered to the substrate.

2. A method of making an article comprising a substrate and a hydrophilic gel material adhered thereto, the method comprising:
   providing a precursor composition comprising:
   (a) at least 10 weight percent polar solvent based on a total weight of the precursor composition, wherein the polar solvent comprises water; and
   (b) polymerizable material capable of free-radical polymerization and having an average number of ethylenically unsaturated groups per molecule of polymerizable material equal to at least 1.2 relative to total polymerizable material, wherein the polymerizable material is miscible with the polar solvent and wherein the polymerizable material comprises a poly(alkylene oxide (meth)acrylate) having at least 2 (meth)acryloyl groups and having at least 5 alkylene oxide units;
   wherein the precursor composition comprises no greater than 90 weight percent polymerizable material based on the total weight of the precursor composition;
   providing a mold having a substrate in contact therewith in a manner to form at least two separate wells;
   adding the precursor composition to the mold, the precursor composition being positioned in at least a portion of at least two separate wells; and
   exposing the precursor composition within the wells to radiation to at least partially polymerize the polymerizable material and to form a first swollen shaped hydrophilic gel material adhered to the substrate.

3. A method of making an article comprising a substrate and a hydrophilic gel material adhered thereto, the method comprising:
   providing a precursor composition comprising:
   (a) at least 10 weight percent polar solvent based on a total weight of the precursor composition; and
   (b) polymerizable material capable of free-radical polymerization and having an average number of ethylenically unsaturated groups per molecule of polymerizable material equal to at least 1.2 relative to total polymerizable material, wherein the polymerizable material is miscible with the polar solvent and forms a single phase with the polar solvent and comprises a poly(alkylene oxide (meth)acrylate) having at least 2 (meth)acryloyl groups and having at least 5 alkylene oxide units and the poly(alkylene oxide (meth)acrylate) having a weight average molecular weight less than 2,000 g/mole;

wherein the precursor composition comprises no greater than 90 weight percent polymerizable material based on the total weight of the precursor composition;

coating the precursor composition on at least a portion of at least one surface of a substrate; and exposing the precursor composition to radiation to at least partially polymerize the polymerizable material to provide a coating of first swollen hydrophilic gel material adhered to the substrate.

4. The method of claim 3, wherein the precursor composition comprises:
  (a) greater than 10 weight percent polar solvent based on a total weight of the precursor composition; and
  (b) less than 90 weight percent polymerizable material based on the total weight of the precursor composition, the polymerizable material being miscible in the polar solvent and comprising:
    i) a poly(alkylene oxide (meth)acrylate) having at least 2 (meth)acryloyl functional groups and having at least 5 alkylene oxide units; and
    ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof.

5. The method of claim 3, wherein:
coating the precursor composition comprises using a non-contact deposition technique; and
exposing the precursor composition to radiation to at least partially polymerize the polymerizable material to provide a coating of first swollen hydrophilic gel material on a substrate comprises forming a discontinuous coating of first swollen hydrophilic gel material on at least a portion of at least one surface of a substrate.

6. The method of claim 5, wherein the non-contact deposition comprises inkjet printing.

7. The method of claim 5, wherein the non-contact deposition comprises spray atomization deposition.

8. The method of claim 3, wherein the precursor composition further comprises an active agent.

9. A method of making an article comprising a substrate and a hydrophilic gel material adhered thereto, the method comprising:
providing a precursor composition comprising:
  (a) at least 10 weight percent polar solvent based on a total weight of the precursor composition, wherein the polar solvent comprises water; and
  (b) polymerizable material capable of free-radical polymerization and having an average number of ethylenically unsaturated groups per molecule of polymerizable material equal to at least 1.2 relative to total polymerizable material, wherein the polymerizable material is miscible with the polar solvent, wherein the polymerizable material comprises a poly(alkylene oxide (meth)acrylate) having at least 2 (meth)acryloyl groups and having at least 5 alkylene oxide units;
  wherein the precurser composition comprises no greater than 90 weight percent polymerizable material based on the total weight of the precursor composition;
coating the precursor composition on at least a portion of at least one surface of a substrate; and
exposing the precursor composition to radiation to at least partially polymerize the polymerizable material to provide a coating of first swollen hydrophilic gel material adhered to the substrate.

10. A method of making an article comprising a substrate and a hydrophilic gel material adhered thereto, the method comprising:
providing a precursor composition comprising:
  (a) at least 10 weight percent polar solvent based on a total weight of the precursor composition; and
  (b) polymerizable material capable of free-radical polymerization and having an average number of ethylenically unsaturated groups per molecule of polymerizable material equal to at least 1.2 relative to total polymerizable material, wherein the polymerizable material is miscible with the polar solvent, and wherein the polymerizable material comprises:
    i) a poly(alkylene oxide (meth)acrylate) having at least 2 (meth)acryloyl functional groups and having at least 5 alkylene oxide units; and
    ii) 0 to less than 20 weight percent anionic monomer based on a total weight of polymerizable material in the precursor composition, wherein the anionic monomer comprises an ethylenically unsaturated group in addition to an acidic group, a salt of the acidic group, or a mixture thereof;
  wherein the precursor composition comprises less than 90 weight percent polymerizable material based on the total weight of the precursor composition
coating the precursor composition on at least a portion of at least one surface of a substrate; and
exposing the precursor composition to radiation to at least partially polymerize the polymerizable material to provide a coating of first swollen hydrophilic gel material adhered to the substrate.

* * * * *

UNITED STATES PATENT AND TRADEMARK OFFICE
CERTIFICATE OF CORRECTION

PATENT NO. : 10,618,266 B2
APPLICATION NO. : 14/514429
DATED : April 14, 2020
INVENTOR(S) : Robin Wright It is certified that error appears in the above-identified patent and that said Letters Patent is hereby corrected as shown below:

On the Title Page

Page 2, Column 2 Item (56) Other Publications
Line 17, delete "Nanopatterened" and insert -- Nanopatterned --, therefor.

In the Specification

Column 16
Line 1, delete "diethylaminoethylmethacylate," and insert -- diethylaminoethylmethacrylate, --, therefor.

Column 17
Line 63, delete "(2-hydroxyethoxyl)" and insert -- (2-hydroxyethoxy) --, therefor.

Column 19
Line 23, delete "repellants," and insert -- repellents, --, therefor.
Line 33, delete "iodophores)," and insert -- iodophors), --, therefor.

Column 22
Line 53, delete "lease" and insert -- least --, therefor.

Column 23
Line 3, delete "form" and insert -- from --, therefor.

Column 30
Lines 6-7, delete "% Coverage/100" and insert -- %Coverage/100 --, therefor.
Lines 6-7, delete "Wt %$_{B.A.}$/100" and insert -- Wt%$_{B.A.}$/100 --, therefor.
Line 12, delete "(% Coverage/" and insert -- (%Coverage/ --, therefor.
Line 31, delete "(Wt %$_{B.A.}$/" and insert -- (Wt%$_{B.A.}$/ --, therefor.

Signed and Sealed this
Eighteenth Day of August, 2020

Andrei Iancu
*Director of the United States Patent and Trademark Office*

CERTIFICATE OF CORRECTION (continued)
U.S. Pat. No. 10,618,266 B2

Column 31
Line 25, delete "(% SurfaceArea$_{F.S.}$)" and insert -- (%SurfaceArea$_{F.S.}$) --, therefor.
Lines 25-26, delete "Wt %$_{B.A.}$/100" and insert -- Wt%$_{B.A.}$/100 --, therefor.
Lines 28-29, delete "(% SurfaceArea$_{F.S.}$)" and insert -- (%SurfaceArea$_{F.S.}$) --, therefor.
Line 40, delete "(Wt %$_{B.A.}$/" and insert -- (Wt%$_{B.A.}$/ --, therefor.

Column 32
Line 43, delete "adhesives," and insert -- adhesives. --, therefor.

Column 33
Line 8, delete "(e g,)" and insert -- (e.g.,) --, therefor.
Lines 34-35, delete "poly(l-butene),"" and insert -- "poly(1-butene), --, therefor.

Column 38
Line 50, after "material" insert -- . --.

Column 39
Line 58, delete "vasodilaters," and insert -- vasodilators, --, therefor.

Column 40
Line 49, delete "moncaprate," and insert -- monocaprate, --, therefor.
Line 57, delete "octenidene," and insert -- octenidine, --, therefor.

Column 44
Line 16, delete "deNemours" and insert -- de Nemours --, therefor.

Column 45
Line 5, delete "deNemours" and insert -- de Nemours --, therefor.

Column 48
Line 50, after "comprising" insert -- : --.
Line 59, after "thereof" insert -- . --.

Column 49
Line 35, delete "(2-hydroxyethoxyl)" and insert -- (2-hydroxyethoxy) --, therefor.

Column 51
Line 49, after "thereof" insert -- . --.

Column 52
Line 13, delete "(2-hydroxyethoxyl)" and insert -- (2-hydroxyethoxy) --, therefor.
Line 37, after "thereof" insert -- . --.

Column 57
Line 24, after "comprising" insert -- : --.
Line 50, delete "poloymerizable" and insert -- polymerizable --, therefor.

Column 58
Line 40, after "material" insert -- . --.

Column 59
Line 41, after "comprising" insert -- : --.
Line 61, delete "poloymerizable" and insert -- polymerizable --, therefor.

Column 60
Line 56, delete "Staphyloccoccus" and insert -- Staphylococcus --, therefor.
Line 63, delete "Meuller" and insert -- Mueller --, therefor.

Column 62
Lines 50-51, delete "(2-hydroxyethoxyl)" and insert -- (2-hydroxyethoxy) --, therefor.

Column 65
Line 28, delete "innoculated" and insert -- inoculated --, therefor.

In the Claims

Column 68
Line 12, Claim 9, delete "precurser" and insert -- precursor --, therefor.